US008592362B2

(12) United States Patent
Benjamin et al.

(10) Patent No.: US 8,592,362 B2
(45) Date of Patent: Nov. 26, 2013

(54) METHOD TO PREDICT RESPONSE TO PHARMACOLOGICAL CHAPERONE TREATMENT OF DISEASES

(75) Inventors: Elfrida Benjamin, Millstone Township, NJ (US); Hung V. Do, New Hope, PA (US); Xiaoyang Wu, Edison, NJ (US); John Flanagan, East Windsor, NJ (US); Brandon Wustman, San Diego, CA (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

(21) Appl. No.: 12/855,468

(22) Filed: Aug. 12, 2010

(65) Prior Publication Data
US 2011/0212996 A1   Sep. 1, 2011

Related U.S. Application Data

(63) Continuation of application No. PCT/US2009/033963, filed on Feb. 12, 2009.

(60) Provisional application No. 61/028,141, filed on Feb. 12, 2008, provisional application No. 61/035,684, filed on Mar. 11, 2008, provisional application No. 61/093,631, filed on Sep. 2, 2008, provisional application No. 61/113,496, filed on Nov. 11, 2008.

(51) Int. Cl.
C07K 14/00   (2006.01)

(52) U.S. Cl.
USPC ............................................. 514/1

(58) Field of Classification Search
USPC .............................................. 514/1
See application file for complete search history.

(56) References Cited

U.S. PATENT DOCUMENTS

| 7,851,143 B2 * | 12/2010 | Kaneski et al. ............. 435/4 |
| 2005/0203019 A1 | 9/2005 | Conn |
| 2006/0264467 A1 | 11/2006 | Mugrage et al. |
| 2007/0021381 A1 | 1/2007 | Fan et al. |
| 2007/0270486 A1 | 11/2007 | Kopito et al. |
| 2011/0152319 A1 | 6/2011 | Benjamin et al. |

FOREIGN PATENT DOCUMENTS

| WO | WO99/62517 | 12/1999 |
| WO | WO2007/137072 | 11/2007 |

OTHER PUBLICATIONS

Ishii et al. Sep. 1, 2007; Mutant a-galactosidase A enzymes identified in Fabry disease patients with residual enzyme activity: biochemical characterization and restoration of normal intracellular processing by 1-deoxygalactonorjirimycin. Biochemi J. 406(2): 285-295.*
Yam et al. 2006; Pharmacological chaperone corrects lysosomal storage in Fabry disease caused by trafficking-incompetent variants. Am. J. Physiol. Cell Physiol. 290: C1076-C1082.*
Sakuraba, 2010 at fabry-database.org/mutants.*
International Search Report Oct. 22, 2009.
Alfonso et al., "Miglustat (NB-DNJ) works as a chaperone for mutated acid beta-glucosidase in cells transfected with several Gaucher disease mutations", *Blood cells, Molecules and Diseases*, 35(2): 268-276 (2005).
Fan et al., "Cell-based screening of active-site specific chaperone for the treatment of Fabry disease", *Methods in Enzymology*, 363:412-420 (2003).
Fan et al,, "Accelerated transport and maturation of lysosomal.alpha.-galactosidase A in Fabry lymphoblasts by an enzyme inhibitor", *Nature Medicine*, 5(1): 112-115 (1999).
Lei et al., "Enzyme enhancement activity of N-octyl-beta-valienamine on beta-glucosidase in cells transfected with several Gaucher disease mutations", *Biochimica et Biophysica Acta. Molecular Basis of Disease*, 1772(5):587-596 (2007).
Shimotori et al., "Novel mutations of the GLA gene in Japanese patients with fabry disease and their functional characterization by active site specification chaperone", *Human Mutaion*, 29(2): 331 (2008).
Shin et al., "Screening for pharmacological chaperones in Fabry disease", *Biochemical and Biophysical Research Communications*. 359:168-173 (2007).
Wustman et al., "114. Pharmacological chaperone therapy for Gaucher disease: Mechanism of action, a survey of responsive mutations and phase I clinical trial results", *Molecular Genetics and Metabolism*, 93(2):44 (2008).
U.S. Appl. No. 12/860,611, Apr. 27, 2012 Non-Final Office Action.
"QIAGEN Supplementary Protocol: Transient transfection of COS-7 cells in 96-well plates using Polyfect Transfection Reagent", retrieved from the Internet: URL:www.qiagen.com/literature/render. aspx?id=543 [retrieved on Jun. 21, 2012].
"Transfecting Plasmid DNA into COS-7 Cells Using Lipofectamine (TM) LTX Reagent", Jun. 9, 2006, retrieved from the Internet: URL:www.invitrogen.com [retrieved on Jun. 21, 2012].
"QIAGEN Supplementary Protocol: Fast-forward protocol for transient transfection of 293 cells in 96-well plates using effectene transfection reagent", Nov. 1, 2006, retrieved from the Internet: URL:www.qiagen.com, [retrieved on Jun. 21, 2012].
"QIAGEN Supplementary Protocol: Transient transfection of 293 cells in 96-well plates using Polyfect Transfection Reagent", Aug. 1, 2001, retrieved from the Internet: URL:www.qiagen.com [retrieved on Jun. 21, 2012].
"Transfecting Plasmid DNA into HEK 293 Cells Using Lipofectamine (TM) LTX Reagent", Jan. 1, 2006, retrieved from the Internet: URL:www.invitrogen.com, [retrieved on Jun. 21, 2012].
"Transfecting Plasmid DNA into GripTite (TM) 293 MSR Cells Using Lipofectamine (TM) LTX Reagent", Jan. 1, 2006, retrieved from the Internet: URL:htp://www.invitrogen.com/etc/medialib/en/filelibrary/pdf/protocols.Par.18853.File.dat/Human_embryonic_kidney.pdf, [retrieved on Jun. 21, 2012].

* cited by examiner

*Primary Examiner* — Karen Cochrane Carlson
(74) *Attorney, Agent, or Firm* — SorinRand LLP

(57) ABSTRACT

The present invention provides methods to determine whether a patient with a lysosomal storage disorder will benefit from treatment with a specific pharmacological chaperone. The present invention exemplifies an in vitro method for determining α-galactosidase A responsiveness to a pharmacological chaperone such as 1-deoxygalactonojirimycin in a cell line expressing a mutant from of α-galactosidase A. The invention also provides a method for diagnosing Fabry disease in patients suspected of having Fabry disease.

4 Claims, 37 Drawing Sheets

Fig. 1A

Fabry Mutations Generated by Site-Directed Mutagenesis

| Missense | L45R | M72R | R112H | G147R | G183S | R227P | D264V | A285P | Q312R | R356G | P409S | V390frX8 |
|---|---|---|---|---|---|---|---|---|---|---|---|---|
| M1I | H46L | M72V | R112S | S148N | G183V | R227Q | D264Y | W287C | D313G | R356W | P409T | 401ins1aa/T401S |
| M1K | H46R | A73V | F113L | S148R | Y184C | A230T | P265L | W287G | D313Y | Q357X | T410A | del20-24aa |
| M1L | H46Y | M76R | F113S | Y152C | M187T | D231G | P265R | A288D | V316E | E358A | T410I | del13-8aa |
| M1R | W47G | M76T | H17S | D155H | M187V | D231N | D266E | A288P | I317N | E358G | T410K | del153aa |
| M1T | W47L | W81C | R118C | A156T | L191P | D231V | D266H | I289F | I317T | E358K | T410P | del205-7aa |
| M1V | E48D | W81S | L120P | A156V | L191Q | D234E | D266N | I289S | N320I | I359T | G411D | del254aa |
| A13P | E48K | G85D | L120S | A156Y | T194I | D234Y | D266V | M290I | N320K | G360C | L414S | del358aa |
| L14P | R49C | G85M | A121P | W162C | V199M | S235C | D266Y | A291T | N320Y | G360D | L415P | ins247-8aa |
| L16H | R49G | Y86C | A121T | W162G | S201F | S235F | M267I | A292P | Q321E | G360S | L33Y | |
| L16P | R49L | Y86D | V124D | W162R | S201Y | W236C | M267R | A292T | Q321L | G361R | L166G | |
| F18S | R49P | Y88P | H125P | G163V | C202W | W236R | L268S | P293A | Q321R | P362L | H46S | |
| L19P | R49S | L89P | S126G | D165V | C202Y | W236N | V269A | P293H | G325D | R363C | I124F | |
| A20P | F50C | L89R | G128E | D165Y | P205L | S238N | V269M | P293S | G325S | R363H | | |
| A31V | M51I | C90R | L129P | D165Y | P205R | I239T | I270T | P293T | Q327E | R363P | | |
| L32P | M51K | D1T | L131P | D156Y | P205S | I242F | G271C | F295C | Q327K | L372P | Complex | |
| D33Y | C52Z | D92G | G132E | L166V | P205T | I242N | G271S | M296I | G328A | L372R | D55V/Q57L | |
| N34K | C52R | D92H | G132R | L167P | L206P | L243F | G271V | M296V | G328E | G373D | L120P/A121T | |
| N34S | C52S | D92N | Y134H | K168N | Y207C | L243W | N272K | S297C | G328R | G373R | | |
| G35R | C52Y | D92Y | Y134S | K168R | Y207H | D244N | N272S | S297F | G328V | G373S | Small Ins/Del | |
| L36F | L54P | D93G | A135V | F169S | Y207S | D244H | F273L | N298H | E336K | A377D | 19del5aa | |
| L36S | D55V | D93N | D136H | D170H | N215D | S247C | L275F | N298K | V339E | C378R | 86del6aa | |
| A37V | C56F | D93V | D136Y | D170V | N215S | S247P | S276G | N298S | W340R | C378Y | 113del8aa | |
| P40L | C56G | C94S | G138E | G171C | Y216C | Q250P | S276N | D299G | E341D | C382W | 120del2aa/L120H | |
| P40S | C56Y | C94Y | G138R | G171D | Y216P | I253T | Q279E | L300F | E341K | C382Y | 152ins1aa/Y152D | |
| T41I | Q57L | W95L | N139T | G171R | I219N | A257P | Q279H | L300H | R342L | I384N | 153del1aa | |
| M42L | E59K | W95S | T141I | C172F | C223G | G258R | Q279K | L300P | R342Q | T385P | 205del3aa | |
| M42R | P60L | A97P | C142G | C172G | C223R | G258V | Q279R | R301G | L344P | Q386P | 205del7aa | |
| M42T | C63Y | A97V | C142W | C172R | C223Y | P259L | Q280H | R301P | S345P | P389R | 254del1aa | |
| M42V | S65T | R100K | C142Y | C172S | N224D | P259R | Q280K | R301Q | A348P | F396Y | 281del1aa/V281A | |
| G43D | E66G | R100T | A143P | C172W | N224S | G260A | T282A | B03N | W349R | E398K | 358del1aa | |
| G43R | E66K | E103Q | A143T | C172Y | H225D | G261D | T282N | K308N | A350P | L403S | 382del1aa | |
| G43S | E66Q | L106R | G144R | C174G | H225R | W262C | Q283P | A309P | A352D | I407K | 403del1aa | |
| G43V | L68F | Q107L | P146S | G183A | W226C | N263S | M284T | L310F | I354K | I407R | 247ins3aa | |
| W44C | M72I | R112C | G147E | G183D | W226R | D264A | A285D | Q312H | N355K | P409A | 247ins8aa | |

Fig. 1B

Fabry Mutations Generated by Site-Directed Mutagenesis

| Missense | R49L | *D93V* | P146S | C202Y | *A257P* | M284T | N320Y | C378Y |
|---|---|---|---|---|---|---|---|---|
| *M1T* | *R49P* | C94Y | *G147R* | C202W | G258R | A285P | Q321E | C378R |
| *M1R* | R49S | C94S | S148N | P205R | P259R | A285D | Q321R | C382Y |
| M1I | F50C | W95S | S148R | P205L | P259L | W287G | G325D | C382W |
| L14P | M51K | A97V | Y152C | P205T | G260A | W287C | Q327K | *I384N* |
| *L16P* | M51I | *A97P* | D155H | Y207C | G261D | A288D | Q327E | T385P |
| L16H | C52G | R100K | A156V | Y207S | W262C | A288P | G328R | Q366P |
| *L19P* | C52R | R100T | A156T | N215S | N263S | I289F | G328A | *P389R* |
| A20P | C52S | E103Q | W162R | Y216D | D264V | M290I | G328E | F396Y |
| A31V | C56F | R112H | W162C | I219N | D264Y | A292P | G328V | E398K |
| L32P | C56G | R112S | G163V | C223R | P265R | P293A | E338K | L403S |
| D33Y | C56Y | R112C | D165V | C223G | P265L | P293S | V339E | I407K |
| N34K | E59K | F113L | *L166G* | C223Y | D266N | P293T | W340R | *P409T* |
| N34S | C63Y | F113S | L166V | N224S | D266H | F295C | E341D | *P409A* |
| G35R | S65T | R118C | L167P | N224D | D266V | M296I | E341K | P409S |
| *A37V* | E66G | L120P | K168N | H225R | D266E | M296V | R342Q | T410K |
| P40L | E66K | *L120S* | K168R | W226R | M267R | S297C | L344P | T410A |
| P40S | E66Q | A121P | F169S | W226C | M267I | S297F | S345P | G411D |
| T41I | L68F | A121T | D170V | R227Q | L268S | N298S | A348P | L414S |
| M42T | M72R | V124D | D170H | A230T | V269A | N298K | A350P | L415P |
| M42L | M72I | G128E | G171D | D231N | V269M | N298H | A352D | |
| M42V | M72V | L129P | G171R | D231G | I270T | D299G | I354K | |
| G43D | A73V | L131P | C172Y | D234E | G271C | L300F | N355K | |
| G43S | M76R | G132E | C172F | D234Y | G271S | L300H | R356W | |
| G43V | W81C | G132R | C172W | S235C | G271V | L300P | E358G | |
| G43R | W81S | Y134S | C172R | W236R | N272K | R301G | E358K | |

Fig. 1B (Cont.)

| | | | | | | | | |
|---|---|---|---|---|---|---|---|---|
| W44C | G85D | A135V | C172G | W236L | N272S | R301Q | E358A | |
| L45R | Y86C | D136H | G183D | W236C | S276N | R301P | I359T | |
| H46R | Y88D | G138E | G183S | I239T | S276G | I303N | G360S | Small Ins/Del |
| H46S | L89P | G138R | M187T | I242F | Q279R | L310F | G361R | del20-24aa |
| H46L | L89R | T141I | M187V | I242N | Q279H | Q312H | P362L | del13-8aa |
| H46Y | I91T | C142R | L191Q | L243F | Q279E | D313Y | R363H | del153aa |
| W47G | D92N | C142W | L191P | D244N | Q279K | V316E | R363C | del205-7aa |
| W47L | D92H | C142Y | T194I | D244H | Q280H | I317N | G373D | del254aa |
| E48D | D92Y | A143T | V199M | S247P | Q280K | I317T | G373R | del358aa |
| E48K | D93G | A143P | S201F | S247C | T282N | N320I | G373S | ins247-8aa |
| R49G | D93N | G144V | S201Y | Q250P | Q283P | N320K | A377D | |

Fig. 1C

Fabry Mutations Generated by Site-Directed Mutagenesis

| Missense | R49L | D93V | P146S | C202Y | A257P | M284T | N320Y | C378Y |
|---|---|---|---|---|---|---|---|---|
| M1T | R49P | C94Y | G147R | C202W | G258R | A285P | Q321E | C378R |
| M1R | R49S | C94S | S148N | P205R | P259R | A285D | Q321R | C382Y |
| M1I | F50C | W95S | S148R | P205L | P259L | W287G | G325D | C382W |
| L14P | M51K | A97V | Y152C | P205T | G260A | W287C | Q327K | I384N |
| L16P | M51I | A97P | D155H | Y207C | G261D | A288D | Q327E | T385P |
| L16H | C52G | R100K | A156V | Y207S | W262C | A288P | G328R | Q386P |
| L19P | C52R | R100T | A156T | N215S | N263S | I289F | G328A | P389R |
| A20P | C52S | E103Q | W162R | Y216D | D264V | M290I | G328E | F396Y |
| A31V | C56F | R112H | W162C | I219N | D264Y | A292P | G328V | E398K |
| L32P | C56G | R112S | G163V | C223R | P265R | P293A | E338K | L403S |
| L33Y | C56Y | R112C | D165V | C223G | P265L | P293S | V339E | I407K |
| N34K | E59K | F113L | L166G | C223Y | D266N | P293T | W340R | P409T |
| N34S | C63Y | F113S | L166V | N224S | D266H | F295C | E341D | P409A |
| G35R | S65T | R118C | L167P | N224D | D266V | M296I | E341K | P409S |
| A37V | E66G | L120P | K168N | H225R | D266E | M296V | R342Q | T410K |
| P40L | E66K | L120S | K168R | W226R | M267R | S297C | L344P | T410A |
| P40S | E66Q | A121P | F169S | W226C | M267I | S297F | S345P | G411D |
| T41I | L68F | A121T | D170V | R227Q | L268S | N298S | A348P | L414S |
| M42T | M72R | V124D | D170H | A230T | V269A | N298K | A350P | L415P |
| M42L | M72I | G128E | G171D | D231N | V269M | N298H | A352D | |
| M42V | M72V | L129P | G171R | D231G | I270T | D299G | I354K | |
| G43D | A73V | L131P | C172Y | D234E | G271C | L300F | N355K | |
| G43S | M76R | G132E | C172F | D234Y | G271S | L300H | R356W | |
| G43V | W81C | G132R | C172W | S235C | G271V | L300P | E358G | |
| G43R | W81S | Y134S | C172R | W236R | N272K | R301G | E358K | |

Fig. 1C (Cont.)

| W44C | G85D | A135V | C172G | W236L | N272S | R301Q | E358A | |
|---|---|---|---|---|---|---|---|---|
| L45R | Y86C | D136H | G183D | W236C | S276N | R301P | I359T | |
| H46R | Y88D | G138E | G183S | I239T | S276G | I303N | G360S | Small Ins/Del |
| H46S | L89P | G138R | M187T | I124F | Q279R | L310F | G361R | del20-24aa |
| H46L | L89R | T141I | M187V | I242N | Q279H | Q312H | P362L | del13-8aa |
| H46Y | I91T | C142R | L191Q | L243F | Q279E | D313Y | R363H | del153aa |
| W47G | D92N | C142W | L191P | D244N | Q279K | V316E | R363C | del205-7aa |
| W47L | D92H | C142Y | T194I | D244H | Q280H | I317N | G373D | del254aa |
| E48D | D92Y | A143T | V199M | S247P | Q280K | I317T | G373R | del358aa |
| E48K | D93G | A143P | S201F | S247C | T282N | N320I | G373S | ins247-8aa |
| R49G | D93N | G144V | S201Y | Q250P | Q283P | N320K | A377D | |

| Mutation | Relative Increase | EC₅₀ (μM) | Mutation | Relative Increase | EC₅₀ (μM) | Mutation | Relative Increase | EC₅₀ (μM) |
|---|---|---|---|---|---|---|---|---|
| M1R | 2.6±0.4 | 3±1 | G163V | 3.5±0.4 | 27±9 | A288D | 6±1 | 200±40 |
| L14P | 2.5±0.4 | 3±1 | L166V | 4.8±0.5 | 13±4 | A288P | 20±1 | 25±1 |
| L16H | 5±1 | 0.3±0.1 | K168N | 22±3 | 70±30 | I289F | 19±4 | 300±50 |
| L16P | 5±1 | 0.8±0.3 | F169S | 2.7±0.4 | 1±0 | A292P | 3±1 | 160±40 |
| L19P | 2.3±0.3 | 1.3±0.5 | G171C | 9±2 | 190±80 | P293A | 21±3 | 475±100 |
| A20P | 15±0.1 | 0.3±0.1 | G171R | 4±1 | 4±1 | P293S | 19±2 | 560±210 |
| L32P | 7±1 | 2.2±0.3 | C172S | 7±2 | 680±200 | P293T | 12±2 | 36±8 |
| D33Y | 3±1 | 5±1 | G183A | 2.3±0.3 | 7±3 | F295C | 15±2 | 20±3 |
| N34K | 19±2 | 100±30 | G183D | 15±3 | 40±10 | M296L | 2.6±0.1 | 0.7±0.2 |
| G35R | 5±2 | 7±2 | G183S | 7±1 | 7±2 | M296V | 1.9±0.1 | 0.7±0.3 |
| L36F | 10±1 | 13±4 | Y184C | 15±1 | 74±1 | S297C | 3±1 | 620±20 |
| A37V | 1.6±0.1 | 23±9 | M187T | 8±2 | 23±8 | N298H | 9.4±0.4 | 700±100 |
| P40L | 3.8±0.2 | 39±18 | M187V | 5±1 | 16±1 | N298L | 5±2 | 38±18 |
| P40S | 3±1 | 3±1 | L191P | 2.0±0.3 | 7±2 | N298S | 2.8±0.1 | 1.4±0.2 |
| T41I | 1.3±0.1 | 0.3±0.1 | L191Q | 16±3 | 150±60 | D299G | 15±2 | 1500±140 |
| M42L | 1.5±0.1 | 7±2 | T194I | 12±2 | 19±1 | L300R | 6±1 | 3±1 |
| M42R | 5±1 | 12±5 | V199M | 1.2±0.1 | 4±2 | L300P | 12±1 | 8±2 |
| M42T | 18±1 | 42±16 | S201F | 8±2 | 2±1 | R301G | 1.8±0.2 | 2.5±0.4 |
| M42V | 14±2 | 120±20 | S201Y | 6.3±0.3 | 15±3 | R301P | 42±4 | 120±14 |
| L45R | 17±4 | 40±5 | P205L | 9±1 | 260±50 | R301Q | 6.2±0.3 | 3.8±0.2 |
| W47L | 5±1 | 11±3 | P205R | 4±1 | 70±30 | I303N | 14±1 | 70±20 |
| E48D | 7±2 | 100±37 | P205S | 5±2 | 4±1 | K308N | 7±1 | 24±8 |
| E48K | 6±1 | 4±2 | P205T | 8±2 | 2±0 | A309P | 26±5 | 33±10 |
| R49G | 3±1 | 4±1 | Y207C | 7±2 | 500±200 | L310F | 17±0 | 70±10 |
| R49L | 11±2 | 80±20 | Y207S | 3.2±0.4 | 67±5 | Q312H | 12±2 | 15±2 |
| R49P | 3±1 | 3±1 | N215D | 1.2±0.1 | 9±4 | Q312R | 2±0 | 10±1 |
| R49S | 4±1 | 5±2 | N215S | 3±0 | 4±1 | D313G | 1.4±0.1 | 8±2 |
| M51I | 1.5±0.1 | 3±1 | Y216C | 13±1 | 36±8 | V316E | 5±1 | 600±100 |
| M51K | 2.9±0.3 | 2±0 | Y216D | 16±1 | 350±150 | I317N | 9±1 | 80±10 |
| C52R | 4±1 | 53±29 | I219N | 13±1 | 167±67 | I317T | 5±1 | 10±2 |
| L54P | 16±2 | 8±2 | N224D | 13±3 | 190±40 | N320I | 23±3 | 40±10 |
| D55V | 15±2 | 3±1 | N224S | 2.6±0.1 | 6±2 | N320V | 18±2 | 300±80 |
| C56F | 16±1 | 28±6 | H225R | 27±2 | 900±100 | Q321E | 21±3 | 90±30 |
| C56G | 7±1 | 400±100 | A230T | 4±1 | 27±12 | Q321L | 12±1 | 16±3 |
| C56Y | 14±3 | 50±18 | D234E | 14±3 | 340±150 | Q321R | 3±1 | 7±1 |
| E59K | 3±1 | 35±14 | S235C | 4.0±0.1 | 120±40 | G325D | 14±4 | 360±120 |
| P60L | 5±2 | 1.7±0.7 | W236L | 9±2 | 800±160 | G325S | 3±1 | 1.7±0.1 |
| S65T | 3±1 | 2.2±0.8 | S238N | 2.8±0.2 | 1.5±0.3 | Q327E | 2.4±0.2 | 11±2 |
| E66G | 2±1 | 4±1 | I239T | 1.7±0.1 | 3±1 | G328A | 19±5 | 14±2 |
| E66K | 4±2 | 11±4 | I242N | 12±1 | 9±1 | E338K | 4±0 | 16±4 |
| E66Q | 2±1 | 5±2 | L243F | 8±1 | 10±2 | V339E | 2±0 | 7±2 |
| L68F | 11±2 | 100±30 | L243W | 37±2 | 21±4 | W340R | 10±2 | 100±40 |
| M72R | 7±1 | 700±250 | D244N | 4±2 | 4±1 | E341D | 3±0 | 17±4 |
| M72V | 2.2±0.2 | 0.6±0.1 | D244H | 3±1 | 1.2±0.4 | R342Q | 4±2 | 16±7 |
| A73V | 1.4±0.1 | 0.9±0.3 | S247C | 2.0±0.3 | 8±1 | S345P | 8±1 | 75±5 |
| M76R | 3±1 | 6±2 | S247P | 16±3 | 350±120 | A348P | 2±0 | 5±2 |
| M76T | 9±1 | 11±3 | Q250P | 2.1±0.1 | 6±2 | A352D | 5±1 | 150±30 |
| W81C | 19±1 | 70±20 | I253T | 1.7±0.1 | 1.4±0.3 | I354K | 19±4 | 17±3 |
| W81S | 4±1 | 25±12 | A257P | 3.3±0.4 | 5±1 | R355W | 3±1 | 1.0±0.1 |
| G85D | 7±1 | 12±2 | G258V | 16±4 | 15±4 | E358A | 21±2 | 9±2 |
| G85M | 2.3±0.2 | 2.6±0.6 | P259L | 8±3 | 9±1 | K358G | 7±1 | 20±10 |
| Y88D | 3.4±0.4 | 52±17 | P259R | 3.3±0.4 | 2±1 | K358K | 3±1 | 400±100 |
| I91T | 12±1 | 6±2 | G260A | 9±3 | 12±1 | I359T | 1.5±0.1 | 4±2 |
| C94Y | 2.1±0.4 | 0.8±0.4 | G261D | 16±3 | 150±50 | G360D | 12±0 | 15±3 |
| W95S | 4±1 | 300±50 | N263S | 5±1 | 2.5±0.4 | G360S | 1.8±0.2 | 9±3 |
| A97P | 8±1 | 43±14 | D264Y | 13±3 | 18±4 | G361R | 10±1 | 7±2 |
| A97V | 3±1 | 0.8±0.2 | P265L | 2.7±0.2 | 1.1±0.1 | P362L | 7±2 | 3±1 |
| R112C | 15±2 | 300±60 | P265R | 13±1 | 97±27 | R363C | 2.3±0.3 | 2±1 |
| R112H | 5±1 | 25±0.5 | M267I | 1.6±0.1 | 6±2 | R363H | 1.7±0.1 | 1.0±0.4 |
| R112S | 8±2 | 90±38 | L268S | 1.5±0.1 | 0.7±0.3 | R363P | 21±5 | 120±40 |
| F113L | 2.3±0.2 | 2±1 | V269A | 13±2 | 22±9 | G373D | 3.2±0.4 | 5±2 |
| D117S | 3±1 | 2±1 | V269M | 4±1 | 2.0±0.6 | G373S | 2.6±0.4 | 2±1 |
| R118C | 1.4±0.1 | 8±2 | I270T | 11±2 | 10±0 | E398K | 1.3±0.1 | 7±2 |
| L120P | 6±2 | 20±9 | G271S | 22±8 | 24±2 | L403S | 1.6±0.1 | 16±5 |
| A121T | 3±1 | 0.3±0.1 | N272K | 3±1 | 17±7 | P409R | 10±2 | 5±1 |
| A135V | 14±2 | 350±120 | N272S | 5±1 | 228±86 | P409S | 15±2 | 3±1 |
| D136H | 5±1 | 23±5 | S276G | 22±1 | 9±1 | P409T | 5±1 | 13±0.5 |
| A143T | 1.3±0.1 | 4±1 | S276N | 9±2 | 22±7 | T410A | 19±3 | 2±1 |
| G144V | 21±6 | 38±14 | Q279E | 5±1 | 23±5 | T410I | 14±4 | 3.8±0.2 |
| G147R | 2.4±0.4 | 4±2 | Q279H | 5±1 | 61±26 | T410P | 20±5 | 1200±580 |
| S148N | 18±3 | 1400±400 | Q279R | 4±0 | 12±5 | G411D | 15±0 | 6±2 |
| Y152C | 4±1 | 28±11 | Q280H | 5±1 | 6±1 | L414E | 1±1 | 18±3 |
| A156T | 13±1 | 50±10 | Q280K | 1.7±0.1 | 1.1±0.3 | 254del1 | 1.6±0.1 | 3±1 |
| A156V | 19±2 | 44±9 | T282A | 15±5 | 24±3 | 247ins8 | 21±1 | 400±180 |
| A156Y | 5±1 | 50±10 | M284T | 20±5 | 28±8 | D55V/Q57L | 24±5 | 8±4 |
| W162G | 9±1 | 13±4 | W287C | 20±4 | 1000±100 | 401ins/T401S | 4±1 | 11±3 |

Fig. 2A: DGJ-Responsive Mutations described in Figure 1A: Potency and Response Magnitude

| Mutation | Relative Increase (fold) | EC$_{50}$(μM) | Mutation | Relative Increase (fold) | EC$_{50}$(μM) |
|---|---|---|---|---|---|
| L14P | 3.0±0.4 | 2.6±0.8 | D244H | 3.0±1.0 | 1.2±0.4 |
| A20P | 1.5±0.1 | 0.3±0.1 | P259R | 3.0±0.4 | 2.1±0.5 |
| L32P | 7.0±1.0 | 2.2±0.3 | P259L | 8.4±3.0 | 9.0±0.5 |
| D33Y | 2.9±0.5 | 5.4±1.4 | G260A | 8.5±2.6 | 12±1 |
| N34K | 18±2 | 100±31 | N263S | 4.8±1.2 | 2.5±0.4 |
| G35R | 5.0±1.6 | 7.0±1.5 | D264Y | 13±3 | 18±4 |
| P40L | 4.0±0.2 | 39±16 | P265R | 13±1 | 96±27 |
| P40S | 3.0±0.6 | 2.6±0.8 | P265L | 2.7±0.2 | 1.1±0.1 |
| T41I | 1.0±0.1 | 0.3±0.1 | P265R | 13±1 | 97±37 |
| M42T | 18±1 | 42±16 | M267I | 1.6±0.2 | 5.6±2.5 |
| M42V | 14±2 | 123±23 | L268S | 1.5±0.1 | 0.7±0.3 |
| L45R | 17±4 | 39±5 | V269A | 13±2 | 22±9 |
| W47L | 5.0±1.0 | 11±3 | V269M | 3.8±0.9 | 2.6±0.6 |
| E48D | 6.7±1.8 | 105±37 | I270T | 11±2 | 10.0±0.3 |
| E48K | 6.0±1.0 | 4.4±2.0 | G271S | 22±8 | 24±2 |
| R49G | 3.0±0.5 | 3.6±1.4 | N272K | 3.3±0.7 | 17±7 |
| R49L | 11±2 | 76±19 | N272S | 4.6±0.8 | 228±86 |
| R49S | 4.0±1.0 | 5.3±2.5 | S276N | 9.0±2.3 | 22±7 |
| M51I | 1.5±0.1 | 2.9±0.8 | S276G | 22±1 | 9.0±1.0 |
| M51K | 3.0±0.3 | 1.8±0.6 | Q279E | 4.5±0.6 | 22±5 |
| C52R | 3.6±0.6 | 5.3±2.5 | Q279H | 4.7±0.7 | 61±26 |
| C56F | 16±1 | 28±6 | Q279R | 3.5±0.3 | 11.9±5.6 |
| Q56G | 6.5±1.0 | 400±77 | Q280H | 4.7±1.0 | 5.4±0.8 |
| E59K | 3.4±0.5 | 35±14 | Q280K | 1.7±0.1 | 1.1±0.3 |
| S65T | 3.0±0.5 | 2.2±0.6 | M284T | 20±4 | 28±8 |
| E66G | 1.6±0.2 | 3.9±1.5 | W287C | 20±4 | 968±74 |
| E66K | 3.7±1.0 | 10.8±4.5 | A288D | 5.7±0.0 | 199±36 |
| E66Q | 2.3±0.7 | 5.0±2.0 | A288P | 20±1 | 2.5±1 |
| L68F | 10.9±1.7 | 112±23 | I289F | 18±4 | 308±18 |
| M72R | 6.6±1.4 | 685±255 | A292P | 3.0±0.5 | 159±42 |
| M72V | 2.0±0.2 | 0.6±0.1 | P293A | 20±2 | 475±96 |
| A73V | 1.4±0.1 | 0.9±0.3 | P293S | 19±2 | 563±218 |
| M76R | 3.0±0.7 | 6.0±2.0 | F295C | 15±2 | 18±5 |
| W81S | 3.8±1.4 | 25±12 | M296I | 2.6±0.1 | 0.7±0.2 |
| Y88D | 3.4±0.4 | 52±17 | M296V | 1.9±0.1 | 0.7±0.3 |
| I91T | 12±2 | 5.9±2.5 | S297C | 3.0±0.7 | 616±230 |
| C94V | 2.0±0.4 | 0.8±0.3 | N298S | 2.8±0.0 | 1.4±0.2 |
| W95S | 4.0±0.8 | 312±52 | N298K | 5.2±2.2 | 38±18 |
| A97V | 3.0±0.5 | 0.8±0.5 | L300F | 5.5±1.3 | 3.4±0.8 |
| A97P | 7.7±1.4 | 43±14 | L300P | 12±1 | 6.0±1.6 |
| R112H | 5.0±0.5 | 2.5±0.5 | R301Q | 6.5±0.3 | 3.8±0.4 |
| R112C | 15±2 | 297±59 | R301P | 42±4 | 118±14 |
| R112S | 8.0±1.8 | 91±28 | I303N | 13±1 | 68±22 |
| F113L | 2.3±0.2 | 2.4±1.0 | L310F | 17±0 | 71±11 |
| R118C | 1.4±0.1 | 6.0±2.0 | Q312H | 12±2 | 15±2 |
| L120P | 5.7±2.3 | 20±9 | V316E | 5.0±0.7 | 627±143 |
| A121T | 2.6±0.5 | 0.3±0.1 | I317T | 5.0±1.4 | 10±2 |
| D136H | 5.0±1.0 | 23±5 | I317N | 9.4±1.0 | 83±24 |
| A143T | 1.3±0.1 | 4.3±1.3 | N320I | 23±3 | 39±12 |
| G144V | 21±6 | 38±14 | N320Y | 18±1 | 295±76 |
| G147R | 2.4±0.4 | 4.2±1.6 | Q321E | 21±3 | 90±35 |
| S148N | 18±2 | 1391±442 | Q321R | 3.4±1.1 | 7.0±0.8 |
| A156T | 13±1 | 47±10 | G325D | 12±2 | 323±102 |
| A156V | 19±2 | 44±9 | Q327E | 2.4±0.2 | 11±2 |
| L166V | 5.0±0.5 | 13±4 | G328A | 18±5 | 14±2 |
| K168N | 22±3 | 68±32 | E338K | 4.4±0.2 | 16±4 |
| G183S | 6.8±1.0 | 7.1±1.9 | W340R | 10.0±1.5 | 103±38 |
| G183D | 15±3 | 42±13 | E341D | 2.9±0.1 | 17±4 |
| M187T | 8.4±2.0 | 23±8 | R342Q | 4.0±1.4 | 16±7 |
| M187V | 4.9±1.2 | 16±1 | S345P | 8.2±0.6 | 76±5 |
| L191P | 20±0 | 6.5±2.5 | A348P | 1.6±0.0 | 4.8±2.3 |
| L191Q | 16±4 | 148±61 | A352D | 5.0±0.5 | 163±28 |
| T194I | 12±2 | 19±1 | I354K | 19±4 | 17±3 |
| V199M | 1.2±0.0 | 3.5±1.6 | R356W | 2.8±0.5 | 0.9±0.1 |
| S201F | 8±2 | 2.1±0.6 | E358A | 21±2 | 9.4±2.0 |
| S201Y | 6.0±0.3 | 15±3 | E358G | 7.3±0.6 | 20±9 |
| P205L | 8.5±0.8 | 260±54 | E358K | 2.3±0.6 | 400±117 |
| P205R | 4.0±0.7 | 70±30 | G361R | 9.7±0.8 | 7.2±2.2 |
| P205T | 7.7±2.0 | 2.4±0.4 | P362L | 7.2±1.5 | 2.7±0.7 |
| Y207S | 3.2±0.4 | 67±5 | R363H | 1.7±0.1 | 1.0±0.4 |
| N215S | 2.6±0.3 | 4.3±0.9 | R363C | 2.3±0.3 | 2.1±0.9 |
| I219N | 13±1 | 167±67 | G373D | 3.2±0.4 | 5.4±2.6 |
| N224D | 13±3 | 186±39 | G373S | 2.6±0.4 | 2.2±0.7 |
| N224S | 2.6±0.1 | 6.3±1.8 | E398K | 1.3±0.0 | 6.9±2.4 |
| H225R | 27±2 | 860±135 | P409S | 14±2 | 2.7±0.6 |
| D234E | 14±3 | 341±47 | T410A | 19±3 | 2.3±0.9 |
| I242N | 12±1 | 9.3±1.0 | G411D | 15±0 | 5.8±2.0 |
| L243F | 8±1 | 9.9±1.5 | L414S | 5.8±0.6 | 18±3 |
| D244N | 4.0±1.0 | 3.5±1.3 | Ins247-8 | 21±1 | 405±176 |

Fig. 2B: DGJ-Responsive Mutations described in Figure 1B: Potency and Response Magnitude

| Mutation | Fold of Increase | EC₅₀(uM) | Mutation | Fold of Increase | EC₅₀(uM) |
|---|---|---|---|---|---|
| L14P | 2.50±0.44 | 2.59±0.75 | M267I | 1.59±0.08 | 5.66±2.38 |
| A20P | 1.47±0.10 | 0.34±0.16 | V269M | 3.81±0.90 | 2.60±0.62 |
| L32P | 6.85±1.04 | 2.24±0.34 | I270T | 10.99±1.62 | 10.02±0.31 |
| N34K | 18.53±2.32 | 100.89±30.83 | G271S | 22.10±8.22 | 24.17±1.96 |
| G35R | 5.40±1.59 | 6.98±1.51 | S276N | 9.04±2.33 | 21.54±7.07 |
| P40L | 3.75±0.24 | 39.03±15.93 | S276G | 22.16±0.61 | 8.99±0.97 |
| P40S | 3.10±0.61 | 2.57±0.75 | Q279E | 4.52±0.63 | 22.46±4.98 |
| T41I | 1.29±0.09 | 0.32±0.10 | Q279H | 4.69±0.70 | 61.31±26.33 |
| L45R | 17.04±3.88 | 38.70±5.30 | Q279R | 3.47±0.34 | 11.93±5.58 |
| W47L | 4.73±1.22 | 10.83±3.20 | Q280H | 4.69±1.05 | 5.45±0.85 |
| E48K | 6.00±1.12 | 4.44±2.08 | Q280K | 1.70±0.10 | 1.09±0.26 |
| R49G | 3.44±0.54 | 3.64±1.36 | M284T | 19.92±4.56 | 28.31±7.83 |
| R49L | 10.93±1.71 | 75.71±18.70 | W287C | 20.11±3.61 | 968.45±74.22 |
| R49S | 3.56±0.81 | 5.26±2.62 | A288D | 5.67±0.61 | 198.63±36.31 |
| M51K | 2.87±0.26 | 1.82±0.56 | A288P | 19.52±0.70 | 25.33±1.44 |
| C52R | 3.62±0.57 | 53.08±22.95 | I289F | 18.53±4.44 | 308.39±48.52 |
| E59K | 3.41±0.49 | 34.77±13.52 | A292P | 3.07±0.51 | 158.87±41.66 |
| E66Q | 2.29±0.68 | 5.33±2.26 | P293A | 20.56±2.58 | 474.88±96.29 |
| M72V | 2.19±0.15 | 0.59±0.14 | P293S | 18.73±2.32 | 562.60±218.18 |
| A73V | 1.39±0.14 | 0.94±0.34 | F295C | 14.85±2.54 | 18.44±4.69 |
| M76R | 2.98±0.71 | 6.18±2.02 | M296I | 2.56±0.07 | 0.69±0.17 |
| I91T | 12.15±1.20 | 5.93±2.36 | M296V | 1.94±0.05 | 0.70±0.32 |
| C94Y | 2.12±0.36 | 0.79±0.35 | S297C | 2.99±0.74 | 616.10±230.41 |
| W95S | 4.02±0.79 | 312.17±52.17 | N298S | 2.79±0.02 | 1.42±0.21 |
| A97V | 2.70±0.50 | 0.78±0.26 | N298K | 5.20±2.22 | 38.12±18.48 |
| R112H | 4.85±0.48 | 2.54±0.47 | L300F | 5.53±1.31 | 3.35±0.80 |
| R112C | 15.34±1.94 | 296.59±59.28 | L300P | 12.38±1.39 | 6.04±1.56 |
| F113L | 2.33±0.19 | 2.39±0.90 | R301Q | 6.54±0.33 | 3.85±0.35 |
| A121T | 2.62±0.48 | 0.33±0.05 | R301P | 41.85±4.24 | 118.30±13.89 |
| A143T | 1.34±0.06 | 4.26±1.30 | I303N | 13.46±1.24 | 68.23±22.49 |
| G144V | 38.32±13.72 | 2.5±0.76 | L310F | 17.39±0.15 | 71.46±10.68 |
| A156V | 19.06±2.33 | 44.42±8.94 | Q312H | 12.39±2.11 | 15.38±2.49 |
| L166V | 4.77±0.51 | 12.94±4.03 | V316E | 4.99±0.74 | 627.13±142.62 |
| G183D | 14.71±3.41 | 41.60±12.82 | I317T | 5.06±1.37 | 10.14±2.48 |
| T194I | 12.39±2.05 | 18.93±0.89 | N320I | 23.24±2.77 | 38.92±11.74 |
| S201F | 8.43±2.18 | 2.08±0.63 | N320Y | 18.34±1.47 | 295.33±76.01 |
| S201Y | 5.97±0.34 | 15.31±3.24 | Q321E | 20.65±2.84 | 89.80±34.91 |
| P205R | 4.09±0.66 | 69.75±30.16 | Q321R | 3.35±1.12 | 7.01±0.80 |
| P205T | 7.69±2.03 | 2.42±0.42 | G325D | 12.23±1.99 | 323.52±102.44 |
| Y207S | 3.24±0.44 | 66.62±5.11 | Q327E | 2.43±0.23 | 11.30±2.06 |
| N215S | 2.55±0.34 | 4.25±0.87 | G328A | 18.54±5.39 | 13.56±1.82 |
| I219N | 13.22±0.64 | 167.06±66.53 | E338K | 4.37±0.15 | 16.27±4.34 |
| N224S | 2.57±0.14 | 6.34±1.84 | W340R | 10.13±1.50 | 103.46±37.51 |
| H225R | 27.40±1.84 | 859.83±134.62 | E341D | 2.86±0.11 | 16.83±3.83 |
| D234E | 13.64±3.01 | 341.35±47.17 | R342Q | 4.03±1.45 | 15.70±6.79 |
| I242N | 12.02±0.70 | 9.29±1.05 | S345P | 8.15±0.61 | 76.21±4.89 |
| L243F | 8.36±0.67 | 9.86±1.51 | A348P | 1.60±0.03 | 4.75±2.29 |
| D244N | 4.05±1.47 | 3.50±1.26 | I354K | 18.89±3.89 | 17.20±2.91 |
| D244H | 3.17±0.97 | 1.24±0.42 | R356W | 2.78±0.57 | 0.95±0.09 |
| P259R | 3.31±0.42 | 2.10±0.49 | E358K | 2.81±0.57 | 400.63±117.46 |
| P259L | 8.40±2.98 | 9.04±0.51 | R363H | 1.71±0.13 | 0.98±0.39 |
| G260A | 8.47±2.58 | 12.29±1.04 | R363C | 2.33±0.28 | 2.08±0.92 |
| N263S | 4.77±1.19 | 2.49±0.35 | G373D | 3.22±0.42 | 5.43±2.58 |
| D264Y | 13.15±3.23 | 18.24±3.73 | G373S | 2.64±0.42 | 2.24±0.69 |
| P265R | 12.61±1.21 | 96.58±26.62 | E398K | 1.28±0.03 | 6.94±2.43 |
| P265L | 2.74±0.20 | 1.10±0.07 | P409S | 14.45±1.75 | 2.67±0.61 |

Fig. 2C: DGJ-Responsive Mutations described in Figure 1C: Potency and Response Magnitude

Fig. 6

| α-Gal A mutation | Primer | α-Gal A mutation | Primer |
|---|---|---|---|
| GLA-M1I-5' | CGTGACAATACAGCTGAG | GLA-R227Q-3' | GTCAGCAAAATTTTGCCAGTGATTGC |
| GLA-M1I-3' | CTCAGCTGTATTGTCACG | GLA-A230T-5' | gcgaaatttt actgacattgatg |
| GLA-M1T-5 | CACCGTGACA ACG CAGCTGAGG | GLA-A230T-3' | CAT CAA TGT CAG TAA AAT TTC GC |
| GLA-M1T-3 | CCT CAG CTG CGT TGT CAC GGT G | GLA-D231N-5 | GGCGAAATTTTGCT aAC ATTGATGATTCCTG |
| GLA-L14P-5' | GGCTGCGCGCCTGCGCTTCG | GLA-D231N-3 | CAG GAA TCA TCA ATG TTA GCA AAA TTT CGC C |
| GLA-L14P-3' | CGAAGCGCAGGCGCGCAGCC | GLA-D231G-5' | CGAAATTTTGCT GgC ATTGATGATATTC |
| GLA-L16P/H-5' | GCGCTTGCGCMTCGCTTCCTGG | GLA-D231G-3' | GAA TAT CAT CAA TGC CAG CAA AAT TTC G |
| GLA-L16P/H-3' | CCAGGAAGCGAKGCGCAAGCGC | GLA-D234E-5' | tgacattgat gag tcctggaaaag |
| GLA-L19P-5' | GCTTCGCTTCCCGGCCCTCGTTTC | GLA-D234E-3' | CTT TTC CAG GAC TCA TCA ATG TCA |
| GLA-L19P-3' | GAAACGAGGGCCGGGAAGCGAAGC | GLA-D234Y-5 | GCTGACATTGAT tAT TCCTGGAAAAG |
| GLA-A31V-5' | GGGGCTAGAGTACTGGACAATGG | GLA-D234Y-3 | CTT TTC CAG GAA TAA TCA ATG TCA GC |
| GLA-A31V-3' | CCATTGTCCAGTACTCTAGCCCC | GLA-S235C-5 | CTGACATTGATGAT TgC TGGAAAAGTATAAAGAG |
| GLA-L32P-5' | GCTAGAGCACCGGACAATGGA | GLA-S235C-3 | CTC TTT ATA CTT TTC CAG CAA TCA TCA ATG TCA G |
| GLA-L32P-3' | TCCATTGTCCGGTGCTCTAGC | GLA-W236R-5 | GCTGACATTGATGATTCC cGG AAAAGTATAAAGAGTATC |
| GLA-L32P-5' | GCTAGAGCACCGGACAATGGA | GLA-W236R-3 | GAT ACT CTT TAT ACT TTT CCG GGA ATC ATC AAT GTC AGC |
| GLA-L32P-3' | TCCATTGTCCGGTGCTCTAGC | GLA-W236L-5' | TGATGATTCC TTG AAAAGTATAA |
| GLA-D33Y-5' | CTAGAGCACTGTACAATGGATTG | GLA-W236L-3' | TTA TAC TTT TCA AGG AAT CAT CA |
| GLA-D33Y-3' | CAATCCATTGTACAGTGCTCTAG | GLA-W236L-5 | ctGACATTGATGATTCC TtG AAAAGTATAAAGAG |
| GLA-N34K-5' | GCACTGGACAAAGGATTGGC | GLA-W236L-3 | CTC TTT ATA CTT TTC AAG GAA TCA TCA ATG TCA G |
| GLA-N34K-3' | GCCAATCCTTTGTCCAGTGC | GLA-W236C-5 | GCTGACATTGATGATTCC TGt AAAAGTATAAAGAGTATCT TGG |
| GLA-N34S-5' | GCACTGGACAGTGGATTGGC | GLA-W236C-3 | CCA AGA TAC TCT TTA TAC TTT TAC AGG AAT CAT CAA TGT CAG C |
| GLA-N34S-3' | GCCAATCCACTGTCCAGTGC | GLA-I239T-5' | TGGAAAAGT ACA AAGAGTATC |

Fig. 6 (Cont.)

| GLA-G35R-5' | CTGGACAATAGATTGGCAAGG | GLA-I239T-3' | GAT ACT CTT TGT ACT TTT CCA |
|---|---|---|---|

Fig. 6 (Cont.)

| | | | |
|---|---|---|---|
| GLA-G35R-3' | CCTTGCCAATCTATTGTCCAG | GLA-I239T-5 | GATTCCTGGAAAAGT AcA AAGAGTATCTTGGACTG |
| GLA-A37V-5' | AATGGATTGGTAAGGACGCC | GLA-I239T-3 | CAG TCC AAG ATA CTC TTT GTA CTT TTC CAG GAA TC |
| GLA-A37V-3' | GGCGTCCTTACCAATCCATT | GLA-I242F-5' | AGTATAAAGAGT TTC TTGGACTGGAC |
| GLA-P40L-5' | GCAAGGACGCTTACCATGGG | GLA-I242F-3' | GTC CAG TCC AAG AAA CTC TTT ATA CT |
| GLA-P40L-3' | CCCATGGTAAGCGTCCTTGC | GLA-I242N-5' | GTATAAAGAGT AAC TTGGACTGG |
| GLA-P40S-5' | GCAAGGACGTCTACCATGGG | GLA-I242N-3' | CCA GTC CAA GTT ACT CTT TAT AC |
| GLA-P40S-3' | CCCATGGTAGACGTCCTTGC | GLA-L243F-5' | AGAGTATCTTCGACTGGACATC |
| GLA-M42T-5 | AGGACGCCTACC AcG GGCTGGCTGCAC | GLA-L243F-3' | GAT GTC CAG TCG AAG ATA CTC T |
| GLA-M42T-3 | GTG CAG CCA GCC CGT GGT AGG CGT CCT | GLA-D244H-5' | GAGTATCTTG CACTGGACATC |
| GLA-M42L-5 | AGGACGCCTACC TTG GGCTGGCTGCAC | GLA-D244H-3' | GAT GTC CAG TCG AAG ATA CTC T |
| GLA-M42L-3 | GTG CAG CCA GCC CAA GGT AGG CGT CCT | GLA-S247C-5' | CTTGGACTGGACATGTTTTAACCAGG AGAG |
| GLA-M42V-5 | AGGACGCCTACC GTG GGCTGGCTGC | GLA-S247C-3' | CTC TCC TGG TTA AAA CAT GTC CAG TCC AAG |
| GLA-M42V-3 | GCA GCC AGC CCA CGG TAG GCG TCC T | GLA-S247P-5' | GGACTGGACA CCTTTTAACCA |
| GLA-G43D/V-5' | CTACCATGGWCTGGCTGCAC | GLA-S247P-3' | TGG TTA AAA GGT GTC CAG TCC |
| GLA-G43D/V-3' | GTGCAGCCAGWCCATGGTAG | GLA-A257P-5' | GTTGATGTT CCTGGACCAG |
| GLA-G43R-5' | CTACCATGCGCTGGCTGCAC | GLA-A257P-3' | CTG GTC CAG GAA CAT CAA C |
| GLA-G43R-3' | GTGCAGCCAGCGCATGGTAG | GLA-G258R-5' | GATGTTGCT CGACCAGGGG |
| GLA-W44C-5' | CATGGGCTGTCTGCACTGG | GLA-G258R-3' | CCC CTG GTC GAG CAA CAT C |
| GLA-W44C-3' | CCAGTGCAGACAGCCCATG | GLA-P259R-5' | GATGTTGCTGGACGAGGGGGTTGGA |
| GLA-L45R-5' | ATGGGCTGGCGGCACTGGGAG | GLA-P259R-3' | TCCAACCCCCTCGTCCAGCAACATC |
| GLA-L45R-3' | CTCCCAGTGCCGCCAGCCCAT | GLA-P259L-5' | GTTGCTGGACTAGGGGGTTGG |
| GLA-H46R-5' | CTGGCTGCGCTGGGAGC | GLA-P259L-3' | CCA ACC CCC TAG TCC AGC AAC |
| GLA-H46R-3' | GCTCCCAGCGCAGCCAG | GLA-G260A-5' | GCTGGACCA GCG GGTTGGAATG |
| GLA-H46Y-5' | CTGGCTGTACTGGGAGC | GLA-G260A-3' | CAT TCC AAC CCG CTG GTC CAG C |
| GLA-H46Y-3' | GCTCCCAGTACAGCCAG | GLA-G261D-5' | GGACCAGGG GAT TGGAATGAC |

Fig. 6 (Cont.)

| | | | |
|---|---|---|---|
| GLA-W47G-5' | CTGGCTGCACGGGGAGCGCTTC | GLA-G261D-3' | GTC ATT CCA ATC CCC TGG TCC |
| GLA-W47G-3' | GAAGCGCTCCCCGTGCAGCCAG | GLA-W262C-5' | CAGGGGGT TGC AATGACCCAG |
| GLA-W47L-5' | CTGGCTGCACTTGGAGCGCTTC | GLA-W262C-3' | CTG GGT CAT TGC AAC CCC CTG |
| GLA-W47L-3' | GAAGCGCTCCAAGTGCAGCCAG | GLA-N263S-5' | GGGGTTGG AGT GACCCAGA |
| GLA-E48K-5' | GCTGCACTGGAAGCGCTTCATG | GLA-N263S-3' | TCT GGG TCA CTC CAA CCC C |
| GLA-E48K-3' | CATGAAGCGCTTCCAGTGCAGC | GLA-D264V-5' | GGTTGGAAT GTC CCAGATATG |
| GLA-R49P/L-5' | ACTGGGAGCYCTTCATGTGC | GLA-D264V-3' | CAT ATC TGG GAC ATT CCA ACC |
| GLA-R49P/L-3' | GCACATGAAGRGCTCCCAGT | GLA-D264Y-5' | GGGTTGGAAT TAC CCAGATATG |
| GLA-R49S/G-5' | CACTGGGAGRGCTTCATGT | GLA-D264Y-3' | CAT ATC TGG GTA ATT CCA ACC C |
| GLA-R49S/G-3' | ACATGAAGCYCTCCCAGTG | GLA-P265R-5' | TGGAATGAC CGA GATATGTTA |
| GLA-F50C-5' | CTGGGAGCGCTGCATGTGCAAC | GLA-P265R-3' | TAA CAT ATC TCG GTC ATT CCA |
| GLA-F50C-3' | GTTGCACATGCAGCGCTCCCAG | GLA-P265L-5' | TTGGAATGAC CTA GATATGTTAG |
| GLA-M51K-3' | GAGCGCTTCAAGTGCAACCTTG | GLA-P265L-3' | CTA ACA TAT CTA GGT CAT TCC AA |
| GLA-M51K-5' | CAAGGTTGCACTTGAAGCGCTC | GLA-D266N/H-5' | GGAATGACCCA mAT ATGTTAGTG |
| GLA-M51I-5' | GCGCTTCATATGCAACC | GLA-D266N/H-3' | CAC TAA CAT ATT GGG TCA TTC C |
| GLA-M51I-3' | GGTTGCATATGAAGCGC | GLA-D266H-5 | GGTTGGAATGACCCA cAT ATGTTAGTGATTGG |
| GLA-C52S-5' | GAGCGCTTCATGTCCAACCTTGACTG | GLA-D266H-3 | CCA ATC ACT AAC ATA TGT GGG TCA TTC CAA CC |
| GLA-C52S-3' | CAGTCAAGGTTGGACATGAAGCGCTC | GLA-D266V-5' | GAATGACCCA GTT ATGTTAGTG |
| GLA-C52G/R-5' | CGCTTCATGSGCAACCTTGAC | GLA-D266V-3' | CAC TAA CAT AAC TGG GTC ATT C |
| GLA-C52G/R-3' | GTCAAGGTTGCSCATGAAGCG | GLA-D266E-5' | ATGACCCA GAA ATGTTAGTGA |
| GLA-C56G-5' | CAACCTTGACGGCCAGGAAG | GLA-D266E-3' | TCA CTA ACA TTT CTG GGT CAT |
| GLA-C56G-3' | CTTCCTGGCCGTCAAGGTTG | GLA-M267R-5' | GACCCAGAT AGG TTAGTGATTG |
| GLA-C56Y/F-5' | CAACCTTGACTWCCAGGAAGAG | GLA-M267R-3' | CAA TCA CTA ACC TAT CTG GGT C |
| GLA-C56Y/F-3' | CTCTTCCTGGWAGTCAAGGTTG | GLA-M267I-5' | GACCCAGAT ATA TTAGTGATTGG |
| GLA-C56Y-5 | GTGCAACCTTGACTACCAGGAAGAGCCAG | GLA-M267I-3' | CCA ATC ACT AAT ATA TCT GGG TC |

Fig. 6 (Cont.)

| | | | |
|---|---|---|---|
| GLA-C56Y-3 | CTG GCT CTT CCT GGT AGT CAA GGT TGC AC | GLA-L268S-5' | CCA GAT ATG TCA GTG ATT GGC |
| GLA-C63Y-5 | gaGCCAGATTCC TAC ATCAGTGAGAagc | GLA-L268S-3' | GCC AAT CAC TGA CAT ATC TGG |
| GLA-C63Y-3 | GCT TCT CAC TGA TGT AGG AAT CTG GCT C | GLA-V269A-5' | gatatgtta gcg attggcaac |
| GLA-S65T-5' | TCCTGCATCACTGAGAAGCTC | GLA-V269A-3' | GTT GCC AAT CGC TAA CAT ATC |
| GLA-S65T-3' | GAGCTTCTCAGTGATGCAGGA | GLA-V269M-5' | CAG ATA TGT TAA TGA TTG GCA AC |
| GLA-E66K-5' | CTGCATCAGTAAGAAGCTCTTC | GLA-V269M-3' | GTT GCC AAT CAT TAA CAT ATC TG |
| GLA-E66K-3' | GAAGAGCTTCTTACTGATGCAG | GLA-I270T-5' | TATGTTAGTGA C TGGCAACTTTG |
| GLA-E66G-5' | CTGCATCAGTGGGAAGCTCTTC | GLA-I270T-3' | CAA AGT TGC CAG TCA CTA ACA TA |
| GLA-E66G-3' | GAAGAGCTTCCCACTGATGCAG | GLA-G271V-5' | TTAGTGATTGTCAACTTTG |
| GLA-L68F-5' | CAGTGAGAAGTTCTTCATGG | GLA-G271V-3' | CAAAGTTGACAATCACTAA |
| GLA-L68F-3' | CCAGGAAGAACTTCTCACTG | GLA-G271C-5' | GTTAGTGATT T GCAACTTTGG |
| GLA-L68F-5 | GCATCAGTGAGAAG tTC TTCATGGAGATG | GLA-G271C-3' | CCA AAG TTG CAA ATC ACT AAC |
| GLA-L68F-3 | CAT CTC CAT GAA GAA CTT CTC ACT GAT GC | GLA-G271S-5' | TGTTAGTGATT A GCAACTTTGGC |
| GLA-M72R-5' | CTTCATGGAGAGGGCAGAGCTC | GLA-G271S-3' | GCC AAA GTT GCT AAT CAC TAA CA |
| GLA-M72R-3' | GAGCTCTGCCCTCTCCATGAAG | GLA-N272K-5' | GTGATTGGC AAA TTTGGCCTCAG |
| GLA-M72I-5' | CTTCATGGAGATAGCAGAGCTC | GLA-N272K-3' | CTG AGG CCA AAT TTG CCA ATC AC |
| GLA-M72I-3' | GAGCTCTGCTATCTCCATGAAG | GLA-N272S-5' | GTGATTGGC AGC TTTGGCCTC |
| GLA-A73V-5' | CATGGAGATGGTAGAGCTCATG | GLA-N272S-3' | GAG GCC AAA GCT GCC AAT CAC |
| GLA-A73V-3' | CATGAGCTCTACCATCTCCATG | GLA-S276G-5' | CAACTTTGGCCTCGGCTGGAATCAG |
| GLA-M76R-5' | GCAGAGCTCAGGGTCTCAGAAG | GLA-S276G-3' | CTGATTCCAGCCGAGGCCAAAGTTG |
| GLA-M76R-3' | CTTCTGAGACCCTGAGCTCTGC | GLA-S276N-5' | CTTTGGCCTC AAC TGGAATCAGC |
| GLA-W81C-5' | CTCAGAAGGC TGt AAGGATGCAGGT | GLA-S276N-3' | GCT GAT TCC AGT TGA GGC CAA AG |
| GLA-W81C-3' | ACC TGC ATC CTT ACA GCC TTC TGA G | GLA-Q279R-5' | AGCTGGAAT CGG CAAGTAACTC |
| GLA-W81S-5' | CTCAGAAGGCTCGAAGGATGCA | GLA-Q279R-3' | GAG TTA CTT GCC GAT TCC AGC T |
| GLA-W81S-3' | TGCATCCTTCGAGCCTTCTGAG | GLA-Q279H-5' | CAGCTGGAAT CAC CAAGTAACTC |

Fig. 6 (Cont.)

| | | | |
|---|---|---|---|
| GLA-G85D-5' | GAAGGATGCAGATTATGAGTAC | GLA-Q279H-3' | GAG TTA CTT GGT GAT TCC AGC TG |
| GLA-G85D-3' | GTACTCATAATCTGCATCCTTC | GLA-Q279K-5' | CAGCTGGAAT AAG CAAGTAAC |
| GLA-Y86C-5 | GGATGCAGGT TGT GAGTACCTCTGc | GLA-Q279K-3' | GTT ACT TGC TTA TTC CAG CTG |
| GLA-Y86C-3 | GCA GAG GTA CTC ACA ACC TGC ATC C | GLA-Q280H-5' | GGAATCAGCAT GTAACTCAGA |
| GLA-Y88D-5' | GGTTATGAGGACCTCTGCATTG | GLA-Q280H-3' | TCT GAG TTA CAT GCT GAT TCC |
| GLA-Y88D-3' | CAATGCAGAGGTCCTCATAACC | GLA-Q280K-5' | CTGGAATCAG AAA GTAACTCAG |
| GLA-L89P/R-5' | GTTATGAGTACCSCTGCATTGATG | GLA-Q280K-3' | CTG AGT TAC TTT CTG ATT CCA |
| GLA-L89P/R-3' | CATCAATGCAGSGGTACTCATAAC | GLA-T282N-5' | CAGCAAGTAAATCAGATGGCC |
| GLA-D92N/H/Y-5' | CCTCTGCATTHATGACTGTTG | GLA-T282N-3' | GGC CAT CTG ATT TAC TTG CTG |
| GLA-D92N/H/Y-3' | CAACAGTCATDAATGCAGAGG | GLA-Q283P-5' | CAAGTAACT CCG ATGGCCCTC |
| GLA-D92N-5' | TACCTCTGCATT AAT GACTGTTGGATG | GLA-Q283P-3' | GAG GGC CAT CGG AGT TAC TTG |
| GLA-D92N-3' | CAT CCA ACA GTC ATT AAT GCA GAG GTA | GLA-M284T-5' | GTAACTCAG ACG GCCCTCTG |
| GLA-D92H-5' | TACCTCTGCATT CAT GACTGTTGGATG | GLA-M284T-3' | CAG AGG GCC GTC TGA GTT AC |
| GLA-D92H-3' | CAT CCA ACA GTC ATG AAT GCA GAG GTA | GLA-A285P-5' | TAACTCAGATG C CCCTCTGGGCT |
| GLA-D92Y-5 | GAGTACCTCTGCATT tAT GACTGTTGGATGGCTC | GLA-A285P-3' | AGC CCA GAG GGG CAT CTG AGT TA |
| GLA-D92Y-3 | GAG CCA TCC AAC AGT CAT AAA TGC AGA GGT ACT C | GLA-A285D-5' | AACTCAGATGG A CCTCTGGGCT |
| GLA-D93G-5' | CTGCATTGATGGCTGTTGGATG | GLA-A285D-3' | AGC CCA GAG GTC CAT CTG AGT T |
| GLA-D93G-3' | CATCCAACAGCCATCAATGCAG | GLA-W287G-5' | GATGGCCCTC GGG GCTATCAT |
| GLA-D93V-5' | CTGCATTGATGTCTGTTGGATG | GLA-W287G-3' | ATG ATA GCC CCG AGG GCC ATC |
| GLA-D93V-3' | CATCCAACAGACATCAATGCAG | GLA-W287C-5' | ATGGCCCTC TGT GCTATCATG |
| GLA-D93N-5' | CTGCATTGATAACTGTTGGATG | GLA-W287C-3' | CAT GAT AGC ACA GAG GGC CAT |
| GLA-D93N-3' | CATCCAACAGTTATCAATGCAG | GLA-A288D-5' | GCCCTCTGG GAT ATCATGGCTG |
| GLA-C94S-5' | GCATTGATGACTCTTGGATGGCTC | GLA-A288D-3' | CAG CCA TGA TAT CCC AGA GGG C |
| GLA-C94S-3' | GAGCCATCCAAGAGTCATCAATGC | GLA-A288P-5' | GCCCTCTGG CCT ATCATGG |

Fig. 6 (Cont.)

| | | | |
|---|---|---|---|
| GLA-C94Y-5' | GCATTGATGACTATTGGATGGCTC | GLA-A288P-3' | CCA TGA TAG GCC AGA GGG C |
| GLA-C94Y-3' | GAGCCATCCAATAGTCATCAATGC | GLA-I289F-5' | CTCTGGGCT TTC ATGGCTGCTCCTT |
| GLA-W95S-5' | GATGACTGTTCGATGGCTCCC | GLA-I289F-3' | AAG GAG CAG CCA TGA AAG CCC AGA G |
| GLA-W95S-3' | GGGAGCCATCGAACAGTCATC | GLA-M290I-5' | GGGCTATC ATC GCTGCTCCTT |
| GLA-A97P-5' | CTGTTGGATGCCTCCCCAAAGAG | GLA-M290I-3' | AAG GAG CAG CGA TGA TAG CCC |
| GLA-A97P-3' | CTCTTTGGGGAGGCATCCAACAG | GLA-A292P-5' | CTATCATGGCT CCT CCTTTATTC |
| GLA-R100K/T-5' | GCTCCCCAAAMAGATTCAGAAG | GLA-A292P-3' | GAA TAA AGG AGG AGC CAT GAT AG |
| GLA-R100K/T-3' | CTTCTGAATCTKTTTGGGGAGC | GLA-P293A-5' | CATGGCTGCT GCT TTATTCATG |
| GLA-R100T-5' | GGCT CCC CAA ACA GAT TCA GAA GG | GLA-P293A-3' | CAT GAA TAA AGC AGC AGC CAT G |
| GLA-R100T-3' | CCT TCT GAA TCT GTT TGG GGA GCC | GLA-P293S/T-5' | CATGGCTGCT WCT TTATTCATG |
| GLA-E103Q-5' | CAAAGAGATTCACAAGGCAGACTTC | GLA-P293S/T-3' | CAT GAA TAA AGW AGC AGC CAT G |
| GLA-E103Q-3' | GAAGTCTGCCTTGTGAATCTCTTTG | GLA-F295C-5' | GCTGCTCCTTTA TGC ATGTCTAATGACC |
| GLA-R112S-5' | GCAGACCCTCAGAGCTTTCCTCATG | GLA-F295C-3' | GGT CAT TAG ACA TGC ATA AAG GAG CAG C |
| GLA-R112S-3' | CATGAGGAAAGCTCTGAGGGTCTGC | GLA-S297C/F-5' | CTTTATTCATG TKT AATGACCTCCG |
| GLA-R112C-5' | CAGACCCTCAGTGCTTTCCTCATG | GLA-S297C/F-3' | CGG AGG TCA TTA MAC ATG AAT AAA G |
| GLA-R112C-3' | CATGAGGAAAGCACTGAGGGTCTG | GLA-N298S-5' | ATTCATGTCT AGT GACCTCCGAC |
| GLA-F113S-5' | CCCTCAGCGCTCTCCTCATG | GLA-N298S-3' | GTC GGA GGT CAC TAG ACA TGA AT |
| GLA-F113S-3' | CATGAGGAGAGCGCTGAGGG | GLA-N298K-5' | TATTCATGTCTAAGGACCTCCGAC |
| GLA-R118C-5' | CTCATGGGATTTGCCAGCTAGC | GLA-N298K-3' | GTCGGAGGTCCTTAGACATGAATA |
| GLA-R118C-3' | GCTAGCTGGCAAATCCCATGAG | GLA-N298H-5' | TATTCATGTCT cAT GACCTCCGAC |
| GLA-L120P-5' | GATTCGCCAGCCAGCTAATTATG | GLA-N298H-3' | GTC GGA GGT CAT GAG ACA TGA ATA |
| GLA-L120P-3' | CATAATTAGCTGGCTGGCGAATC | GLA-D299G-5' | TCATGTCTAAT GGC CTCCGACACATC |
| GLA-A121P/T-5' | TC GCC AGC TAM CTA ATT ATG TTC ACA GC | GLA-D299G-3' | GAT GTG TCG GAG GCC ATT AGA CAT GA |
| GLA-A121P/T-3' | GCT GTG AAC ATA ATT AGK TAG CTG GCG A | GLA-L300P-5' | GTCTAATGACCCCCGACACATCAG |
| GLA-V124D-5' | GCTAGCTAATTAT GaT CACAGCAAAGGAC | GLA-L300P-3' | CTGATGTGTCGGGGGTCATTAGAC |

Fig. 6 (Cont.)

| | | | |
|---|---|---|---|
| GLA-V124D-3' | GTC CTT TGC TGT GAT CAT AAT TAG CTA GC | GLA-L300F-5' | GTCTAATGACTTCCGACACATC |
| GLA-G128E-5' | CACAGCAAAGaACTGAAGCTAG | GLA-L300F-3' | GATGTGTCGGAAGTCATTAGAC |
| GLA-G128E-3' | CTA GCT TCA GTT CTT TGC TGT G | GLA-L300H-5' | GTCTAATGACCACCGACACATC |
| GLA-L129P-5' | CAG CAA AGG ACC GAA GCT AGG | GLA-L300H-3' | GATGTGTCGGTGGTCATTAGAC |
| GLA-L129P-3' | ATC CCT AGC TTC GGT CCT TTG CTG | GLA-R301G-5' | CTAATGACCTCGGACACATCAGC |
| GLA-L131P-5' | AGGACTGAAGC C AGGGATTTATGC | GLA-R301G-3' | GCTGATGTGTCCGAGGTCATTAG |
| GLA-L131P-3' | GCA TAA ATC CCT GGC TTC AGT CCT | GLA-R301P-5' | CTAATGACCTCCCACACATCAGC |
| GLA-G132E-5' | GGACTGAAGCTA GaG ATTTATGCAGATG | GLA-R301P-3' | GCTGATGTGTGGGAGGTCATTAG |
| GLA-G132E-3' | CAT CTG CAT AAA TCT CTA GCT TCA GTC C | GLA-I303N-5' | CTCCGACACAACAGCCCTCAAGC |
| GLA-G132R-5' | GAC TGA AGC TAA GGA TTT ATG CAG ATG | GLA-I303N-3' | GCTTGAGGGCTGTTGTGTCGGAG |
| GLA-G132R-3' | CAT CTG CAT AAA TCC TTA GCT TCA GTC | GLA-L310F-5' | GCCAAAGCTTTCCTTCAGGA |
| GLA-Y134S-5' | GCT AGG GAT TTC TGC AGA TGT TGG | GLA-L310F-3' | TCCTGAAGGAAAGCTTTGGC |
| GLA-Y134S-3' | CCA ACA TCT GCA GAA ATC CCT AGC | GLA-Q312H-5' | GCTCTCCTTCACGATAAGGACG |
| GLA-A135V-5' | GCT AGG GAT TTA TGT AGA TGT TGG A | GLA-Q312H-3' | CGTCCTTATCGTGAAGGAGAGC |
| GLA-A135V-3' | TCC AAC ATC TAC ATA AAT CCC TAG C | GLA-D313Y-5' | CTCTCCTTCAGTATAAGGACG |
| GLA-D136H-5' | GGA TTT ATG CAC ATG TTG GAA | GLA-D313Y-3' | CGTCCTTATACTGAAGGAGAG |
| GLA-D136H-3' | TTC CAA CAT GTG CAT AAA TCC | GLA-V316E-5' | GATAAGGACGAAATTGCCATC |
| GLA-D136H-5 | GGGATTTATGCA cAT GTTGGAAATAA AACC | GLA-V316E-3' | GATGGCAATTTCGTCCTTATC |
| GLA-D136H-3 | GGT TTT ATT TCC AAC ATG TGC ATA AAT CCC | GLA-I317N/T-5' | AAGGACGTAAMTGCCATCAATC |
| GLA-G138E-5' | TGC AGA TGT TGA AAA TAA AAC CTG | GLA-I317N/T-3' | GATTGATGGCAKTTACGTCCTT |
| GLA-G138E-3' | CAG GTT TTA TTT TCA ACA TCT GCA | GLA-N320I-5' | AATTGCCATCATTCAGGACCCC |
| GLA-G138R-5' | TGC AGA TGT TAG AAA TAA AAC CTG | GLA-N320I-3' | GGGGTCCTGAATGATGGCAATT |
| GLA-G138R-3' | CAG GTT TTA TTT CTA ACA TCT GCA | GLA-N320K-5' | AATTGCCATCAAGCAGGACCCC |
| GLA-G138E-5 | GGATTTATGCAGATGTT GaA AATAAAACCTGCGCAGC | GLA-N320K-3' | GGGGTCCTGCTTGATGGCAATT |
| GLA-G138E-3 | GCT GCG CAG GTT TTA TTT TCA ACA TCT GCA TAA ATC C | GLA-N320Y-5' | AATTGCCATCTATCAGGACCCC |

Fig. 6 (Cont.)

| | | | |
|---|---|---|---|
| GLA-G138R-5 | GGATTTATGCAGATGTT cGA AATAAAACCTGCGCAGC | GLA-N320Y-3' | GGGGTCCTGATAGATGGCAATT |
| GLA-G138R-3 | GGA TTT ATG CAG ATG TTC GAA ATA AAA CCT GCG CAG C | GLA-Q321E-5' | TGCCATCAATGAGGACCCCTTG |
| GLA-T141I-5' | GGA AAT AAA ATC TGC GCA GGC T | GLA-Q321E-3' | CAAGGGGTCCTCATTGATGGCA |
| GLA-T141I-3' | AGC CTG CGC AGA TTT TAT TTC C | GLA-Q321R-5' | TGCCATCAATCGGGACCCCTTG |
| GLA-C142R-5' | GGA AAT AAA ACC CGC GCA GGC TTC | GLA-Q321R-3' | CAAGGGGTCCCGATTGATGGCA |
| GLA-C142R-3' | GAA GCC TGC GCG GGT TTT ATT TCC | GLA-G325D-5' | GGACCCCTTGGACAAGCAAG |
| GLA-C142Y/W-5' | GA AAT AAA ACC TRC GCA GGC TTCC | GLA-G325D-3' | CTTGCTTGTCCAAGGGGTCC |
| GLA-C142Y/W-3' | GGA AGC CTG CGY AGG TTT TAT TTC | GLA-Q327K/E-5' | CTTGGGCAAGRAAGGGTACCAG |
| GLA-C142W-5 | GGAAATAAAACCTGGGCAGGCTTCCCTG | GLA-Q327K/E-3' | CTGGTACCCTTYCTTGCCCAAG |
| GLA-C142W-3 | CAG GGA AGC CTG CCC AGG TTT TAT TTC C | GLA-G328R-5' | GGCAAGCAAAGGTACCAGC |
| GLA-A143T-5' | GAAATAAAACCTGCACAGGCTTCCC | GLA-G328R-3' | GCTGGTACCTTTGCTTGCC |
| GLA-A143T-3' | GGGAAGCCTGTGCAGGTTTTATTTC | GLA-G328A/V-5' | GGCAAGCAAGYGTACCAGC |
| GLA-A143P-5' | ATAAAACCTGC cCA GGCTTCCC | GLA-G328A/V-3' | GCTGGTACRCTTGCTTGCC |
| GLA-A143P-3' | GGG AAG CCT GgG CAG GTT TTA T | GLA-G328E-5' | TGGGCAAGCAA GAG TACCAGCTTAG |
| GLA-G144V-5' | CCT GCG CAG TCT TCC CTG G | GLA-G328E-3' | CTA AGC TGG TAC TCT TGC TTG CCC A |
| GLA-G144V-3' | CCA GGG AAG ACT GCG CAG G | GLA-E338K-5' | GAGACAACTTTAAAGTGTGGG |
| GLA-G147R-5' | GGC TTC CCT AGG AGT TTT Gg | GLA-E338K-3' | CCCACACTTTAAAGTTGTCTC |
| GLA-G147R-3' | cCAA AAC TCC TAG GGA AGC C | GLA-W340R-5' | CTTTGAAGTGCGGGAACGAC |
| GLA-S148N-5' | TTC CCT GGG AAT TTT GGA TAC | GLA-W340R-3' | GTCGTTCCCGCACTTCAAAG |
| GLA-S148N-3' | GTA TCC AAA ATT CCC AGG GAA | GLA-E341D-5' | GAAGTGTGGGACCGACCTCTCTC |
| GLA-S148R-5' | C CCT GGG AGG TTT GGA TACT | GLA-E341D-3' | GAGAGAGGTCGGTCCCACACTTC |
| GLA-S148R-3' | AGT ATC CAA ACC TCC CAG GG | GLA-E341K-5' | GAAGTGTGGAAACGACCTCTCTC |
| GLA-Y152C-5' | GTTTTGGATACTGCGACATTGATG | GLA-E341K-3' | GAGAGAGGTCGTTTCCACACTTC |
| GLA-Y152C-3' | CATCAATGTCGCAGTATCCAAAAC | GLA-R342Q-5' | GTGTGGGAACAACCTCTCTCAG |

Fig. 6 (Cont.)

| | | | |
|---|---|---|---|
| GLA-D155H-5' | CTACGACATT C ATGCCCAGAC | GLA-R342Q-3' | CTGAGAGAGGTTGTTCCCACAC |
| GLA-D155H-3' | GTC TGG GCA TGA ATG TCG TAG | GLA-L344P-5' | GAACGACCTCCCTCAGGCTTAG |
| GLA-A156T-5' | GACATTGAT ACC CAGACCTTtg | GLA-L344P-3' | CTAAGCCTGAGGGAGGTCGTTC |
| GLA-A156T-3' | CAA AGG TCT GGG TAT CAA TGT C | GLA-S345P-5' | CGACCTCTCCCAGGCTTAGCC |
| GLA-W162R-5' | CTTTGCTGACCGGGGAGTAGATC | GLA-S345P-3' | GGCTAAGCCTGGGAGAGGTCG |
| GLA-W162R-3' | GATCTACTCCCCGGTCAGCAAAG | GLA-A348P-5' | CTCAGGCTTACCCTGGGCTGTAG |
| GLA-W162C-5' | CTTTGCTGACTGCGGAGTAGATC | GLA-A348P-3' | CTACAGCCCAGGGTAAGCCTGAG |
| GLA-W162C-3' | GATCTACTCCGCAGTCAGCAAAG | GLA-A350P-5' | CTTAGCCTGGCCTGTAGCTATG |
| GLA-G163V-5' | GCTGACTGGGTAGTAGATCTG | GLA-A350P-3' | CATAGCTACAGGCCAGGCTAAG |
| GLA-G163V-3' | CAGATCTACTACCCAGTCAGC | GLA-A352D-5' | CTGGGCTGTAGATATGATAAAC |
| GLA-D165V-5' | CTGGGGAGTAGTTCTGCTAAAATTTG | GLA-A352D-3' | GTTTATCATATCTACAGCCCAG |
| GLA-D165V-3' | CAAATTTTAGCAGAACTACTCCCCAG | GLA-I354K-5' | GTAGCTATGAAAAACCGGCAGG |
| GLA-L167P-5' | GAGTAGATCTGC C AAAATTTGATGG | GLA-I354K-3' | CCTGCCGGTTTTTCATAGCTAC |
| GLA-L167P-3' | CCA TCA AAT TTT GGC AGA TCT ACT C | GLA-N355K-5' | GCTATGATAAAACGGCAGGAG |
| GLA-K168R-5' | GTAGATCTGCTA AGA TTTGATGGTTG | GLA-N355K-3' | CTCCTGCCGTTTTATCATAGC |
| GLA-K168R-3' | CAA ACC ATC AAA TCT TAG CAG ATC TAC | GLA-R356W-5' | GCTATGATAAACTGGCAGGAGATT |
| GLA-F169S-5 | gtaGATCTGCTAAAA TCT GATGGTTGTTACtg | GLA-R356W-3' | AATCTCCTGCCAGTTTATCATAGC |
| GLA-F169S-3 | CAG TAA CAA CCA TCA GAT TTT AGC AGA TCT AC | GLA-E358G/A-5' | ACCGGCAGGGATTGGTGGAC |
| GLA-D170V-5' | GCTAAAATTTG T TGGTTGTTACTG | GLA-E358G/A-3' | GTCCACCAATCSCCTGCCGGT |
| GLA-D170V-3' | CAG TAA CAA CCA ACA AAT TTT AGC | GLA-E358K-5' | GATAAACCGGCAGAAGATTGGTGG |
| GLA-D170H-5' | GCTAAAATTTC AT GGTTGTTACTG | GLA-E358K-3' | CCACCAATCTTCTGCCGGTTTATC |
| GLA-D170H-3' | CAG TAA CAA CCA TGA AAT TTT AGC | GLA-E358A-5 | GATAAACCGGCAG GcG ATTGGTGGACCTC |
| GLA-G171D-5' | CTAAAATTTGAT GAT TGTTACTGTGAC | GLA-E358A-3 | GAG GTC CAC CAA TCG CCT GCC GGT TTA TC |
| GLA-G171D-3' | GTC ACA GTA ACA ATC ATC AAA TTT TAG | GLA-I359T-5' | CCGGCAGGAGACTGGTGGACCTC |
| GLA-G171R-5' | CTAAAATTTGAT CGT TGTTACTGTGAC | GLA-I359T-3' | GAGGTCCACCAGTCTCCTGCCGG |

Fig. 6 (Cont.)

| | | | |
|---|---|---|---|
| GLA-G171R-3' | GTC ACA GTA ACA ACG ATC AAA TTT TAG | GLA-G360S-5' | CAGGAGATTAGTGGACCTCGC |
| GLA-C172Y/F-5' | CTAAAATTTGATGGT TWT tactgtgacagT | GLA-G360S-3' | GCGAGGTCCACTAATCTCCTG |
| GLA-C172Y/F-3' | ACT GTC ACA GTA AWA ACC ATC AAA TTT TAG | GLA-G361R-5' | GGAGATTGGTAGACCTCGCTC |
| GLA-C172W-5' | CTAAAATTTGATGGT TGG tactgtgacagT | GLA-G361R-3' | GAGCGAGGTCTACCAATCTCC |
| GLA-C172W-3' | ACT GTC ACA GTA CCA ACC ATC AAA TTT TAG | GLA-P362L-5' | GATTGGTGGACTTCGCTCTTATAC |
| GLA-C172R-5' | CTAAAATTTGATGGT CGT tactgtgacagT | GLA-P362L-3' | GTATAAGAGCGAAGTCCACCAATC |
| GLA-C172R-3' | ACT GTC ACA GTA ACG ACC ATC AAA TTT TAG | GLA-R363H-5' | GGTGGACCTCACTCTTATAC |
| GLA-C172G-5' | CTAAAATTTGATGGT GGT tactgtgacagT | GLA-R363H-3' | GTATAAGAGTGAGGTCCACC |
| GLA-C172G-3' | ACT GTC ACA GTA ACC ACC ATC AAA TTT TAG | GLA-R363C-5' | GGTGGACCTTGCTCTTATAC |
| GLA-G183D-5' | TTGGCAGATG A TTATAAGCAC | GLA-R363C-3' | GTATAAGAGCAAGGTCCACC |
| GLA-G183D-3' | GTG CTT ATA ATC ATC TGC CAA | GLA-G373R-5' | TGCTTCCCTG CGT AAAGGAGTGG |
| GLA-G183S-5' | TTGGCAGAT A GTTATAAGCAC | GLA-G373R-3' | CCA CTC CTT TAC GCA GGG AAG CA |
| GLA-G183S-3' | GTG CTT ATA ACT ATC TGC CAA | GLA-A377D-5' | GTAAAGGAGTGGACTGTAATCCTG |
| GLA-M187T-5' | GTTATAAGCACA C GTCCTTGGCCCT | GLA-A377D-3' | CAGGATTACAGTCCACTCCTTTAC |
| GLA-M187T-3' | AGG GCC AAG GAC GTG TGC TTA TAA C | GLA-C378Y-5' | AAAGGAGTGGCCTATAATCCTGCC |
| GLA-M187V-5' | GTTATAAGCAC G TGTCCTTGGCC | GLA-C378Y-3' | GGCAGGATTATAGGCCACTCCTTT |
| GLA-M187V-3' | GGC AAA GGA CAC GTG CTT ATA AC | GLA-C378R-5' | AAAGGAGTGGCCCGTAATCCTGCC |
| GLA-L191Q-5' | GTCCTTGGCCCAGAATAGGACTG | GLA-C378R-3' | GGCAGGATTACGGGCCACTCCTTT |
| GLA-L191Q-3' | CAG TCC TAT TCT GGG CCA AGG AC | GLA-C382Y-5' | GTAATCCTGCCTACTTCATCACAC |
| GLA-L191P-5' | GTCCTTGGCCC C GAATAGGACTG | GLA-C382Y-3' | GTGTGATGAAGTAGGCAGGATTAC |
| GLA-L191P-3' | CAG TCC TAT TCG GGG CCA AGG AC | GLA-I384N-5 | CTGCCTGCTTC AaC ACACAGCTCCTC |
| GLA-T194I-5' | CTGAATAGGATTGGCAGAAGC | GLA-I384N-3 | GAG GAG CTG TGT GTT GAA GCA GGC AG |
| GLA-T194I-3' | GCT TCT GCC AAT CCT ATT CAG | GLA-T385P-5' | CCTGCTTCATCCCACAGCTCCTCC |
| GLA-V199M-5' | CAGAAGCATTATGTACTCCTG | GLA-T385P-3' | GGAGGAGCTGTGGGATGAAGCAGG |
| GLA-V199M-3' | CAG GAG TAC ATA ATG CTT CTG | GLA-Q386P-5' | CTTCATCACA CCG CTCCTCCCTGT |

Fig. 6 (Cont.)

| | | | |
|---|---|---|---|
| GLA-S201F-5' | CATTGTGTACTTCTGTGAGTGG | GLA-Q386P-3' | ACA GGG AGG AGC GGT GTG ATG AAG |
| GLA-S201F-3' | CCACTCACAGAAGTACACAATG | GLA-P389R-5' | CACAGCTCCTC CGT GTGAAAAGGAAGCT |
| GLA-S201Y-5' | CATTGTGTACTACTGTGAGTGGC | GLA-P389R-3' | AGC TTC CTT TTC ACA CGG AGG AGC TGT G |
| GLA-S201Y-3' | GCC ACT CAC AGT AGT ACA CAA TG | GLA-F396Y-5' | GGAAGCTAGGGTACTATGAATGG |
| GLA-C202Y-5' | GTG TAC TCC TAT GAG TGG CCT C | GLA-F396Y-3' | CCATTCATAGTACCCTAGCTTCC |
| GLA-C202Y-3' | GAG GCC ACT CAT AGG AGT ACA C | GLA-E398K-5' | AGGGTTCTATAAATGGACTTCA |
| GLA-C202W-5' | GTGTACTCCTGG GAGTGGCCTCT | GLA-E398K-3' | TGAAGTCCATTTATAGAACCCT |
| GLA-C202W-3' | AGA GGC CAC TCC CAG GAG TAC AC | GLA-L403S-5' | GACTTCAAGGTCAAGAAGTCAC |
| GLA-P205T-5' | CTGTGAGTGGACTCTTTATATG | GLA-L403S-3' | GTGACTTCTTGACCTTGAAGTC |
| GLA-P205T-3' | CATATAAAGAGTCCACTCACAG | GLA-I407K-5' | GAAGTCACAAAAATCCCACAG |
| GLA-P205R/L-5' | CTGTGAGTGG CKT CTTTATATG | GLA-I407K-3' | CTGTGGGATTTTTGTGACTTC |
| GLA-P205R/L-3' | CAT ATA AAG AMG CCA CTC ACAG | GLA-P409T/A/S-5' | GTCACATAAATDCCACAGGCACTG |
| GLA-Y207S-5' | TGGCCTCTT TCT ATGTGGCCC | GLA-P409T/A/S-3' | CAGTGCCTGTGGHATTTATGTGAC |
| GLA-Y207S-3' | GGG CCA CAT AGA AAG AGG CCA | GLA-T410K-5' | CACATAAATCCCAAAGGCACTG |
| GLA-Y207C-5' | AGTGGCCTCTT TgT ATGTGGCCCTT | GLA-T410K-3' | CAGTGCCTTTGGGATTTATGTG |
| GLA-Y207C-3' | AAG GGC CAC ATA CAA AGA GGC CAC T | GLA-T410A-5' | CACATAAATCCCGCAGGCACTG |
| GLA-Y216D-5 | CCTTTCAAAAGCCCAAT gAT ACAGAAATCCGACAG | GLA-T410A-3' | CAGTGCCTGCGGGATTTATGTG |
| GLA-Y216D-3 | CTG TCG GAT TTC TGT ATC ATT GGG CTT TTG AAA GG | GLA-G411D-5' | ATCCCACAGACACTGTTTTGC |
| GLA-I219N-5' | CAATTATACAGAA AAC CGACAGTACTGC | GLA-G411D-3' | GCAAAACAGTGTCTGTGGGAT |
| GLA-I219N-3' | GCA GTA CTG TCG GTT TTC TGT ATA ATT G | GLA-L414S-5' | GGCACTGTTTCGCTTCAGCTAG |
| GLA-C223R/G-5' | CGACAGTAC SGC AATCACTGG | GLA-L414S-3' | CTAGCTGAAGCGAAACAGTGCC |
| GLA-C223R/G-3' | CCA GTG ATT GCS GTA CTG TCG | GLA-del20-24aa-5' | GCGCTTCGCTTCCTGGACATCCCTGGGGC |
| GLA-C223Y-5' | CGACAGTACTAC AATCACTGG | GLA-del20-24aa-3' | GCCCCAGGGATGTCCAGGAAGCGAAGCGC |

Fig. 6 (Cont.)

| | | | |
|---|---|---|---|
| GLA-C223Y-3' | CCA GTG ATT GTA GTA CTG TCG | GLA-del113-8aa-5' | GCAGACCCTCAGCGCCAGCTAGCTAATTATG |
| GLA-N224S-5' | CAGTACTGCAGTCACTGGCGA | GLA-del113-8aa-3' | CATAATTAGCTAGCTGGCGCTGAGGGTCTGC |
| GLA-N224S-3' | TCG CCA GTG ACT GCA GTA CTG | GLA-del153aa-5' | GTTTTGGATACTACATTGATGCCCAG |
| GLA-N224D-5' | CAGTACTGCGATCACTGGC | GLA-del153aa-3' | CTGGGCATCAATGTAGTATCCAAAAC |
| GLA-N224D-3' | GCC AGT GAT CGC AGT ACT G | GLA-del205-7aa-5' | CTCCTGTGAGTGGATGTGGCCCTT |
| GLA-H225R-5' | tactgcaat cgc tggcgaaat | GLA-del205-7aa-3' | AAGGGCCACATCCACTCACAGGAG |
| GLA-H225R-3' | ATT TCG CCA GCG ATT GCA GTA | GLA-del254aa-5' | CAGGAGAGAATTGATGTTGCTGG |
| GLA-W226R-5' | gcaatcac cgg cgaaat | GLA-del254aa-3' | CCAGCAACATCAATTCTCTCCTG |
| GLA-W226R-3' | ATT TCG CCG GTG ATT GC | GLA-del358aa-5' | GATAAACCGGCAGATTGGTGGACCT |
| GLA-W226C-5' | gcaatcactgtcgaaatttgc | GLA-del358aa-3' | AGGTCCACCAATCTGCCGGTTTATC |
| GLA-W226C-3' | GCA AAA TTT CGA CAG TGA TTG C | GLA-Ins247-8aa-5' | GACTGGACATCTTGGACATCTTTTAACCAGGAGAG |
| GLA-R227Q-5' | GCAATCACTGGCAAAATTTTGCTGAC | GLA-Ins247-8aa-3' | CTCTCCTGGTTAAAAGATGTCCAAGATGTCCAGTC |

```
GAATTCTCCGGTCACCGTGACAATGCAGCTGAGGAACCCAGAACTACATCTGGGC
TGCGCGCTTGCGCTTCGCTTCCTGGCCCTCGTTTCCTGGGACATCCCTGGGGCTAG
AGCACTGGACAATGGATTGGCAAGGACGCCTACCATGGGCTGGCTGCACTGGGA
GCGCTTCATGTGCAACCTTGACTGCCAGGAAGAGCCAGATTCCTGCATCAGTGAG
AAGCTCTTCATGGAGATGGCAGAGCTCATGGTCTCAGAAGGCTGGAAGGATGCA
GGTTATGAGTACCTCTGCATTGATGACTGTTGGATGGCTCCCAAAGAGATTCAG
AAGGCAGACTTCAGGCAGACCCTCAGCGCTTTCCTCATGGGATTCGCCAGCTAGC
TAATTATGTTCACAGCAAAGGACTGAAGCTAGGGATTTATGCAGATGTTGGAAAT
AAAACCTGCGCAGGCTTCCCTGGGAGTTTTGGATACTACGACATTGATGCCCAGA
CCTTTGCTGACTGGGGAGTAGATCTGCTAAAATTTGATGGTTGTTACTGTGACAG
TTTGGAAAATTTGGCAGATGGTTATAAGCACATGTCCTTGGCCCTGAATAGGACT
GGCAGAAGCATTGTGTACTCCTGTGAGTGGCCTCTTTATATGTGGCCCTTTCAAA
AGCCCAATTATACAGAAATCCGACAGTACTGCAATCACTGGCGAAATTTTGCTGA
CATTGATGATTCCTGGAAAAGTATAAAGAGTATCTTGGACTGGACATCTTTTAAC
CAGGAGAGAATTGTTGATGTTGCTGGACCAGGGGGTTGGAATGACCCAGATATG
TTAGTGATTGGCAACTTTGGCCTCAGCTGGAATCAGCAAGTAACTCAGATGGCCC
TCTGGGCTATCATGGCTGCTCCTTTATTCATGTCTAATGACCTCCGACACATCAGC
CCTCAAGCCAAAGCTCTCCTTCAGGATAAGGACGTAATTGCCATCAATCAGGACC
CCTTGGGCAAGCAAGGGTACCAGCTTAGACAGGGAGACAACTTTGAAGTGTGG
AACGACCTCTCTCAGGCTTAGCCTGGGCTGTAGCTATGATAAACCGGCAGGAGAT
TGGTGGACCTCGCTCTTATACCATCGCAGTTGCTTCCCTGGGTAAAGGAGTGGCC
TGTAATCCTGCCTGCTTCATCACACAGCTCCTCCCTGTGAAAAGGAAGCTAGGGT
TCTATGAATGGACTTCAAGGTTAAGAAGTCACATAAATCCCACAGGCACTGTTTT
GCTTCAGCTAGAAAATACAATGCAGATGTCATTAAAAGACTTACTTTAA
```

Fig. 10

Responsive GAA missense

| GAA mutation | n | % wild-type GAA activity | |
|---|---|---|---|
| | | No DNJ | With 100nM DNJ |
| E262K | 3 | 0.5 ± 0.3 | 1.8 ± 0.6 |
| P266S | 3 | 14.2 ± 0.3 | 22.4 ± 1.0 |
| P285R | 3 | 2.2 ± 0.4 | 4.8 ± 0.8 |
| P285S | 3 | 7.0 ± 0.9 | 11.8 ± 0.9 |
| L291F | 2 | 3.4 ± 0.9 | 4.4 ± 0.2 |
| L291H | 3 | 4.3 ± 0.7 | 6.0 ± 0.8 |
| L291P | 3 | 3.0 ± 0.5 | 6.8 ± 1.5 |
| M318K | 3 | 3.2 ± 0.9 | 11.2 ± 2.6 |
| G377R | 6 | 0.3 ± 0.1 | 0.7 ± 0.1 |
| A445P | 6 | 1.0 ± 0.2 | 1.9 ± 0.3 |
| Y455C | 1 | 3.1 | 8.6 |
| Y455F | 3 | 4.6 ± 0.5 | 11.0 ± 2.2 |
| P457L | 4 | 6.4 ± 0.8 | 13.5 ± 1.7 |
| G483R | 2 | 1.7 ± 0.6 | 8.6 ± 0.9 |
| G483V | 2 | 0.8 ± 0.3 | 6.5 ± 1.9 |
| M519V | 4 | 3.1 ± 0.3 | 5.1 ± 0.1 |
| S529V | 4 | 6.4 ± 0.7 | 14.6 ± 0.4 |
| P545L | 20 | 3.0 ± 0.2 | 13.0 ± 0.9 |
| G549R | 3 | 7.5 ± 1.1 | 13.5 ± 1.9 |
| L552P | 3 | 2.5 ± 0.8 | 9.6 ± 1.2 |
| Y575S | 7 | 0.4 ± 0.1 | 3.2 ± 0.4 |
| E579K | 7 | 3.8 ± 0.3 | 13.4 ± 1.1 |
| A610V | 3 | 0.5 ± 0.0 | 2.7 ± 0.3 |
| H612Q | 3 | 0.2 ± 0.1 | 0.9 ± 0.4 |
| A644P | 2 | 0.8 ± 0.1 | 2.1 ± 0.3 |
| ΔN470 | 4 | 1.4 ± 0.2 | 3.8 ± 0.4 |

FIG. 11A

Nucleic acid sequence of human lysosomal alpha-glucosidase (GAA) (GenBank Accession No.: Y00839).

| | |
|---|---|
| cagttgggaa agctgaggtt gtcgccgggg ccgcgggtgg aggtcgggga tgaggcagca | 60 |
| ggtaggacag tgacctcggt gacgcgaagg accccggcca cctctaggtt ctcctcgtcc | 120 |
| gcccgttgtt cagcgaggga ggctctgggc ctgccgcagc tgacggggaa actgaggcac | 180 |
| ggagcgggcc tgtaggagct gtccaggcca tctccaacca tgggagtgag gcacccgccc | 240 |
| tgctcccacc ggctcctggc cgtctgcgcc ctcgtgtcct tggcaaccgc tgcactcctg | 300 |
| gggcacatcc tactccatga tttcctgctg gttccccgag agctgagtgg ctcctcccca | 360 |
| gtcctggagg agactcaccc agctcaccag cagggagcca gcagaccagg gccccgggat | 420 |
| gcccaggcac accccggccg tcccagagca gtgcccacac agtgcgacgt cccccccaac | 480 |
| agccgcttcg attgcgcccc tgacaaggcc atcacccagg aacagtgcga ggcccgcggc | 540 |
| tgctgctaca tccctgcaaa gcaggggctg cagggagccc agatggggca gccctggtgc | 600 |
| ttcttcccac ccagctaccc cagctacaag ctggagaacc tgagctcctc tgaaatgggc | 660 |
| tacacggcca ccctgacccg taccacccc accttcttcc ccaaggacat cctgacccctg | 720 |
| cggctggacg tgatgatgga gactgagaac cgcctccact tcacgatcaa agatccagct | 780 |
| aacaggcgct acgaggtgcc cttggagacc ccgcgtgtcc acagccgggc accgtcccca | 840 |
| ctctacagcg tggagttctc cgaggagccc ttcggggtga tcgtgcaccg gcagctggac | 900 |
| ggccgcgtgc tgctgaacac gacggtggcg cccctgttct ttgcggacca gttccttcag | 960 |
| ctgtccacct cgctgccctc gcagtatatc acaggcctcg ccgagcacct cagtccctg | 1020 |
| atgctcagca ccagctggac caggatcacc ctgtggaacc gggaccttgc gccacgccc | 1080 |
| ggtgcgaacc tctacgggtc tcacccttttc tacctggcgc tggaggacgg cgggtcggca | 1140 |
| cacggggtgt tcctgctaaa cagcaatgcc atggatgtgg tcctgcagcc gagccctgcc | 1200 |
| cttagctgga ggtcgacagg tgggatcctg gatgtctaca tcttcctggg cccagagccc | 1260 |
| aagagcgtgg tgcagcagta cctggacgtt gtgggatacc cgttcatgcc gccatactgg | 1320 |
| ggcctgggct tccacctgtg ccgctggggc tactcctcca ccgctatcac cgccaggtg | 1380 |
| gtggagaaca tgaccagggc ccacttcccc ctggacgtcc aatggaacga cctggactac | 1440 |
| atggactccc ggaggggactt cacgttcaac aaggatggct ccgggactt cccggccatg | 1500 |
| gtgcaggagc tgcaccaggg cggccggcgc tacatgatga tcgtggatcc tgccatcagc | 1560 |
| agctcgggcc ctgccgggag ctacaggccc tacgacgagg tctgcggag gggggttttc | 1620 |
| atcaccaacg agaccggcca gccgctgatt gggaaggtat ggccgggtc cactgccttc | 1680 |
| cccgacttca ccaaccccac agcctggcc tggtgggagg acatggtggc tgagttccat | 1740 |
| gaccaggtgc cttcgacgg catgtggatt gacatgaacg agccttccaa cttcatcaga | 1800 |
| ggctctgagg acggctgccc caacaatgag ctggagaacc cacctacgt gcctggggtg | 1860 |
| gttgggggga cctccaggc ggccaccatc tgtcctcca gccaccagtt tctctccaca | 1920 |
| cactacaacc tgcacaacct ctacggcctg accgaagcca tgcctccca cagggcgctg | 1980 |
| gtgaaggctc gggggacacg cccatttgtg atctcccgct cgaccttgc tggccacggc | 2040 |
| cgatacgccg gccactggac gggggacgtg tggagctcct gggagcagct cgcctcctcc | 2100 |
| gtgccagaaa tcctgcagtt taacctgctg ggggtgcctc tggtcggggc cgacgtctgc | 2160 |

FIG. 11B

```
ggcttcctgg gcaacacctc agaggagctg tgtgtgcgct ggacccagct gggggccttc    2220
tacccctica tgcggaacca caacagcctg ctcagtctgc cccaggagcc gtacagcttc    2280
agcgagccgg cccagcaggc catgaggaag gccctcaccc tgcgctacgc actcctcccc    2340
cacctctaca cactgttcca ccaggcccac gtcgcggggg agaccgtggc ccggcccctc    2400
ttcctggagt tccccaagga ctctagcacc tggactgtgg accaccagct cctgtggggg    2460
gaggccctgc tcatcacccc agtgctccag gccgggaagg ccgaagtgac tggctacttc    2520
cccttgggca catggtacga cctgcagacg gtgccaatag aggcccttgg cagcctccca    2580
cccccacctg cagctccccg tgagccagcc atccacagcg aggggcagtg ggtgacgctg    2640
ccggccccc tggacaccat caacgtccac ctccgggctg ggtacatcat cccctgcag    2700
ggccctggcc tcacaaccac agagtcccgc cagcagccca tggccctggc tgtggccctg    2760
accaagggtg gagaggcccg aggggagctg ttctgggacg atggagagag cctggaagtg    2820
ctggagcgag gggcctacac acaggtcatc ttcctggcca ggaataacac gatcgtgaat    2880
gagctggtac gtgtgaccag tgagggagct ggcctgcagc tgcagaaggt gactgtcctg    2940
ggcgtggcca cggcgcccca gcaggtcctc tccaacggtg tccctgtctc caacttcacc    3000
tacagccccg acaccaaggt cctggacatc tgtgtctcgc tgttgatggg agagcagttt    3060
ctcgtcagct ggtgttagcc gggcggagtg tgttagtctc tccagaggga ggctggttcc    3120
ccagggaagc agagcctgtg tgcgggcagc agctgtgtgc gggcctgggg gttgcatgtg    3180
tcacctggag ctgggcacta accattccaa gccgcgcat cgcttgtttc cacctcctgg     3240
gccggggctc tggcccccaa cgtgtctagg agagctttct ccctagatcg cactgtgggc    3300
cggggcctgg agggctgctc tgtgttaata agattgtaag gtttgccctc ctcacctgtt    3360
gccggcatgc gggtagtatt agccaccccc ctccatctgt tcccagcacc ggagaagggg    3420
gtgctcaggt ggaggtgtgg ggtatgcacc tgagctcctg cttcgcgcct gctgctctgc    3480
cccaacgcga ccgcttcccg gctgcccaga gggctggatg cctgccggtc cccgagcaag    3540
cctgggaact caggaaaatt cacaggactt gggagattct aaatcttaag tgcaattatt    3600
ttaataaaag gggcatttgg aatc                                           3624
```

FIG. 16A

Amino acid sequence encoded by a human lysosomal alpha-glucosidase nucleic acid (GAA) (GenBank Accession No.: Y00839).

```
Met Gly Val Arg His Pro Pro Cys Ser His Arg Leu Leu Ala Val Cys
1               5                   10                  15
Ala Leu Val Ser Leu Ala Thr Ala Ala Leu Leu Gly His Ile Leu Leu
                20                  25                  30
His Asp Phe Leu Leu Val Pro Arg Glu Leu Ser Gly Ser Ser Pro Val
            35                  40                  45
Leu Glu Glu Thr His Pro Ala His Gln Gln Gly Ala Ser Arg Pro Gly
        50                  55                  60
Pro Arg Asp Ala Gln Ala His Pro Gly Arg Pro Arg Ala Val Pro Thr
65                  70                  75                  80
Gln Cys Asp Val Pro Pro Asn Ser Arg Phe Asp Cys Ala Pro Asp Lys
                85                  90                  95
Ala Ile Thr Gln Glu Gln Cys Glu Ala Arg Gly Cys Cys Tyr Ile Pro
            100                 105                 110
Ala Lys Gln Gly Leu Gln Gly Ala Gln Met Gly Gln Pro Trp Cys Phe
        115                 120                 125
Phe Pro Pro Ser Tyr Pro Ser Tyr Lys Leu Glu Asn Leu Ser Ser Ser
    130                 135                 140
Glu Met Gly Tyr Thr Ala Thr Leu Thr Arg Thr Thr Pro Thr Phe Phe
145                 150                 155                 160
Pro Lys Asp Ile Leu Thr Leu Arg Leu Asp Val Met Met Glu Thr Glu
                165                 170                 175
Asn Arg Leu His Phe Thr Ile Lys Asp Pro Ala Asn Arg Arg Tyr Glu
            180                 185                 190
Val Pro Leu Glu Thr Pro Arg Val His Ser Arg Ala Pro Ser Pro Leu
        195                 200                 205
Tyr Ser Val Glu Phe Ser Glu Glu Pro Phe Gly Val Ile Val His Arg
    210                 215                 220
Gln Leu Asp Gly Arg Val Leu Leu Asn Thr Thr Val Ala Pro Leu Phe
225                 230                 235                 240
Phe Ala Asp Gln Phe Leu Gln Leu Ser Thr Ser Leu Pro Ser Gln Tyr
                245                 250                 255
Ile Thr Gly Leu Ala Glu His Leu Ser Pro Leu Met Leu Ser Thr Ser
            260                 265                 270
Trp Thr Arg Ile Thr Leu Trp Asn Arg Asp Leu Ala Pro Thr Pro Gly
        275                 280                 285
Ala Asn Leu Tyr Gly Ser His Pro Phe Tyr Leu Ala Leu Glu Asp Gly
    290                 295                 300
Gly Ser Ala His Gly Val Phe Leu Leu Asn Ser Asn Ala Met Asp Val
305                 310                 315                 320
Val Leu Gln Pro Ser Pro Ala Leu Ser Trp Arg Ser Thr Gly Gly Ile
                325                 330                 335
Leu Asp Val Tyr Ile Phe Leu Gly Pro Glu Pro Lys Ser Val Val Gln
            340                 345                 350
Gln Tyr Leu Asp Val Val Gly Tyr Pro Phe Met Pro Pro Tyr Trp Gly
        355                 360                 365
```

FIG. 16B

```
Leu Gly Phe His Leu Cys Arg Trp Gly Tyr Ser Ser Thr Ala Ile Thr
    370                 375                 380
Arg Gln Val Val Glu Asn Met Thr Arg Ala His Phe Pro Leu Asp Val
385                     390                 395                 400
Gln Trp Asn Asp Leu Asp Tyr Met Asp Ser Arg Arg Asp Phe Thr Phe
                405                     410                 415
Asn Lys Asp Gly Phe Arg Asp Phe Pro Ala Met Val Gln Glu Leu His
            420                     425                 430
Gln Gly Gly Arg Arg Tyr Met Met Ile Val Asp Pro Ala Ile Ser Ser
        435                     440                 445
Ser Gly Pro Ala Gly Ser Tyr Arg Pro Tyr Asp Glu Gly Leu Arg Arg
    450                     455                 460
Gly Val Phe Ile Thr Asn Glu Thr Gly Gln Pro Leu Ile Gly Lys Val
465                     470                 475                 480
Trp Pro Gly Ser Thr Ala Phe Pro Asp Phe Thr Asn Pro Thr Ala Leu
                485                     490                 495
Ala Trp Trp Glu Asp Met Val Ala Glu Phe His Asp Gln Val Pro Phe
            500                     505                 510
Asp Gly Met Trp Ile Asp Met Asn Glu Pro Ser Asn Phe Ile Arg Gly
        515                     520                 525
Ser Glu Asp Gly Cys Pro Asn Asn Glu Leu Glu Asn Pro Pro Tyr Val
    530                     535                 540
Pro Gly Val Val Gly Gly Thr Leu Gln Ala Ala Thr Ile Cys Ala Ser
545                     550                 555                 560
Ser His Gln Phe Leu Ser Thr His Tyr Asn Leu His Asn Leu Tyr Gly
                565                     570                 575
Leu Thr Glu Ala Ile Ala Ser His Arg Ala Leu Val Lys Ala Arg Gly
            580                     585                 590
Thr Arg Pro Phe Val Ile Ser Arg Ser Thr Phe Ala Gly His Gly Arg
        595                     600                 605
Tyr Ala Gly His Trp Thr Gly Asp Val Trp Ser Ser Trp Glu Gln Leu
    610                     615                 620
Ala Ser Ser Val Pro Glu Ile Leu Gln Phe Asn Leu Leu Gly Val Pro
625                     630                 635                 640
Leu Val Gly Ala Asp Val Cys Gly Phe Leu Gly Asn Thr Ser Glu Glu
                645                     650                 655
Leu Cys Val Arg Trp Thr Gln Leu Gly Ala Phe Tyr Pro Phe Met Arg
            660                     665                 670
Asn His Asn Ser Leu Leu Ser Leu Pro Gln Glu Pro Tyr Ser Phe Ser
        675                     680                 685
Glu Pro Ala Gln Gln Ala Met Arg Lys Ala Leu Thr Leu Arg Tyr Ala
    690                     695                 700
Leu Leu Pro His Leu Tyr Thr Leu Phe His Gln Ala His Val Ala Gly
705                     710                 715                 720
Glu Thr Val Ala Arg Pro Leu Phe Leu Glu Phe Pro Lys Asp Ser Ser
                725                     730                 735
Thr Trp Thr Val Asp His Gln Leu Leu Trp Gly Glu Ala Leu Leu Ile
            740                     745                 750
Thr Pro Val Leu Gln Ala Gly Lys Ala Glu Val Thr Gly Tyr Phe Pro
        755                     760                 765
Leu Gly Thr Trp Tyr Asp Leu Gln Thr Val Pro Ile Glu Ala Leu Gly
    770                     775                 780
Ser Leu Pro Pro Pro Ala Ala Pro Arg Glu Pro Ala Ile His Ser
785                     790                 795                 800
Glu Gly Gln Trp Val Thr Leu Pro Ala Pro Leu Asp Thr Ile Asn Val
```

FIG. 16C

```
                        805                         810                         815
    His Leu Arg Ala Gly Tyr Ile Ile Pro Leu Gln Gly Pro Gly Leu Thr
                820                         825                         830
    Thr Thr Glu Ser Arg Gln Gln Pro Met Ala Leu Ala Val Ala Leu Thr
                835                         840                         845
    Lys Gly Gly Glu Ala Arg Gly Glu Leu Phe Trp Asp Asp Gly Glu Ser
                850                         855                         860
    Leu Glu Val Leu Glu Arg Gly Ala Tyr Thr Gln Val Ile Phe Leu Ala
    865                         870                         875             880
    Arg Asn Asn Thr Ile Val Asn Glu Leu Val Arg Val Thr Ser Glu Gly
                            885                         890             895
    Ala Gly Leu Gln Leu Gln Lys Val Thr Val Leu Gly Val Ala Thr Ala
                900                         905                         910
    Pro Gln Gln Val Leu Ser Asn Gly Val Pro Val Ser Asn Phe Thr Tyr
                915                         920                         925
    Ser Pro Asp Thr Lys Val Leu Asp Ile Cys Val Ser Leu Leu Met Gly
        930                         935                         940
    Glu Gln Phe Leu Val Ser Trp Cys
    945                 950
```

METHOD TO PREDICT RESPONSE TO PHARMACOLOGICAL CHAPERONE TREATMENT OF DISEASES

CROSS-REFERENCE TO RELATED APPLICATION

The present application is a continuation of International Application No. PCT/US09/033963, filed Feb. 12, 2009 and claims the benefit of U.S. Provisional Application No. 61/028,141, filed Feb. 12, 2008, U.S. Provisional Application No. 61/035,684, filed Mar. 11, 2008, U.S. Provisional Application No. 61/093,631, filed Sep. 2, 2008, and U.S. Provisional Application No. 61/113,496, filed Nov. 11, 2008, Each of these applications are hereby incorporated by reference in their entireties.

FIELD OF THE INVENTION

The present invention provides methods to determine whether a patient with a lysosomal storage disorder will benefit from treatment with a specific pharmacological chaperone. The present invention also provides an in vitro method for determining enzyme (e.g., α-galactosidase A, α-glucosidase or glucocerebrosidase) responsiveness to a pharmacological chaperone (e.g., 1-deoxygalactonojirimycin, 1-deoxynojirimycin or isofagomine) in a cell line expressing a mutant form of the enzyme. The invention also provides a method for diagnosing a lysosomal storage disorder (e.g., Fabry disease, Pompe disease or Gaucher disease) in patients suspected of having a lysosomal storage disorder, and implementing the proper treatment based on the diagnosis (e.g., choosing a particular therapeutic agent to administer to the patient).

BACKGROUND

In the human body, proteins are involved in almost every aspect of cellular function. Proteins are linear strings of amino acids that fold and twist into specific three-dimensional shapes in order to function properly. Certain human diseases result from mutations that cause changes in the amino acid sequence of a protein which reduce its stability and may prevent it from folding properly. The majority of genetic mutations that lead to the production of less stable or misfolded proteins are called missense mutations. These mutations result in the substitution of a single amino acid for another in the protein. Because of this error, missense mutations often result in proteins that have a reduced level of biological activity. In addition to missense mutations, there are also other types of mutations that can result in proteins with reduced biological activity.

Proteins generally fold in a specific region of the cell known as the endoplasmic reticulum, or ER. The cell has quality control mechanisms that ensure that proteins are folded into their correct three-dimensional shape before they can move from the ER to the appropriate destination in the cell, a process generally referred to as protein trafficking. Misfolded proteins are often eliminated by the quality control mechanisms after initially being retained in the ER. In certain instances, misfolded proteins can accumulate in the ER before being eliminated.

The retention of misfolded proteins in the ER interrupts their proper trafficking, and the resulting reduced biological activity can lead to impaired cellular function and ultimately to disease. In addition, the accumulation of misfolded proteins in the ER may lead to various types of stress on cells, which may also contribute to cellular dysfunction and disease.

Lysosomal storage diseases (LSDs) are characterized by deficiencies of lysosomal enzymes due to mutations in the genes encoding the lysosomal enzymes. This results in the pathologic accumulation of substrates of those enzymes, which include lipids, carbohydrates, and polysaccharides. There are about fifty known LSDs to date, which include Gaucher disease, Fabry disease, Pompe disease, Tay Sachs disease and the mucopolysaccharidoses (MPS). Most LSDs are inherited as an autosomal recessive trait, although males with Fabry disease and MPS II are hemizygotes because the disease genes are encoded on the X chromosome. For most LSDs, there is no available treatment beyond symptomatic management. For several LSDs, including Gaucher, Fabry, Pompe, and MPS I and VI, enzyme replacement therapy (ERT) using recombinant enzymes is available. For Gaucher disease, substrate reduction therapy (SRT) also is available in limited situations. SRT employs a small molecule inhibitor of an enzyme required for the synthesis of glucosylceramide (the GD substrate). The goal of SRT is to reduce production of the substrate and reduce pathologic accumulation.

Although there are many different mutant genotypes associated with each LSD, some of the mutations, including some of the most prevalent mutations, are missense mutations which can lead to the production of a less stable enzyme. These less stable enzymes are sometimes prematurely degraded by the ER-associated degradation pathway. This results in the enzyme deficiency in the lysosome, and the pathologic accumulation of substrate. Such mutant enzymes are sometimes referred to in the pertinent art as "folding mutants" or "conformational mutants."

Diagnosis of Fabry Disease

Because Fabry disease is rare, involves multiple organs, has a wide age range of onset, and is heterogeneous, proper diagnosis is a challenge. Awareness is low among health care professionals and misdiagnoses are frequent. Some examples of diagnoses seriously considered in patients who were eventually diagnosed with Fabry's disease include: mitral valve prolapse, glomerulonephritis, idiopathic proteinuria, systemic lupus erythematosus, Whipple's disease, acute abdomen, ulcerative colitis, acute intermittent porphyrias, and occult malignancies. Thus, even for classically affected males, diagnosis typically takes from about 5-7 years or even longer. This is a concern because the longer a person has Fabry disease, the more damage is likely to occur in the affected organs and tissues and the more serious the person's condition may become. Diagnosis of Fabry disease is most often confirmed on the basis of decreased α-Gal A activity in plasma or peripheral leukocytes (WBCs) once a patient is symptomatic, coupled with mutational analysis. In females, diagnosis is even more challenging since the enzymatic identification of carrier females is less reliable due to random X-chromosomal inactivation in some cells of carriers. For example, some obligate carriers (daughters of classically affected males) have α-Gal A enzyme activities ranging from normal to very low activities. Since carriers can have normal α-Gal A enzyme activity in leukocytes, only the identification of an α-Gal A mutation by genetic testing provides precise carrier identification and/or diagnosis.

Treatment of Fabry Disease

One approved therapy for treating Fabry disease diseases is enzyme replacement therapy, which typically involves intravenous, infusion of a purified form of the corresponding wild-type protein (Fabrazyme®, Genzyme Corp.). One of the main complications with protein replacement therapy is attainment and maintenance of therapeutically effective amounts of protein in vivo due to rapid degradation of the infused protein. The current approach to overcome this problem is to perform numerous costly high dose infusions.

Protein replacement therapy has several additional caveats, such as difficulties with large-scale generation, purification, and storage of properly folded protein; obtaining glycosylated native protein; generation of an anti-protein immune response; and inability of protein to cross the blood-brain barrier to mitigate central nervous system pathologies (i.e., low bioavailability). In addition, replacement enzyme cannot penetrate the heart or kidney in sufficient amounts to reduce substrate accumulation in the renal podocytes or cardiac myocytes, which figure prominently in Fabry pathology.

Gene therapy using recombinant vectors containing nucleic acid sequences that encode a functional protein, or using genetically modified human cells that express a functional protein, is also being developed to treat protein deficiencies and other disorders that benefit from protein replacement.

A third, relatively recent approach to treating some enzyme deficiencies involves the use of small molecule inhibitors to reduce production of the natural substrate of deficient enzyme proteins, thereby ameliorating the pathology. This "substrate reduction" approach has been specifically described for a class of about 40 related enzyme disorders called lysosomal storage disorders that include glycosphingolipid storage disorders. The small molecule inhibitors proposed for use as therapy are specific for inhibiting the enzymes involved in synthesis of glycolipids, reducing the amount of cellular glycolipid that needs to be broken down by the deficient enzyme.

It has previously been shown that the binding of small molecule inhibitors of enzymes associated with LSDs can increase the stability of both mutant enzyme and the corresponding wild-type enzyme (see U.S. Pat. Nos. 6,274,597; 6,583,158; 6,589,964; 6,599,919; 6,916,829, and 7,141,582 all incorporated herein by reference). In particular, it was discovered that administration of small molecule derivatives of glucose and galactose, which are specific, selective competitive inhibitors for several target lysosomal enzymes, effectively increased the stability of the enzymes in cells in vitro and, thus, increased trafficking of the enzymes to the lysosome. Thus, by increasing the amount of enzyme in the lysosome, hydrolysis of the enzyme substrates is expected to increase. The original theory behind this strategy was as follows: since the mutant enzyme protein is unstable in the ER (Ishii et al., *Biochem. Biophys. Res. Comm.* 1996; 220: 812-815), the enzyme protein is retarded in the normal transport pathway (ER→Golgi apparatus→endosomes→lysosome) and prematurely degraded. Therefore, a compound which binds to and increases the stability of a mutant enzyme, may serve as a "chaperone" for the enzyme and increase the amount that can exit the ER and move to the lysosomes. In addition, because the folding and trafficking of some wild-type proteins is incomplete, with up to 70% of some wild-type proteins being degraded in some instances prior to reaching their final cellular location, the chaperones can be used to stabilize wild-type enzymes and increase the amount of enzyme which can exit the ER and be trafficked to lysosomes. This strategy has been shown to increase several lysosomal enzymes in vitro and in vivo, including β-glucocerebrosidase and α-glucosidase, deficiencies of which are associated with Gaucher and Pompe disease, respectively.

However, as indicated above, successful candidates for SPC therapy should have a mutation which results in the production of an enzyme that has the potential to be stabilized and folded into a conformation that permits trafficking out of the ER. Mutations which severely truncate the enzyme, such as nonsense mutations, or mutations in the catalytic domain which prevent binding of the chaperone, will not be as likely to be "rescuable" or "enhanceable" using SPC therapy, i.e., to respond to SPC therapy. While missense mutations outside the catalytic site are more likely to be rescuable using SPCs, there is no guarantee, necessitating screening for responsive mutations. This means that, even when Fabry disease is diagnosed by detecting deficient α-Gal A activity in WBCs, it is very difficult, if not impossible, to predict whether a particular Fabry patient will respond to treatment with an SPC without benefit of the present invention. Moreover, since WBCs only survive for a short period of time in culture (in vitro), screening for SPC enhancement of α-Gal A is difficult and not optimal for the patient.

In order to apply SPC therapy effectively, a broadly applicable, fast and efficient method for screening patients for responsiveness to SPC therapy needs to be adopted prior to initiation of treatment. Treatment can then be implemented based on the results of the screening Thus, there remains in the art a need for relatively non-invasive methods to rapidly assess enzyme enhancement with potential therapies prior to making treatment decisions, for both cost and emotional benefits to the patient.

SUMMARY OF THE INVENTION

One embodiment of the present invention provides a method for determining whether a patient will be a candidate for SPC therapy. Specifically, the present invention provides an in vitro assay to evaluate protein activity in the presence or absence of an SPC, wherein an SPC that increases the activity of the protein in the in vitro assay is an SPC that can be used for SPC therapy. In one embodiment, the in vitro assay comprises expressing a mutant protein in a host cell, contacting the mutant protein with a candidate SPC, and determining if the mutant protein contacted with the SPC exhibits an increased level of activity (preferably a statistically significant increase) when compared to a mutant protein expressed in a host cell that is not contacted with the candidate SPC. When a candidate SPC increases the activity of a mutant protein according to the assay of the invention, such a candidate SPC can be used for SPC therapy to treat a patient expressing the same mutant protein tested in the in vitro assay.

In one embodiment, the protein is an enzyme. In another embodiment, the protein is a lysosomal enzyme. In yet another embodiment, the protein is α-galactosidase A (α-GAL; α-GAL A). In other embodiments, the protein is alpha-glucosidase (Acid α-glucosidase ; α-glucosidase; GAA). In other embodiments, the protein is glucocerebrosidase (β-glucosidase; Gba; GCase).

The present invention also includes the basis for evaluation of SPC as a treatment option for any number of other protein abnormalities and/or enzyme deficiencies and/or a protein folding disorders.

The present invention further provides a written record (e.g., a "treatment reference table") listing protein mutations and the responsiveness of each of the mutations to SPC therapy. Such a list can be used in determining treatment options for a patient, whereby the patient, or the patient's physician or doctor, can select the proper therapeutic approach, for example, an SPC for treatment by identifying the patient's protein mutation, and cross-referencing the mutation with the list to identify whether an SPC will increase the activity of the patients particular mutant enzyme.

In another embodiment, the "treatment reference table" lists mutations for a lysosomal enzyme, and the treatment reference table is employed to determine the best therapeutic approach to treat a lysosomal storage disorder. In a further embodiment of the invention, the protein is α-Gal A, and the disease is Fabry disease. In other embodiments of the invention, the protein is GAA, and the disease is Pompe disease, In other embodiments of the invention, the protein is Gba, and the disease is Gaucher disease.

In one embodiment, the treatment reference table describes mutant forms of enzyme, such as a lysomal enzyme (e.g., α-Gal A, Gcase, and GAA) and treatment options are ascertained for lysosomal storage disorders (e.g., Fabry, Gacher and Pompe Disease).

In one embodiment, the invention also provides for methods of creating a treatment reference table, wherein the treatment reference table can be for any protein folding disorder or disorder treatable with an SPC. This class of disease includes the other lysosomal storage disorders, Cystic Fibrosis (CFTR) (respiratory or sweat gland epithelial cells), familial hypercholesterolemia (LDL receptor; LPL-adipocytes or vascular endothelial cells), cancer (p53; PTEN-tumor cells), and amyloidoses (transthyretin) among others.

In another embodiment, the present invention provides for methods of treating a patient diagnosed as expressing certain mutant proteins (e.g., lysosomal enzymes such as α-GAL A), wherein activity of the mutant protein (e.g., α-Gal A), when expressed in a host cell, can be increased upon administration of an SPC for that protein (for example, 1-deoxygalactonojirimycin, DGJ, as an SPC for mutant α-GAL A).

The present invention also provides for diagnostic kits containing the components required to perform the assay.

BRIEF DESCRIPTION OF THE DRAWINGS

FIG. 1A-C. Shows a listing of Fabry mutations generated by site-directed mutagenesis. The text indicates whether HEK-293 cells expressing each of the listed mutations responds to DGJ treatment in the transient transfection assay: italics=not yet tested; bold and underscored=no response to DGJ; plain text (not italicized, bold, or underscored)=response to DGJ.

FIG. 2A-C Shows the responsiveness of different α-Gal A mutations to DGJ treatment. The magnitude of increase in α-Gal A activity levels after DGJ treatment and EC50 values are listed for every tested mutation in FIG. 1A-D that responded to DGJ treatment. The increase in enzyme activity is shown as a percentage of wild type α-Gal A activity.

FIG. 6 Shows the oligonucleotide primer pairs used to generate the point mutations in the α-Gal A gene through site-directed mutagenesis.

FIG. 7 Shows the α-Gal A cDNA sequence that was mutated through the site-directed mutagenesis.

FIG. 10 Shows a listing of Pompe mutations generated by site-directed mutagenesis. The text indicates whether COS-7 cells expressing each of the listed mutations responds to DNJ treatment in the transient transfection assay.

FIG. 11A-B Shows the nucleic acid sequence of human lysosomal alpha-glucosidase (GAA) (GenBank Accession No.: Y00839).

FIG. 12 also shows that DNJ promoted processing of GAA to the 95/76/70 kDa forms.

FIG. 16A-C Shows the amino acid sequence encoded by a human lysosomal alpha-glucosidase (GAA) nucleic acid (GenBank Accession No.: Y00839).

DETAILED DESCRIPTION

Figure 3:
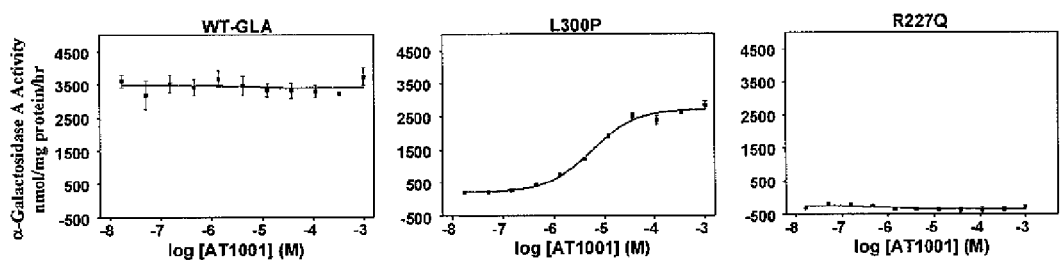
FIG. 3 Shows representative examples of wild type and mutant α-Gal A responses to DGJ treatment. α-Gal A activity (expressed as nmol/mg protein/hr of 4-MU released) was measured in lysates prepared from transfected HEK 293 cells incubated with increasing concentrations of DGJ. A typical concentration-dependent response is shown for L300P and a typical negative response to DGJ is shown for R227Q. Wild type exhibits high baseline activity and thus does not respond to DGJ in this assay.

The present invention provides an in vitro assay to provide accurate determination of whether an SPC enhances activity of a mutant protein.

In one embodiment, the protein is a lysosomal enzyme, wherein the lysosomal enzyme, when mutated, causes a lysosomal storage disorder. The concepts of the present invention, however, can be globally applied to any disease or condition characterized by mutant proteins amenable to SPC-therapy, in which the proteins have one or more specific mutations that can be generated in vitro, for example, by site-directed mutagenesis.

In one specific embodiment, the invention provides methods for determining whether an SPC enhances enzyme activity of a mutant α-Gal A enzyme, and can therefore be utilized as an effective therapeutic treatment for a Fabry disease patient expressing the same α-Gal A mutation.

In another specific embodiment, the invention provides methods for determining whether an SPC enhances enzyme activity of a mutant GAA enzyme, and can therefore be utilized as an effective therapeutic treatment for a Pompe disease patient expressing the same GAA mutation.

In another specific embodiment, the invention provides methods for determining whether an SPC enhances enzyme activity of a mutant Gba enzyme, and can therefore be utilized as an effective therapeutic treatment for a Gaucher disease patient expressing the same Gba mutation.

According to the methods of the present invention, assays are provided that allow for the determination of whether a patient expressing a mutant lysosomal enzyme will be a candidate for SPC therapy. The new in vitro assay is extremely sensitive and can be performed on a host cell transfected with a nucleic acid construct encoding a mutant lysosomal enzyme. Specific candidate SPCs can then be assayed to determine if the candidate SPC is capable of increasing the activity of the mutant enzyme expressed by the host cell. Thus, unlike assays which utilize cells derived from a patient with a lysosomal storage disorder, the assay of the invention avoids time consuming steps such as collection of a sample from a patient, purification of cells from the sample, and culturing the cells from the sample in vitro.

The present invention also provides for a method of determining whether a patient expressing a mutant protein (e.g. a lysosomal enzyme) will be a candidate for SPC therapy, wherein a person, for example, a patient's physician or doctor, can look up the mutant protein (e.g. a lysosomal enzyme mutation) in a treatment reference table to determine if the patient's mutation will respond to SPC therapy. The reference table is generated from the results of in vitro analysis of SPC response in a cell line that has been transformed with a nucleic acid vector which encodes the mutant protein.

Furthermore, the invention also provides a "Treatment Reference Table" that provides information describing if a particular SPC will be a successful therapy for enhancing the activity of a specific lysosomal enzyme mutation. According to the present invention, the treatment reference table provides information indicating if a candidate SPC can increase the activity of a mutant lysosomal enzyme expressed by a host cell. Based on the response of different mutations to different SPC therapies, the present invention can provide SPC therapy tailored to the patient's specific mutation.

In one non-limiting embodiment, the mutant protein is a mutant lysosomal enzyme, such as, for example, a mutant α-Gal A, GAA or Gba, and the cell line is transfected with a nucleic acid vector which encodes the mutant lysosomal enzyme.

In another non-limiting embodiment, the present invention provides a method of treating a Fabry patient that includes the step of administering to the Fabry patient a therapeutically effective dose of 1-deoxygalactonojirimycin (DGJ), wherein the patient expresses a mutant α-Gal A, the activity of which, when expressed in a host cell, can be increased when contacted with an SPC (e.g. DGJ). Such α-Gal A mutations treatable according to this method include, but are not limited to A121T, A156V, A20P, A288D, A288P, A292P A348P, A73V, C52R, C94Y, D234E, D244H, D244N, D264Y, E338K, E341D, E358K, E398K, E48K, E59K, E66Q, F113L, G144V, G183D, G260A, G271S, G325D, G328A, G35R, G373D, G373S, H225R, I219N, I242N, I270T, I289F, I303N, I317T, I354K, I91T, L14P, L166V, L243F, L300F, L310F, L32P, L45R, M267I, M284T, M296I, M296V, M72V, M76R, N224S, N263S, N298K, N298S, N320I, N320Y, N34K, P205R, P259L, P265L, P265R, P293A, P293S, P409S, P40L, P40S, Q279E, Q279H, Q279R, Q280H, Q280K, Q312H, Q321E, Q321R, Q327E, R301P, R342Q, R363C, R363H, R49G, R49L, R49S, S201Y, S276N, S297C, S345P, T194I, V269M, V316E, W340R, W47L, and W95S mutations.

In one embodiment, the following α-Gal A mutations are excluded from the methods of treating a Fabry patient with a therapeutically effective dose of DGJ: D244N, E358K, E59K, E66Q, G183D, G325D, I289F, I91T, L45R, M296V, N263S, N320Y, P205R, P40S, Q279E, R342Q, R363C, R49L, V316E.

One advantage of the assay described by the present invention is its applicability to female patients with an X-linked lysosomal storage disorder, such as Fabry disease. Because of X-chromosome inactivation, a sample taken from a female patient will comprise both normal healthy cells and enzyme deficient mutant cells. An assay for an SPC's effect on such a sample will show an enhancement in enzyme activity due to the normal wild type enzyme expression of the healthy cells even though the diseased cells with the mutant enzyme may not be responsive to the SPC. The present invention overcomes this obstacle because a cell line transfected with a vector encoding a mutant protein will only express the mutant form of the protein, and thus, there will be no wild type protein expressed by the cell line to cause such pseudo enhancement observed in assays with patient derived cells.

In another non-limiting embodiment, the present invention provides a method of treating a Pompe patient that includes the step of administering to the Pompe patient a therapeutically effective dose of 1-deoxynojirimycin (DNJ), wherein the patient expresses a mutant GAA, the activity of which, when expressed in a host cell, can be increased when contacted with an SPC (e.g. DNJ). Such GAA mutations treatable according to this method include, but are not limited to, E262K, P266S, P285R, P285S, L291F, L291H, L291P, M318K, G377R, A445P, Y455C, Y455F, P457L, G483R, G483V, M519V, S529V, P545L, G549R, L552P, Y575S, E579K, A610V, H612Q, A644P, and ΔN470 mutations.

In another non-limiting embodiment, the present invention provides a method of treating a Gaucher patient with a therapeutically effective dose of isofagomine (IFG), wherein the patient expresses a mutant Gba, the activity of which, when expressed in a host cell, can be increased when contacted with an SPC (e.g. IFG).

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "Fabry disease" refers to an X-linked inborn error of glycosphingolipid catabolism due to deficient lysosomal α-galactosidase A activity. This defect causes accumulation of globotriaosylceramide (ceramide trihexoside) and related glycosphingolipids in vascular endothelial lysosomes of the heart, kidneys, skin, and other tissues.

The term "atypical Fabry disease" refers to patients with primarily cardiac manifestations of the α-Gal A deficiency, namely progressive globotriaosylceramide (GL-3) accumulation in myocardial cells that leads to significant enlargement of the heart, particularly the left ventricle.

A "carrier" is a female who has one X chromosome with a defective α-Gal A gene and one X chromosome with the normal gene and in whom X chromosome inactivation of the normal allele is present in one or more cell types. A carrier is often diagnosed with Fabry disease.

"Pompe disease" refers to an autosomal recessive LSD characterized by deficient acid alpha glucosidase (GAA) activity which impairs lysosomal glycogen metabolism. The enzyme deficiency leads to lysosomal glycogen accumulation and results in progressive skeletal muscle weakness, reduced cardiac function, respiratory insufficiency, and/or CNS impairment at late stages of disease. Genetic mutations in the GAA gene result in either lower expression or produce mutant forms of the enzyme with altered stability, and/or biological activity ultimately leading to disease. (see generally Hirschhorn R, 1995, Glycogen Storage Disease Type II: Acid α-Glucosidase (Acid Maltase) Deficiency, The Metabolic and Molecular Bases of Inherited Disease, Scriver et al., eds., McGraw-Hill, New York, 7th ed., pages 2443-2464). The three recognized clinical forms of Pompe disease (infantile, juvenile and adult) are correlated with the level of residual α-glucosidase activity (Reuser A J et al., 1995, Glycogenosis Type II (Acid Maltase Deficiency), Muscle & Nerve Supplement 3, S61-S69). ASSC (also referred to elsewhere as "pharmacological chaperones") represent a promising new therapeutic approach for the treatment of genetic diseases, such as lysosomal storage disorders (e.g. Pompe Disease).

Infantile Pompe disease (type I or A) is most common and most severe, characterized by failure to thrive, generalized hypotonia, cardiac hypertrophy, and cardiorespiratory failure within the second year of life. Juvenile Pompe disease (type II or B) is intermediate in severity and is characterized by a predominance of muscular symptoms without cardiomegaly. Juvenile Pompe individuals usually die before reaching 20 years of age due to respiratory failure. Adult Pompe disease (type III or C) often presents as a slowly progressive myopathy in the teenage years or as late as the sixth decade (Felice K J et al., 1995, Clinical Variability in Adult-Onset Acid Maltase Deficiency: Report of Affected Sibs and Review of the Literature, Medicine 74, 131-135).

In Pompe, it has been shown that α-glucosidase is extensively modified post-translationally by glycosylation, phosphorylation, and proteolytic processing.

Conversion of the 110 kilodalton (kDa) precursor to 76 and 70 kDa mature forms by proteolysis in the lysosome is required for optimum glycogen catalysis.

As used herein, the term "Pompe Disease" refers to all types of Pompe Disease. The formulations and dosing regimens disclosed in this application may be used to treat, for example, Type I, Type II or Type III Pompe Disease.

The term "Gaucher disease" refers to a deficiency of the lysosomal enzyme β-glucocerebrosidase (Gba) that breaks down fatty glucocerebrosides. The fat then accumulates, mostly in the liver, spleen and bone marrow. Gaucher disease can result in pain, fatigue, jaundice, bone damage, anemia and even death. There are three clinical phenotypes of Gaucher disease. Patients with, Type 1 manifest either early in life or in young adulthood, bruise easily and experience fatigue due to anemia, low blood platelets, enlargement of the liver and spleen, weakening of the skeleton, and in some instances have lung and kidney impairment. There are no signs of brain involvement. In Type II, early-onset, liver and spleen enlargement occurs by 3 months of age and there is extensive brain involvement. There is a high mortality rate by age 2. Type III is characterized by liver and spleen enlargement and brain seizures. The β-glucocerebrosidase gene is located on the human 1q21 chromosome. Its protein precursor contains 536 amino acids and its mature protein is 497 amino acids long.

A "patient" refers to a subject who has been diagnosed with or is suspected of having a particular disease. The patient may be human or animal.

A "Fabry disease patient" refers to an individual who has been diagnosed with or suspected of having Fabry disease and has a mutated α-Gal A as defined further below. Characteristic markers of Fabry disease can occur in male hemizygotes and female carriers with the same prevalence, although females typically are less severely affected.

A "Pompe disease patient" refers to an individual who has been diagnosed with or suspected of having Pompe disease and has a mutated GAA as defined further below.

A "Gaucher disease patient" refers to an individual who has been diagnosed with or suspected of having Gaucher disease and has a mutated Gba as defined further below.

Human α-galactosidase A (α-Gal A) refers to an enzyme encoded by the human GLA gene. The human α-Gal A enzyme consists of 429 amino acids and is in GenBank Accession No. U78027.

In one non-limiting embodiment, human lysosomal alpha-glucosidase (Acid α-glucosidase; GAA) is a lysosomal enzyme which hydrolyzes alpha-1,4- and alpha-1,6-linked-D-glucose polymers present in glycogen, maltose, and isomaltose. Alternative names are as follows: glucoamylase; 1,4-α-D-glucan glucohydrolase; amyloglucosidase; gamma-amylase; and exo-1,4-α-glucosidase. The human GAA gene has been mapped to chromosome 17q25.2-25.3 and has nucleotide and amino acid sequences depicted in GenBank Accession No. Y00839.

The term "human Gba gene" refers to the gene encoding acid β-glucosidase, also referred to as glucocerebrosidase or Gba. The Gba gene is on chromosome 1q21 and involves 11 exons (GenBank Accession No. J03059). There is also a homologous pseudogene for Gba located about 16 kb downstream of the Gba gene (GenBank Accession No. M16328).

The "human Gba" protein refers to the wild-type human Gba protein. The Gba protein consists of 536 amino acids and is in GenBank Accession No. J03059.

The term "mutant protein" includes a protein which has a mutation in the gene encoding the protein which results in the inability of the protein to achieve a stable conformation under the conditions normally present in the ER. The failure to achieve a stable conformation results in a substantial amount of the enzyme being degraded, rather than being transported to the lysosome. Such a mutation is sometimes called a "conformational mutant." Such mutations include, but are not limited to, missense mutations, and in-frame small deletions and insertions.

As used herein in one embodiment, the term "mutant α-Gal A" includes an α-Gal A which has a mutation in the gene encoding α-Gal A which results in the inability of the enzyme to achieve a stable conformation under the conditions normally present in the ER. The failure to achieve a stable conformation results in a substantial amount of the enzyme being degraded, rather than being transported to the lysosome.

Non-limiting, exemplary α-Gal A mutations associated with Fabry disease which result in unstable α-Gal A include L32P; N34S; T41I; M51K; E59K; E66Q; I91T; A97V; R100K; R112C; R112H; F113L; T141L; A143T; G144V; S148N; A156V; L166V; D170V; C172Y; G183D; P205T; Y207C; Y207S; N215S; A228P; S235C; D244N; P259R; N263S; N264A; G272S; S276G; Q279E; Q279K; Q279H; M284T; W287C; I289F; M296I; M296V; L300P; R301Q; V316E; N320Y; G325D; G328A; R342Q; E358A; E358K; R363C; R363H; G370S; and P409A.

As used herein in one embodiment, the term "mutant GAA" includes a GAA which has a mutation in the gene encoding GAA which results in the inability of the enzyme to achieve a stable conformation under the conditions normally present in the ER. The failure to achieve a stable conformation results in a substantial amount of the enzyme being degraded, rather than being transported to the lysosome.

As used herein in one embodiment, the term "mutant Gba" includes a Gba which has a mutation in the gene encoding Gba which results in the inability of the enzyme to achieve a stable conformation under the conditions normally present in the ER. The failure to achieve a stable conformation results in a substantial amount of the enzyme being degraded, rather than being transported to the lysosome.

As used herein, the term "specific pharmacological chaperone" ("SPC") or "pharmacological chaperone" refers to any molecule including a small molecule, protein, peptide, nucleic acid, carbohydrate, etc. that specifically binds to a protein and has one or more of the following effects: (i) enhances the formation of a stable molecular conformation of the protein; (ii) induces trafficking of the protein from the ER to another cellular location, preferably a native cellular location, i.e., prevents ER-associated degradation of the protein; (iii) prevents aggregation of misfolded proteins; and/or (iv) restores or enhances at least partial wild-type function and/or activity to the protein. A compound that specifically binds to e.g., α-Gal A, GAA or Gba, means that it binds to and exerts a chaperone effect on the enzyme and not a generic group of related or unrelated enzymes. More specifically, this term does not refer to endogenous chaperones, such as BiP, or to non-specific agents which have demonstrated non-specific chaperone activity against various proteins, such as glycerol, DMSO or deuterated water, i.e., chemical chaperones (see Welch et al., *Cell Stress and Chaperones* 1996; 1(2):109-115; Welch et al., *Journal of Bioenergetics and Biomembranes* 1997; 29(5):491-502; U.S. Pat. Nos. 5,900,360; 6,270,954; and 6,541,195). In the present invention, the SPC may be a reversible competitive inhibitor.

A "competitive inhibitor" of an enzyme can refer to a compound which structurally resembles the chemical structure and molecular geometry of the enzyme substrate to bind the enzyme in approximately the same location as the substrate.

Thus, the inhibitor competes for the same active site as the substrate molecule, thus increasing the Km. Competitive inhibition is usually reversible if sufficient substrate molecules are available to displace the inhibitor, i.e., competitive inhibitors can bind reversibly. Therefore, the amount of enzyme inhibition depends upon the inhibitor concentration, substrate concentration, and the relative affinities of the inhibitor and substrate for the active site.

Following is a description of some specific pharmacological chaperones (SPCs) contemplated by this invention:

In one particular non-limiting embodiment, the SPC is 1-deoxygalactonorjirimycin which refers to a compound having the following structures:

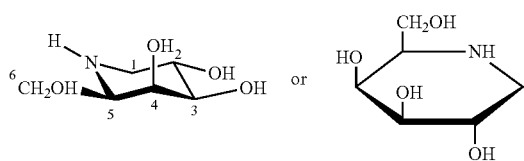

or a pharmaceutically acceptable salt, ester or prodrug of 1-deoxygalactonorjirimycin. The hydrochloride salt of DGJ is known as migalastat hydrochloride (Migalastat).

Still other SPCs for α-Gal A are described in U.S. Pat. Nos. 6,274,597, 6,774,135, and 6,599,919 to Fan et al., and include α-3,4-di-epi-homonojirimycin, 4-epi-fagomine, α-allo-homonojirimycin, N-methyl-deoxygalactonojirimycin, β-1-C-butyl-deoxygalactonojirimycin, α-galacto-homonojirimycin, calystegine $A_3$, calystegine $B_2$, calystegine $B_3$, N-methyl-calystegine $A_3$, N-methyl-calystegine $B_2$ and N-methyl-calystegine $B_3$.

In one particular non-limiting embodiment, the SPC is isofagomine (IFG; (3R,4R,5R)-5-(hydroxymethyl)-3,4-piperidinediol) which is represented by the following formula:

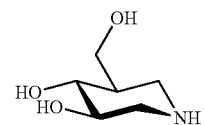

or a pharmaceutically acceptable salt, ester or prodrug of isofagomine, such as, for example, IFG tartrate (see, e.g., U.S. Patent Application Publication 20070281975.) IFG has a molecular formula of $C_6H_{13}NO3$ and a molecular weight of 147.17. This compound is further described in U.S. Pat. No. 5,844,102 to Sierks et al., and U.S. Pat. No. 5,863,903, to Lundgren et al.

Still other SPCs for Gba are described in U.S. Pat. No. 6,916,829 to Fan et al., and include C-benzyl isofagomine and derivatives, N-alkyl (C9-12)-DNJ, Glucoimidazole (and derivatives), C-alkyl-IFG (and derivatives), N-alkyl-β-valeinamines, Fluphenozine, N-dodecyl-DNJ, calystegines $A_3$, $B_1$, $B_2$ and $C_1$.

In one particular non-limiting embodiment, the SPC is 1-deoxynorjirimycin (1-DNJ), which is represented by the following formula:

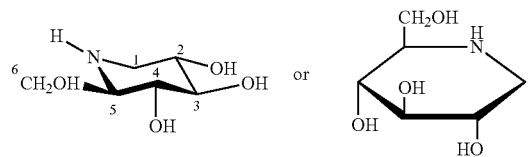

or a pharmaceutically acceptable salt, ester or prodrug of 1-deoxynorjirimycin. In one embodiment, the salt is hydrochloride salt (i.e. 1-deoxynojirimycin-HCl).

Still other SPCs for GAA are described in U.S. Pat. Nos. 6,274,597; 6,583,158; 6,599,919 and 6,916,829 to Fan et al., and U.S. Published Application No. 2006/0264467, and include N-methyl-DNJ, N-ethyl-DNJ, N-propyl-DNJ, N-butyl-DNJ, N-pentyl-DNJ, N-hexyl-DNJ, N-heptyl-DNJ, N-octyl-DNJ, N-nonyl-DNJ, N-methylcyclopropyl-DNJ, N-methylcyclopentyl-DNJ, N-2-hydroxyethyl-DNJ, 5-N-carboxypentyl DNJ, α-homonojirimycin, and castanospermine.

As used herein, the term "specifically binds" refers to the interaction of a pharmacological chaperone with a protein such as α-Gal A, Gba or GAA, specifically, an interaction with amino acid residues of the protein that directly participate in contacting the pharmacological chaperone. A pharmacological chaperone specifically binds a target protein, e.g., α-Gal A, Gba or GAA, to exert a chaperone effect on the protein and not a generic group of related or unrelated proteins. The amino acid residues of a protein that interact with any given pharmacological chaperone may or may not be within the protein's "active site." Specific binding can be evaluated through routine binding assays or through structural studies, e.g., co-crystallization, NMR, and the like. The active site for α-Gal A, Gba or GAA is the substrate binding site.

"Deficient α-Gal A activity" refers to α-Gal A activity in cells from a patient which is below the normal range as compared (using the same methods) to the activity in normal individuals not having or suspected of having Fabry or any other disease (especially a blood disease).

"Deficient Gba activity" refers to Gba activity in cells from a patient which is below the normal range as compared (using the same methods) to the activity in normal individuals not having or suspected of having Gaucher or any other disease.

"Deficient GAA activity" refers to GAA activity in cells from a patient which is below the normal range as compared (using the same methods) to the activity in normal individuals not having or suspected of having Pompe or any other disease.

As used herein, the terms "enhance α-Gal A activity," "enhance Gba activity," and "enhance GAA activity" or "increase α-Gal A activity," "increase Gba activity," and "increase GAA activity" refer to increasing the amount of α-Gal A, Gba or GAA, respectively, that adopts a stable conformation in a cell contacted with a pharmacological chaperone specific for the α-Gal A, Gba or GAA, relative to the amount in a cell (preferably of the same cell-type or the same cell, e.g., at an earlier time) not contacted with the pharmacological chaperone specific for the α-Gal A, Gba or GAA. This term also refers to increasing the trafficking of α-Gal A, Gba or GAA to the lysosome in a cell contacted with a pharmacological chaperone specific for the α-Gal A, Gba or GAA, relative to the trafficking of α-Gal A, Gba or GAA not contacted with the pharmacological chaperone specific for the protein. These terms refer to both wild-type and mutant α-Gal A, Gba or GAA. In one embodiment, the increase in the amount of α-Gal A, Gba or GAA in the cell is measured by measuring the hydrolysis of an artificial substrate in lysates from cells that have been treated with the SPC. An increase in hydrolysis is indicative of increased α-Gal A, Gba or GAA activity.

The term "α-Gal A activity" refers to the normal physiological function of a wild-type α-Gal A in a cell. For example, α-Gal A activity includes hydrolysis of GL-3.

The term "Gba activity" refers to the normal physiological function of a wild-type αGba in a cell. For example, Gba activity includes metabolism of fatty glucocerebrosides.

The term "GAA activity" refers to the normal physiological function of a wild-type Gaa in a cell. For example, GAA activity includes lysosomal glycogen metabolism.

A "responder" is an individual diagnosed with or suspected of having a lysosomal storage disorder, such, for example, but not limited to, Fabry disease, Pompe disease or Gaucher disease, whose cells exhibit sufficiently increased α-Gal A, GAA or Gba activity, respectively, and/or amelioration of symptoms or improvement in surrogate markers, in response to contact with an SPC. Non-limiting examples of improvements in surrogate markers for Fabry and Pompe disease are disclosed in U.S. Ser. Nos. 60/909,185 and 61/035,869, respectively.

Non-limiting examples of improvements in surrogate markers for Fabry disease disclosed in U.S. Ser. No. 60/909, 185 include increases in α-Gal A levels or activity in cells (e.g., fibroblasts) and tissue; reductions in of GL-3 accumulation; decreased plasma concentrations of homocysteine and vascular cell adhesion molecule-1 (VCAM-1); decreased GL-3 accumulation within myocardial cells and valvular fibrocytes; reduction in cardiac hypertrophy (especially of the left ventricle), amelioration of valvular insufficiency, and arrhythmias; amelioration of proteinuria; decreased urinary concentrations of lipids such as CTH, lactosylceramide, ceramide, and increased urinary concentrations of glucosylceramide and sphingomyelin (Fuller et al., *Clinical Chemistry*. 2005; 51: 688-694); the absence of laminated inclusion bodies (Zebra bodies) in glomerular epithelial cells; improvements in renal function; mitigation of hypohidrosis; the absence of angiokeratomas; and improvements hearing abnormalities such as high frequency sensorineural hearing loss progressive hearing loss, sudden deafness, or tinnitus. Improvements in neurological symptoms include prevention of transient ischemic attack (TIA) or stroke; and amelioration of neuropathic pain manifesting itself as acroparaesthesia (burning or tingling in extremities).

The dose that achieves one or more of the aforementioned responses is a "therapeutically effective dose."

The phrase "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an mRNA band on a gel, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acids include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

Method of Determining Treatment Options

To easily determine whether SPC therapy will be a viable treatment for patients, for example, Fabry, Pompe or Gaucher patients, and including female carriers of X-linked lysosomal storage disorders such as Fabry disease, a simple, non-invasive SPC rescue assay of protein activity in a cell line expressing a mutant form of the protein was developed.

In vitro Assay

In one embodiment, the diagnostic method of the present invention involves transforming a cell line with a nucleic acid vector which encodes a mutant lysosomal enzyme, for example, α-Gal A, GAA or Gba. The cell line is then treated with or without an SPC, e.g., DGJ, DNJ or IFG, for a sufficient time period to demonstrate enhancement (i.e., increase) of α-Gal A, GAA or Gba activity. The transformed cells are then lysed, and the lysate is used in an assay to determine enzyme activity. A sufficient increase in α-Gal A, GAA or Gba activity in the lysates from cells treated with the SPC over the activity in the lysates from untreated cells indicates that a patient who expresses α-Gal A, GAA or Gba with the same mutation as the cell line will likely respond to SPC therapy (i.e., the patient will be a "responder").

Transient Transfection of a Cell Line and Expression of a Mutant Lysosmal Enzyme In one embodiment, to identify SPC-responsive mutations, all known lysosomal enzyme (e.g., α-Gal A, GAA or Gba) mutations, for example, missense mutations and in-frame small deletions and insertions, can be generated according to techniques known in the art, for example, by site-directed mutagenesis. Mutant enzyme constructs can then be transiently expressed in a cell line, for example, mammalian COS-7, HEK-293 or GripTite 293 MSR (Invitrogen Corp., Carlsbad, Calif., U.S.A.) cells. Transformed cells can then be incubated with increasing concentrations of SPC and enzymatic activity can be measured in cell lysates.

Mutagenesis: Nucleic acid vectors encoding a mutant protein (e.g. mutant α-Gal A, GAA or Gba) can be generated by conventional molecular biology, microbiology, and recombinant DNA techniques within the skill of the art. Such techniques are explained fully in the literature. (See, e.g., Sambrook, Fritsch & Maniatis, 2001, Molecular Cloning: A Laboratory Manual, Third Edition, Cold Spring Harbor Laboratory Press, Cold Spring Harbor, N.Y.; Glover, ed., 1985, DNA Cloning: A Practical Approach, Volumes I and II, Second Edition; Gait, M. J., ed., 1984, Oligonucleotide Synthesis: A practical approach; Hames, B. D. & Higgins, S. J. eds., 1985, Nucleic Acid Hybridization; Hames, B. D. & Higgins, S. J., eds., 1984, Transcription And Translation; Freshney, R. I., 2000, Culture of Animal Cells: A Manual of Basic Technique; Woodward, J., 1986, Immobilized Cells And Enzymes: A practical approach, IRL Press; Perbal, B. E., 1984, A Practical Guide To Molecular Cloning). For example, a single α-Gal A, GAA or Gba mutation can be introduced into a nucleic acid encoding a wild type α-Gal A, GAA or Gba gene through site directed mutagenesis of a nucleic acid encoding the wild type enzyme.

Transient transfection and expression: The coding sequences of the gene to be delivered, for example, a mutant α-Gal A, GAA or Gba, are operably linked to expression control sequences, e.g., a promoter that directs expression of the gene. As used herein, the phrase "operatively linked" refers to the functional relationship of a polynucleotide/gene with regulatory and effector sequences of nucleotides, such as promoters, enhancers, transcriptional and translational stop sites, and other signal sequences. For example, operative linkage of a nucleic acid to a promoter refers to the physical and functional relationship between the polynucleotide and the promoter such that transcription of DNA is initiated from the promoter by an RNA polymerase that specifically recognizes and binds to the promoter. The promoter directs the transcription of RNA from the polynucleotide. Expression of a mutant protein (e.g. mutant α-Gal A, GAA or Gba) may be controlled by any promoter/enhancer element known in the art, but these regulatory elements must be functional in the host selected for expression.

In one specific embodiment, a vector is used in which the coding sequences and any other desired sequences are flanked by regions that promote homologous recombination at a desired site in the genome, thus providing for expression of the construct from a nucleic acid molecule that has integrated into the genome (See Koller and Smithies, 1989, Proc. Natl. Acad. Sci. USA, 86:8932-8935; Zijlstra et al., 1989, Nature 342:435-438; U.S. Pat. No. 6,244,113 to Zarling et al.; and U.S. Pat. No. 6,200,812 to Pati et al.).

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. In one embodiment, a host cells that is transfected with a vector encoding a mutant α-Gal A, GAA or Gba can be used for screening a candidate SPC, for example, DGJ, DNJ or IFG, to determine if the candidate SPC is an effective compound for increasing the activity of the mutant α-Gal A, GAA or Gba expressed by the host cell.

The term "expression system" means a host cell and compatible vector under suitable conditions, e.g., for the expression of a protein coded for by foreign DNA carried by the vector and introduced to the host cell. Expression systems include mammalian host cells and vectors. Suitable cells include PC12 cells, CHO cells, HeLa cells, GripTite 293 MSR cells (Invitrogen Corp., Carlsbad, Calif., U.S.A.), HEK-293 (also known as 293 cells) and 293T cells (derived from human embryonic kidney cells), COS cells (e.g. COS-7 cells), mouse primary myoblasts, NIH 3T3 cells.

Suitable vectors include viruses, such as adenoviruses, adeno-associated virus (AAV), vaccinia, herpesviruses, baculoviruses and retroviruses, parvovirus, lentivirus, bacteriophages, cosmids, plasmids, fungal vectors, naked DNA, DNA lipid complexes, and other recombination vehicles typically used in the art which have been described for expression in a variety of eukaryotic and prokaryotic hosts, and may be used for gene therapy as well as for simple protein expression.

In one non-limiting example, transient transfection can be carried out in GripTite 293 MSR cells (Invitrogen Corp., Carlsbad, Calif., U.S.A.) using the reagent Fugene HD (Roche). The cells can be seeded in a suitable assay container, such as a 96-well plate (Costar) at a density of, for example, 7.5-10k cells/well, and incubated under suitable conditions, such as, for example, 37° C., 5% $CO_2$ for 24 hours before transfection. After transfection with expression constructs containing a specific α-Gal A mutant, cells can be incubated again in, for example, 37° C., 5% $CO_2$ for one hour before adding DGJ at 50 nM to 1 mM. Cells can then be incubated for 4-5 days before lysis and assay.

Enzyme Activity/Enhancement Assay: Typically, following incubation with an SPC (e.g. DGJ, DNJ or IFG), host cells are lysed by the addition of lysis buffer (or deionized water) and physical disruption (pipetting, vortexing and/or agitation, and/or sonication) at room temperature or on ice, followed by pooling of the lysates on ice, then splitting the pooled lysate into small aliquots and freezing.

The lysates can be thawed immediately prior to the assay and should be suspended by use of a vortex mixer and sonicated prior to addition to appropriate wells e.g., in a microplate. In the context of Fabry disease, N-acetylgalactosamine (GalNAc) is then added to each well (to inhibit α-galactosidase B), followed by a short incubation. 4-methylumbelliferyl-α-D-galactopyranoside (4-MU Gal), or other appropriate labeled DGJ substrate, is then added and the plate is gently mixed for a brief period of time, covered, and incubated at 37° C. for a sufficient time for substrate hydrolysis, usually about 1 hour. To stop the reaction, NaOH-glycine buffer, pH 10.7, is added to each well and the plate is read on a fluorescent plate reader (e.g. Wallac 1420 Victor3™ or similar instrument). Excitation and emission wavelengths were customarily set at 355 nm and 460 nm, respectively. One unit of enzyme activity is defined as the amount of enzyme that catalyzes the hydrolysis of 1 nmole of 4-methylumbelliferone per hour. For each patient sample at least three normal samples may be tested concurrently.

Various modifications of this assay will be readily ascertainable to one of ordinary skill in the art. Examples of artificial substrates that can be used to detect α-Gal A activity include but are not limited to p-nitrophenyl-α-D-galactopyranoside and 4-MU GAL. Obviously, only substrates that can be cleaved by human α-Gal A are suitable for use. It is noted that while use of a fluorogenic substrate is preferred, other methods of determining enzymatic activity are contemplated for use in the method, including using chromogenic substrates or immunoquantification techniques.

In one specific example, following incubation with an SPC, for example, DGJ, the host cells can be washed two times with PBS then incubated in 200 μl fresh media at 37° C., 5% $CO_2$ for two hours followed by 2 additional PBS washes. After, cells can be lysed in 60 μL Lysis Buffer (27 mM sodium citrate/46 mM sodium phosphate dibasic, 0.5% Triton X-100, pH 4.6). Ten μL lysate can then be added to 50 μL assay buffer (Lysis Buffer without Triton X-100, but containing 6 mM 4-MU-α-D-galactopyranoside (4-MUG) and 117 mM N-acetyl-D-galactosamine (GalNac)), and incubated at 37° C. for 1 hr. Seventy μL Stop Solution (0.4 M glycine, pH 10.8) can then be added and fluorescence read on a Victor plate reader (Perkin Elmer) at 355 nm excitation and 460 nm emission. Raw fluorescence counts can be background subtracted as defined by counts from substrate solution only. A MicroBCA Protein Assay Kit (Pierce) was used according to manufacturer's instructions to determine protein concentration from 40 μL of cell lysate. A 4-methylumbelliferone (4-MU) standard curve ranging from 30 μM to 1.3 nM was run in parallel for calculation of absolute α-Gal A activity expressed as nmoles/mg protein/hr or further normalized to % of untreated wild type enzyme activity.

Treatment Reference Table

In another embodiment, the methods described supra can be used to generate a "treatment reference table" or "treatment therapy table," wherein the treatment reference table comprises a list of protein mutations, and further wherein the table indicates the responsiveness of each mutation to an SPC, such as DGJ, DNJ or IFG. The treatment reference table can then be used to determine if a particular SPC, for example, DGJ, DNJ or IFG, would be an effective SPC for treating a patient with a particular α-Gal A, GAA or Gba mutation, respectively.

As used herein "treatment therapy table" or "treatment reference table" refers to any written record that conveys whether a particular mutation is responsive to SPC therapy, and is not necessarily limited to written records presented in tabular form.

In one embodiment, the treatment reference table can be used by a treating physician or clinical professional to select an SPC for treating a patient, for example, a Fabry, Pompe or Gaucher patient who expresses a specific mutant α-Gal A, GAA or Gba, respectively, wherein the SPC is selected because the treatment reference table identifies the SPC as a compound that can increase the activity of the patient's mutant α-Gal A, GAA or Gba when the mutant α-Gal A, GAA or Gba is expressed in a host cell.

Treatable Disorders

While the present application has been discussed largely in the context of Fabry, Pompe and Gaucher diseases, and the SPCs DGJ, DNJ and IFG, respectively, it should be understood that it is applicable to any SPC and disease. In one non-limiting embodiment, a treatment reference table can be generated for any candidate SPC and any lysosomal storage disorder, or any disorder involving protein misfolding. These diseases include other lysosomal storage disorders, for example, Cystic Fibrosis (CFTR) (respiratory or sweat gland epithelial cells), familial hypercholesterolemia (LDL receptor; LPL-adipocytes or vascular endothelial cells), cancer (p53; PTEN-tumor cells), Alzheimer's disease (α-secretase), Parkinson's disease (glucocerebrosidase), obesity (MC4R), and amyloidoses (transthyretin) among others.

Eligibility Determination Criteria

The criteria for determining eligibility for SPC therapy depends on the type of mutant GLA, GAA or Gba a patient expresses. In one embodiment, patients with Fabry, Pompe, or Gaucher disease could be categorized as eligible for SPC therapy if α-Gal A, GAA or Gba activity, respectively, in a host cell expressing the same mutation as the patient, in the presence of an SPC such as DGJ, DNJ or IFG, is at least about 1.5- to 20-fold (2% to 100%) activity of a host cell expressing a wild type α-Gal A, GAA or Gba.

This discovery provides a method for improving the diagnosis of and facilitating clinical treatment decisions for Fabry, Pompe and Gaucher diseases in particular, and lysosomal storage disease in general. Moreover, this method can be extended to a wide range of genetically defined diseases in appropriate cell types. This class of disease includes the other lysosomal storage disorders, Cystic Fibrosis (CFTR) (respiratory or sweat gland epithelial cells), familial hypercholesterolemia (LDL receptor; LPL-adipocytes or vascular endothelial cells), cancer (p53; PTEN-tumor cells), Alzheimer's disease (α-secretase), Parkinson's disease (glucocerebrosidase), obesity (MC4R), and amyloidoses (transthyretin) among others.

Kits

The present invention also provides for a commercial diagnostic test kit in order to make therapeutic treatment decisions. The kit provides all materials discussed above and more particularly in the Examples below, for preparing and running each assay in one convenient package, optionally including instructions and an analytic guide.

As one non-limiting example, a kit for evaluating α-Gal A activity may contain, at a minimum:
  a. a panel of host cells, each expressign a mutant α-Gal A, or alternatively, a host cell, a vector encoding a mutant α-Gal A, and a means of transfecting the host cell such that the host cell expresses the mutant α-Gal A;
  b. a specific pharmacological chaperone;
  c. a chromogenic or fluorogenic substrate for the enzyme assay (including an appropriate standard); and
  d. GalNAc.

The kit may also contain instructions for optimally performing the protein enhancement assay. In another embodiment, the kit will contain the appropriate tubes, buffers (e.g., lysis buffer), and microplates.

In one embodiment, the SPC is supplied in dry form, and will be re-constituted prior to addition.

Patients who express a mutant α-Gal A, GAA or Gba that previously tested positive for enzyme enhancement with a candidate SPC in assays of the present Mention can then be treated with that candidate SPC agent, whereas patients who express a mutant α-Gal A, GAA or Gba that does not display enzyme enhancement with a candidate SPC can avoid treatment which will save money and prevent the emotional toll of not responding to a treatment modality.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1

Identification of Fabry Disease-Causing Mutations that are Responsive to the Pharmacological Chaperone DGJ The present Example provides the in vitro diagnostic assay to determine a Fabry patient's responsiveness to a specific pharmacological chaperone.

Introduction

Fabry disease is a lysosomal storage disorder caused by mutations in the gene that encodes α-galactosidase A (α-GAL A). Over 600 Fabry mutations have been reported, and about 60% are missense. The iminosugar DGJ is currently being studied in Phase 2 clinical trials as a pharmacological chaperone for the treatment of Fabry disease. Previously, it has been shown that DGJ mediates selective and dose-dependent increases in α-Gal A levels in many Fabry patient-derived lymphoid cell lines. To identify additional DGJ-responsive mutations, GripTite 293 MSR, (Invitrogen Corp., Carlsbad, Calif., U.S.A.) cells were transiently transfected with expression vectors containing all known α-Gal A missense mutations and several in-frame small deletions and insertions generated by site-directed mutagenesis. Mutant α-Gal A constructs were transiently expressed in HEK-293 cells. Cells were incubated with increasing concentrations of DGJ and α-Gal A activity was measured in cell lysates. Assay validation has been carried out on more than 35 missense mutations and the results obtained in HEK-293 cells were similar to those obtained from both Fabry patient-derived lymphoid cells and primary T-cell cultures (see U.S. Ser. No. 11/749,512), as well as to the α-Gal A enzyme responses observed in the white blood cells of Fabry patients after oral administration of DGJ in Phase 2 clinical trials.

Methods and Materials

Mutagenesis: All mutations were generated by site-directed mutagenesis following standard molecular biology protocols. To generate point mutations, site-directed mutagenesis was used on the expression vector pcDNA3.1 (Invitrogen) containing human α-GAL A cDNA in-frame. Specific primer pairs were designed containing the desired mutation (FIG. 6). The mutagenesis was performed through the polymerase chain reaction using PfuUltra high-fidelity DNA polymerase (Stratagene) in a thermocycler. Each reaction mixture contained a total volume of 50 µl with the following: 41.6 ul dH$_2$O, 5.0 ul 10×PfuUltra HF reaction buffer, 0.5 uL Forward-5'-primer (50 uM), 0.5 ul Reverse-3'-primer, 1.0 ul dNTP mix (containing 25 mM each dA, dT, dC, dG), 0.9 ul human GLA in pcDNA3 (2 ng/ul DNA), 0.5 ul PfuUltra HD DNA polymerase. Thermocycler parameter used was the following: i) 94° C. for 30 seconds, ii) 94° C. for 30 seconds, 55-60° C. for 30 seconds, 68° C. for 6 minutes, iii) Repeat (ii) 16 times. Afterwards, 0.5 ul Dpn 1 (New England Biolabs) was added to each reaction and incubated at 37° C. for 2 hours. A volume of 7.5 ul for each mutagenesis reaction was used to transform DH5a cells (New England Biolabs). Cells were then plated on LB-agar plates with 75 ug/ml ampicillin, and incubated at 37° C. overnight. Bacterial colonies were picked, grown in liquid LB with ampicillin overnight, shaking, at 37° C., and plasmid DNA extracted using QuickLyse Miniprep Kit (Qiagen). Mutants were confirmed by sequencing the full-length human GLA gene. For some of the mutants, human GLA cDNA was contained in the vector plasmid pCXN. Mutagenesis was performed in this vector with the NEB Fusion DNA polymerase. After confirming the mutation through sequencing, the plasmid was digested with EcoRI and subcloned into expression vector pcDNA3.1. Correct orientation was confirmed by digestion with Xho I.

Transient transfection and expression: Transient transfection was carried out in GripTite 293 MSR cells (Invitrogen Corp., Carlsbad, Calif., U.S.A.) using the reagent Fugene HD (Roche). Briefly, cells were seeded in 96-well plates (Costar) at a density of 7.5-10k cells/well and incubated at 37° C., 5% CO$_2$ for 24 hours before transfection. Cells were transfected with 0.1 µg DNA and 0.35 µL of Fugene HD reagent per well (DNA: Reagent ratio of 2:7). After transfection with expression constructs containing the specific α-Gal A mutants, cells were incubated again in 37° C., 5% CO$_2$ for one hour before adding DGJ at 20 nM to 1 mM. Cells were then incubated for 4-5 days before lysis and assay.

α-GAL A activity measurement: Cells were washed two times with PBS then incubated in 200 µl fresh media at 37° C., 5% CO$_2$ for two hours followed by 2 additional PBS washes. After, cells were lysed in 60 µL Lysis Buffer (27 mM sodium citrate/46 mM sodium phosphate dibasic, 0.5% Triton X-100, pH 4.6). Ten µL lysate were added to 50 µL assay buffer (Lysis Buffer without Triton X-100, but containing 6 mM 4-MU-α-D-galactopyranoside (4-MUG)

and 117 mM N-acetyl-D-galactosamine (GalNac)), and incubated at 37° C. for 1 hr. Seventy μL Stop Solution (0.4 M glycine, pH 10.8) were then added and fluorescence read on a Victor plate reader (Perkin Elmer) at 355 nm excitation and 460 nm emission. Raw fluorescence counts were background subtracted as defined by counts from substrate solution only. A MicroBCA Protein Assay Kit (Pierce) was used according to manufacturer's instructions to determine protein concentration from 40 μL of cell lysate. A 4-methylumbelliferone (4-MU) standard curve ranging from 30 μM to 1.3 nM was run in parallel for calculation of absolute α-Gal A activity expressed as nmoles/mg protein/hr or further normalized to % of untreated wild type enzyme activity.

Transient transfection and α-Gal A activity measurements were performed in quadruplicates and repeated at least 3 times for each mutation to calculate the average α-Gal A activity at each DGJ concentration. Significant response to DGJ was determined by a two-tailed, paired Student's T-test ($p<0.05$).

Results

Figure 4:
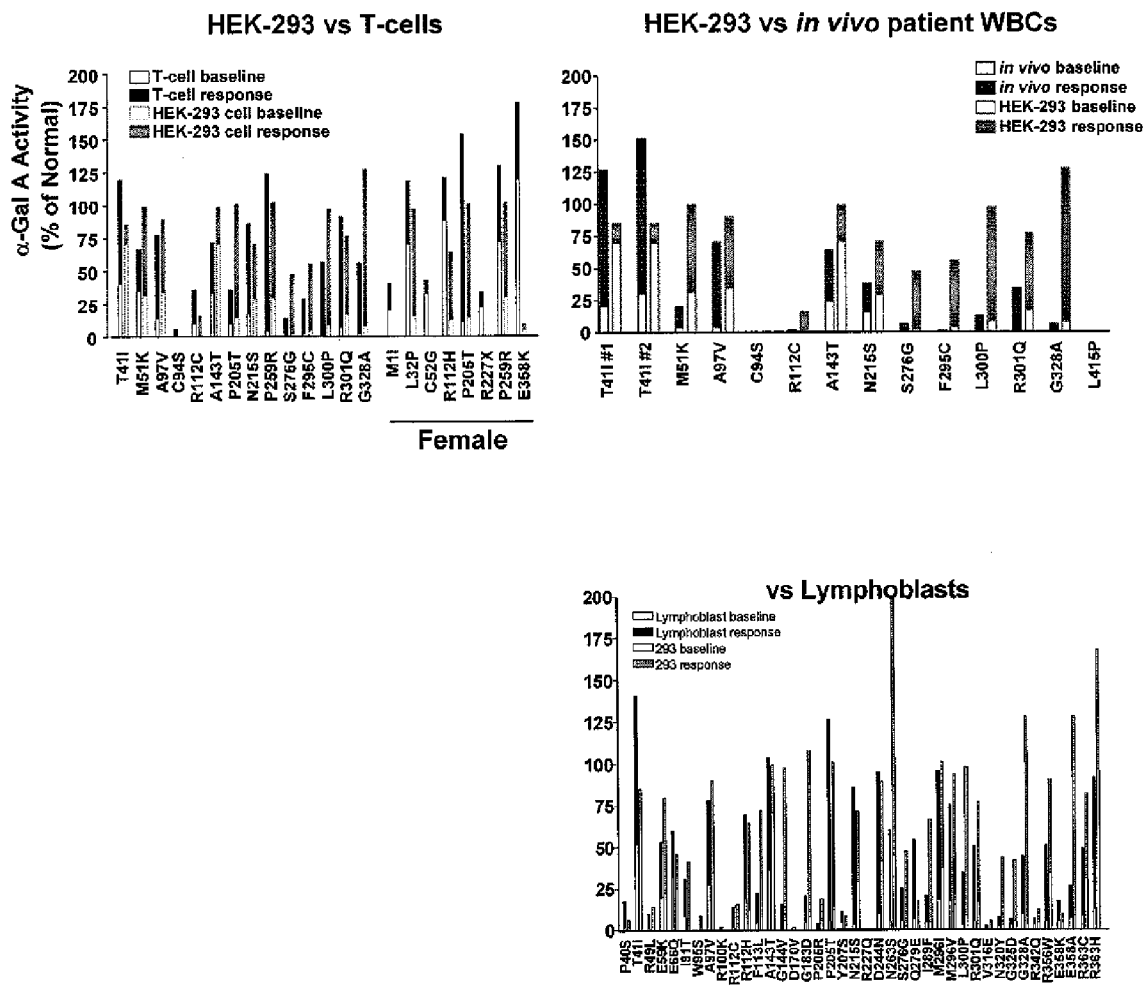
FIG. 4 Shows that the mutation response in HEK 293 cells are comparable to patient-derived T-cells, lymphoblasts or white blood cells in vivo. α-Gal A levels measured in three different assays, reported as percentage of wild type, are compared for each mutation examined. α-Gal A levels were measured in T-Cells, lymphoblasts, white blood cells and HEK 293 cells expressing mutant α-Gal A before and after exposure to DGJ. Blank bars indicate basal level (without DGJ treatment) and filled bars indicate the elevated level after DGJ treatment.

All listed Fabry mutations were generated by site-directed mutagenesis (FIG. 1). Mutations identified in italicized text were not tested, while those identified in plain text were α-Gal A mutants that were responsive to DGJ treatment in the transient transfection assay, and those identified in bold and underscored text were not responsive to DGJ treatment in the transient transfection assay. The magnitude of increase in α-Gal A levels after DGJ treatment and EC50 values are listed for every tested mutation that responded to DGJ treatment (FIG. 2).

α-Gal A activity (expressed as nmol/mg protein/hr of 4-MU released) was measured in lysates prepared from transfected GripTite 293 cells incubated with increasing concentrations of DGJ. A typical concentration-dependent response is shown for L300P and a typical negative response to DGJ is shown for R227Q. Wild type exhibits high baseline activity and does not respond to DGJ in this assay (FIG. 3).

α-Gal A levels were measured in three different assays, reported as percentage of wild type, are compared for each mutation by plotting side by side. The three different assays examined α-Gal A levels in T-cells and lymphoblasts isolated from Fabry patients (for example, see U.S. Ser. No. 11/749,512), as well as in white blood cell (WBC) from DGJ Phase 2 studies Blank bars indicate basal level (without DGJ treatment) and filled bars indicate the elevated level after DGJ treatment (FIG. 4).

Figure 5:
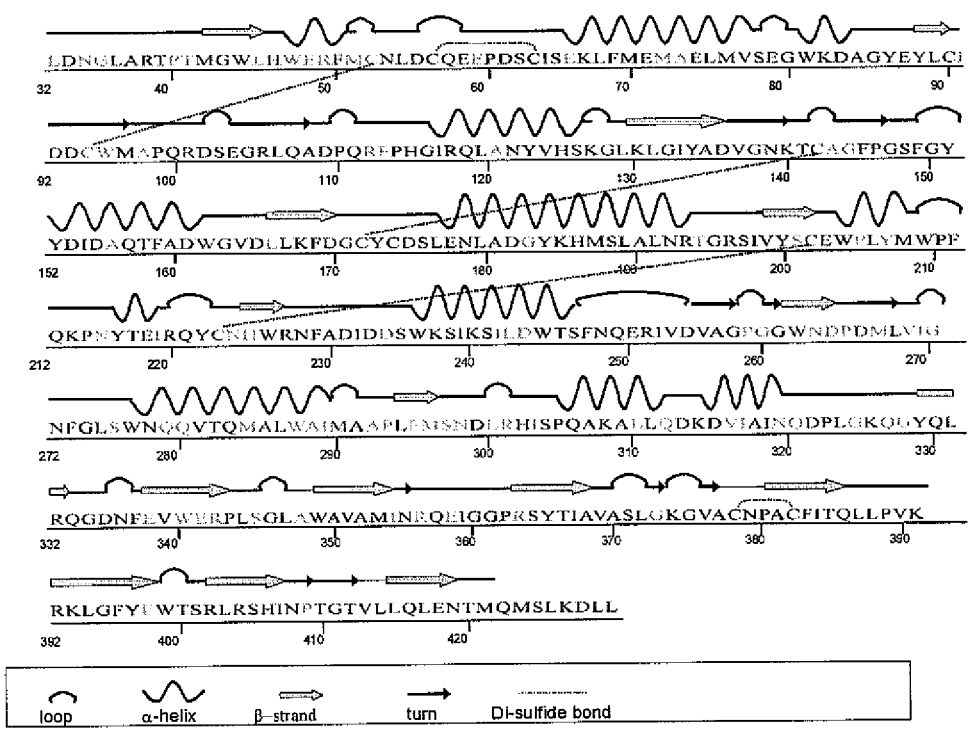
FIG. 5 Shows that DGJ-responsive α-Gal A mutations are widely distributed on the α-Gal A protein sequence. Tested Fabry mutations are illustrated on the α-Gal A secondary structure. No significant correlation between response and location on the protein sequence of a mutation was observed, suggesting that responsive as well as non-responsive mutations are distributed widely across the entire protein. Text color indicates DGJ response: green=response; red=no response; brown indicates that of the multiple mutations on that same site some responded to DGJ treatment, while others did not.

Tested Fabry mutations were illustrated on the α-Gal A secondary structure (FIG. 5). No significant correlation between response and location on the protein sequence of a mutation was observed, suggesting that responsive as well as non-responsive mutations are distributed widely across the entire protein. Text color indicates DGJ response: green=response; red=no response; brown indicates that of the multiple mutations on that same site some responded to DGJ treatment, while others did not.

Conclusion

These described results are comparable to those obtained from Fabry patient-derived lymphoid or T cells, as well as to the α-Gal A enzyme responses observed in the white blood cells of Fabry patients after oral administration of DGJ in Phase 2 clinical trials.

Thus, the GripTite 293 MSR transient transfection assay is a reliable method for identifying DGJ-responsive mutations and characterizing the magnitude and potency of this response.

Among the responsive mutations identified, the increases in α-Gal A levels by DGJ treatment ranged from 1.3- to 40-fold (2% to 100% wild type), with $EC_{50}$ values between 200 nM and >100 mM.

DGJ-responsive and non-responsive mutant forms did not appear to be located to particular regions or domains on the α-Gal A protein structure.

Example 2

Ex vivo Method for Evaluating Effects of an SPC on Glucocerebrosidase Activity—Prophetic Example Gaucher disease (GD) is caused by a deficiency of lysosomal glucocerebrosidase (GCase). Deficient GCase activity leads to an accumulation of glucosylceramide (GlcCer) and the development of symptoms such as anemia, thrombocytopenia, hepatosplenomegaly, bone necrosis, infarcts and osteoporosis, and in some cases, neuropathic disease. The specific pharmacological chaperone isofagomine tartrate (IFG) selectively binds and stabilizes mutant (N370S/N370S) GCase in the ER and increases its trafficking to the lysosome.

To evaluate the effects of IFG on different GCase variants, an ex vivo diagnostic assay will be prepared using Cos7 cells in order to ascertain IFG-responsive mutations.

Using the techniques described in Examples 1 and 4, COS-7 cell lines will be prepared that express missense mutations and several in-frame small deletions and insertions by site-directed mutagenesis. Assays will be prepared for all of the mutations listed in the x-axis of FIG. 8. IFG-activity response will be ascertained for each assay according to methods known in the art (see, e.g., U.S. Pat. No. 6,916,829, which is hereby incorporated by reference).

Figure 8:
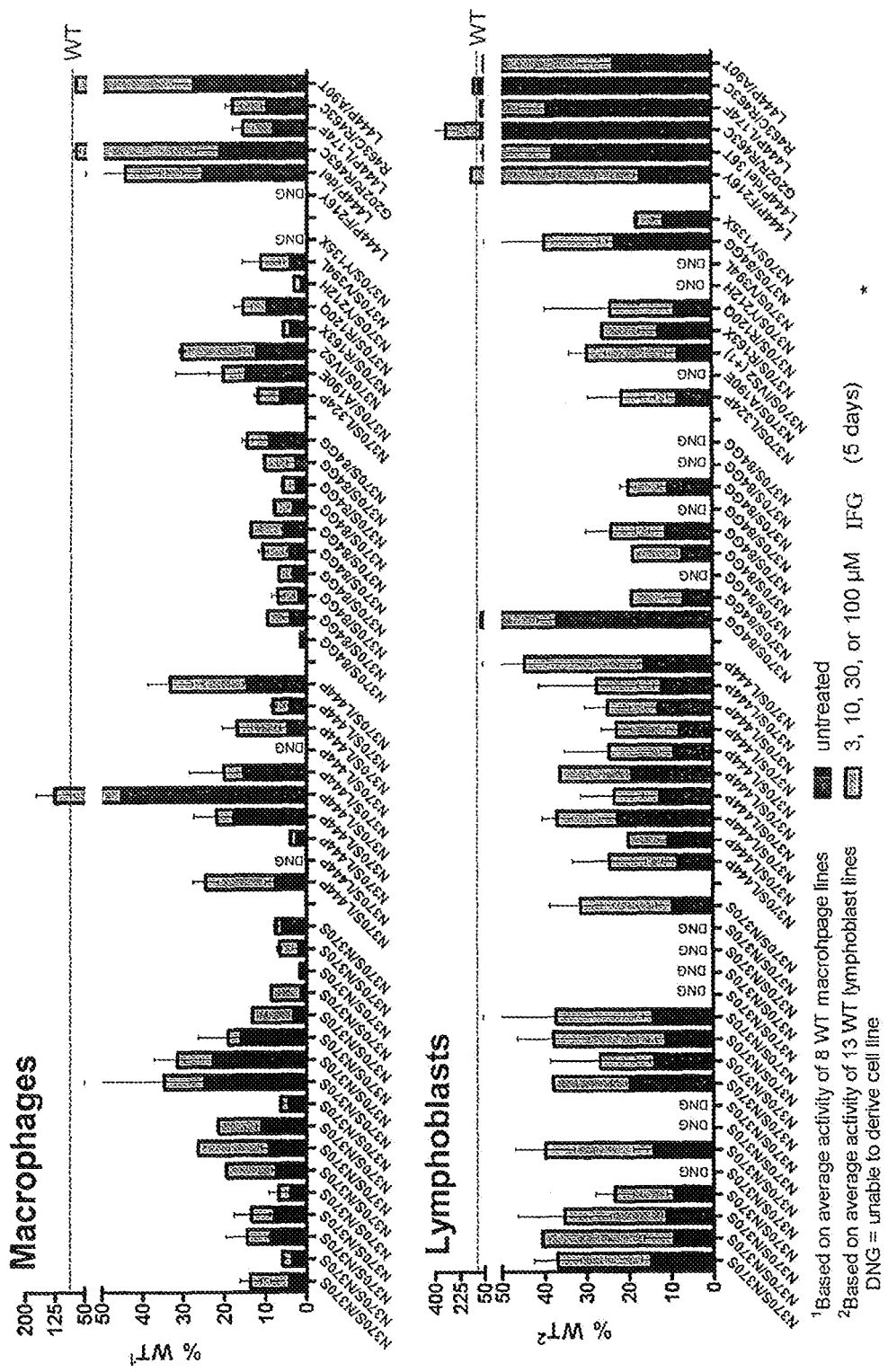
FIG. 8 Shows the effect of isofagomine tartrate on patient-derived macrophages and lymphoblasts isolated from Gaucher disease patients with different mutations in their glucocerebrosidase (Gba; GCase) enzyme.

To determine the correlation of the IFG-response measured in the COS-7 cells to patient-derived cells, IFG-activity response was also measured in Patient-Derived Macrophages and Lymphoblasts. Macrophages were successfully derived from 46 of 63 patients and incubation with IFG (3, 10, 30 or 100 μM) for 5 days increased GCase levels in macrophages from 42 of 46 patients (mean=2.3-fold; range: 1.1- to 6.5-fold). Residual activity levels and response to IFG was more consistent for the same genotypes when measured in lymphoblasts compared to macrophages, potentially due to the variability in macrophage viability between different patients. The results are shown in FIG. 8.

The response to IFG for the patient-derived cells will be compared to the results obtained in the Cos7 cell line.

Example 3

In vivo Effect of an SPC on α-GAL A Activity in Skin, Heart, Kidney and Plasma

To determine if increased mutant α-Gal A levels translate to increased α-Gal A activity in situ, the effect of DGJ administration on tissue GL-3 levels was investigated in vivo in hR301Q α-Gal A Tg/KO mice.

Eight-week old male hR301Q α-Gal A Tg/KO mice were treated for 4 weeks with 300 mg/kg DGJ in drinking water either daily or less frequently (4 days ON/3 days OFF). After dosing, lysates were prepared from skin, heart, kidney, and plasma by homogenizing ~50 mg tissue in Lysis Buffer (see above). 20 μL lysate were mixed with 50 μL of substrate (as detailed above). Reaction mixtures were incubated at 37° C. for 1 hr. After, 70 Stop Solution were added and fluorescence was read on a Victor plate reader as described above. Enzyme activity in the lysates was background subtracted, and normalized for protein concentration. A 4-MU standard curve was run for conversion of fluorescence data to absolute α-Gal A activity expressed as nmol/mg protein/hr.

Tissue samples were washed free of blood, weighed and homogenized with a solvent system in a FastPrep® system. Homogenate was then extracted using Solid Phase Extraction on a C18 cartridge. The eluent was evaporated and reconstituted prior to injection onto a LC-MS/MS system. Twelve GL-3 isoforms were measured using positive ESI-MS/MS. LC separation was achieved on 00839a Zorbax C18 column.

Figure 9:
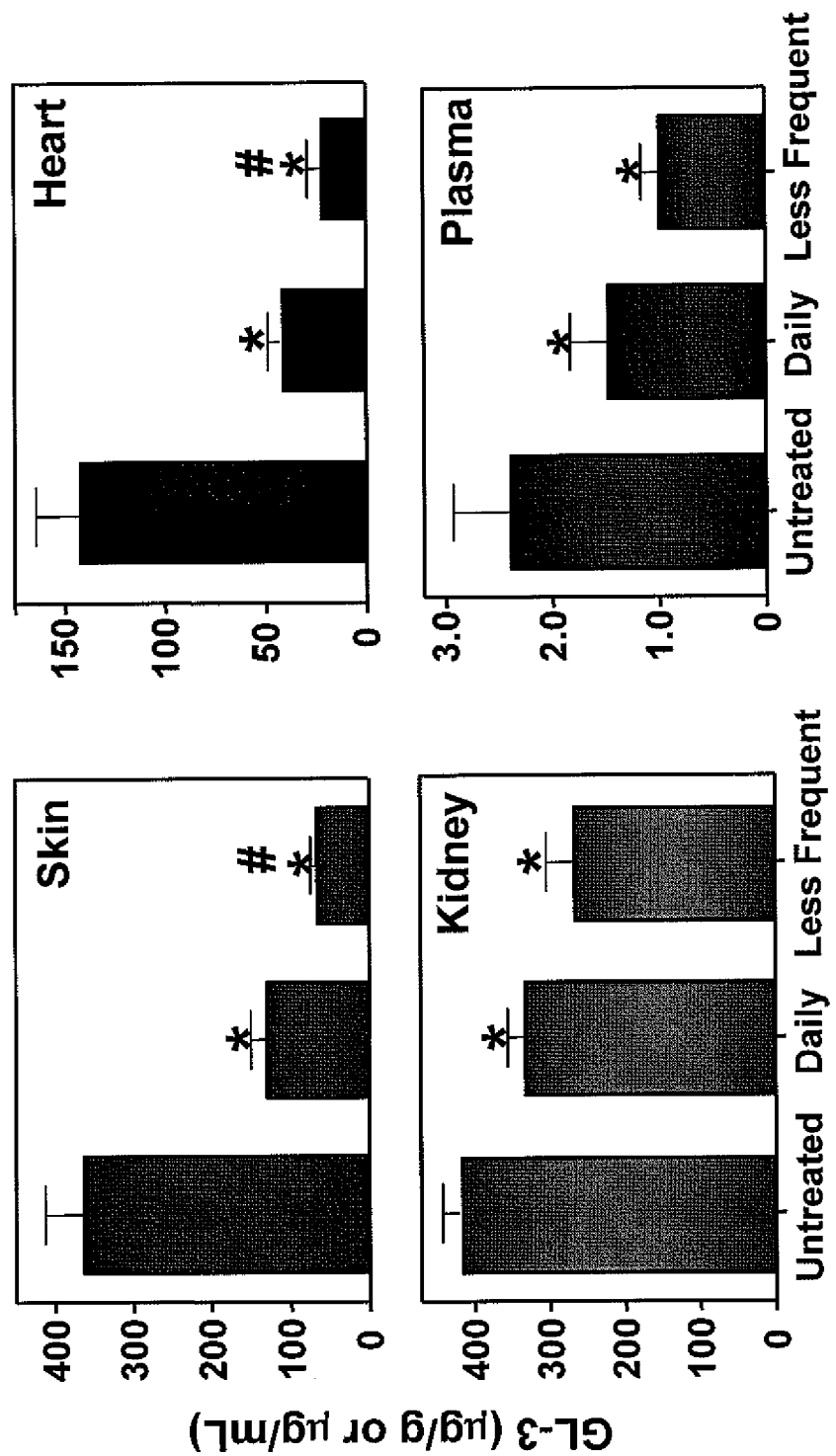
FIG. 9 Shows the effect on GL-3 levels of eight-week old male hR301Q α-Gal A Tg/KO mice which were treated for 4 weeks with 300 mg/kg DGJ in drinking water either daily or less frequently (4 days ON/3 days OFF).

Significant decreases in GL-3 levels were seen with daily and less frequent DGJ dosing in skin, heart, kidney, and plasma (FIG. 9). A trend of greater reduction in GL-3 levels was seen in multiple tissues and plasma with less frequent DGJ dosing. Collectively, these results indicate that DGJ merits further evaluation for the treatment of patients with Fabry disease.

Example 4

Identification of Pompe Disease-Causing Mutations that are Responsive to the Pharmacological Chaperone DNJ Pompe disease is caused by deficient acid alpha glucosidase (GAA) activity which impairs lysosomal glycogen metabolism. The enzyme deficiency leads to lysosomal glycogen accumulation and results in progressive skeletal muscle weakness, reduced cardiac function, respiratory insufficiency, and CNS impairment at late stages of disease. Genetic mutations in the GAA gene result in either lower expression or produce mutant forms of the enzyme with altered stability, and/or biological activity ultimately leading to disease. Pharmacological chaperones represent a promising new therapeutic approach for the treatment of genetic diseases.

Figure 12:
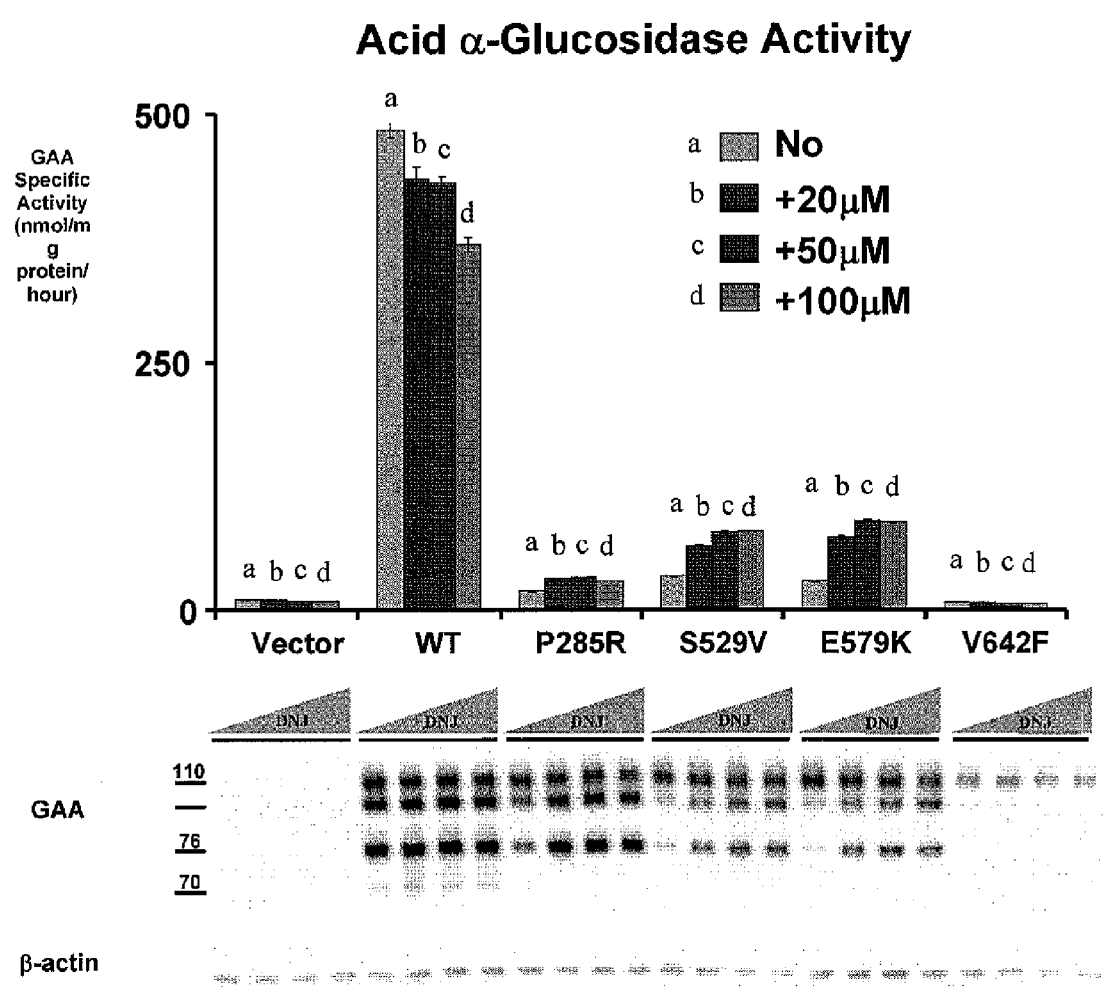
FIG. 12 Shows the responsiveness of four different GAA mutations to DNJ treatment at concentrations of 0 μM, 20 μM, 50 μM and 100 μM. The increase in enzyme activity is shown as specific activity (nmol/mg protein/hour).
Figure 14:
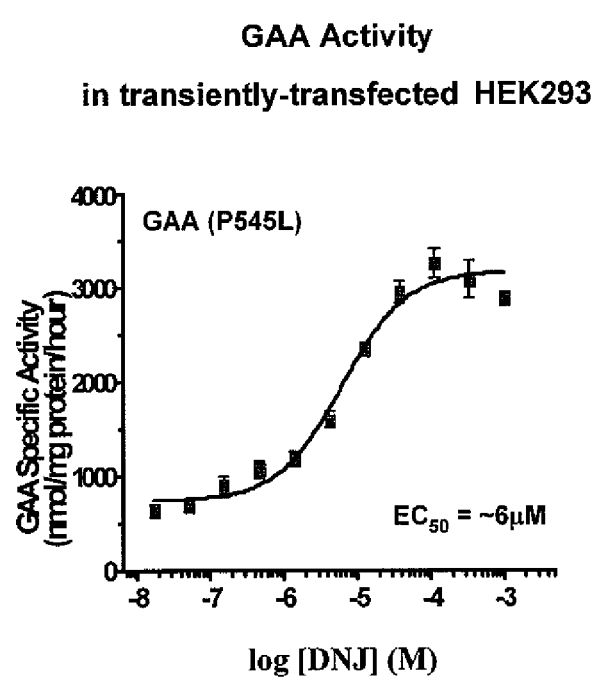
FIG. 14 Shows the $EC_{50}$ for DNJ induced GAA activity in HEK-293 cells transiently transfected with the P545L GAA mutation.

To evaluate the effects of DNJ on different GAA variants, an in vitro diagnostic assay was prepared using COS-7 and HEK-293 cells in order to ascertain DNJ-responsive mutations (FIGS. 10, 12 and 14)

A site-directed mutagenesis approach was employed to introduce specific mutations into the complementary DNA (cDNA) encoding wild-type human acid α-glucosidase (GAA). The initial wild-type GAA DNA construct was generated by subcloning the GAA coding region from cDNA clone 5739991 (Invitrogen) into the pcDNA6/V5-HisA mammalian expression vector (Initrogen). The resultant DNA construct (designated as wild-type GAA cDNA) was used as the DNA template for subsequent mutagenesis. These missense, small insertion or deletion mutations are cited in the Erasmus database and known to be associated with type 2 glycogen storage disorder (GSD II), also known as Pompe disease. Briefly, wild-type GAA cDNA was PCR-amplified using mutagenic primers to obtain plasmid DNA with the desired mutation These mutations were confirmed by DNA sequencing prior to protein expression in cells.

COS-7 cells (derived from green monkey embryonic kidney cells) were aseptically seeded in 12-well tissue culture plates at a cell density of ~1.4×10$^5$ cells per well in 3 ml of Dulbecco's Modified Essential Medium (DMEM) containing 10% (v/v) fetal bovine serum and grown overnight at 37° C. in a humidified 5% $CO_2$ atmosphere. On the following day, the cells (typically 60-80% confluent) were transfected with 0.75 μg of the individual DNA construct via a lipid transfection reagent such as FUGENE HD (Roche) according the manufacturer's instructions. Two wells were transfected with each DNA construct such that one well was incubated with DNJ (typically 0 μM, 20 μM, 50 μM or 100 μM) while an equivalent volume of PBS was added to the other well. Two additional wells were transfected with the empty vector (no GAA cDNA) and incubated with or without DNJ to serve as the background control for endogenous monkey GAA expression. Similarly, 2 additional wells were transfected with the wild-type human GAA cDNA and incubated with or without DNJ to serve as the positive control. All samples were incubated for ~48 hrs at 37° C. in a humidified 5% $CO_2$ atmosphere.

After the 48-hour incubation period, the spent media was removed and the cells were washed with PBS and then incubated with fresh 1-2 ml DMEM medium for 3 hours at 37° C. in a humidified 5% $CO_2$ atmosphere. The medium was subsequently removed and cells were immediately washed with PBS and lysed with 200 μl of Lysis Buffer (25 mM Bis-Tris (pH 6.5), 150 mM NaCl, 1% (v/v) Triton X-100) containing a cocktail of protease inhibitors. The cell culture plate were then gently swirled on a rotating orbital shaker apparatus for 10 min at room temperature for complete cell lysis. The resultant cell lysates were transferred to clean 1.5 ml microcentrifuge tubes and spun at 20,000×g for 10 min to pellet cellular debris. Approximately 175 μl of each supernatant sample was then transferred to a 1.5 ml fresh microcentrifuge tube. This cell lysate was used for all subsequent assays including GAA enzyme activity, total protein concentration determination, and Western blotting.

Residual GAA enzyme activity was determined for each transiently-expressed GAA using a fluorogenic 4-methylumbeliferyl-α-glucopyranoside (4-MU-α-glucose) substrate (Sigma). Briefly, 10 μl of each cell lysate was assayed (in triplicate) in a 100 μl reaction in 96-well clear bottom black plates using 3 mM 4-MU-α-glucose and 50 mM KOAc (pH 4.0). The transiently-expressed wild-type GAA sample was diluted 20-fold with Lysis Buffer to ensure that the enzymatic reaction is maintained within the linear range of the instrument. The enzyme reactions were performed at 37° C. for 1 hour and terminated by the addition of 50 μl of 500 mM $Na_2CO_3$ (pH 10.5). The assay was then read in a fluorescence plate reader (using 355 nm excitation/460 nm emission) to quantitate the amount of GAA-dependent 4-MU fluorescence liberated. The GAA enzyme activity was then extrapolated from a free 4-MU standard curve after subtracting the background fluorescence (i.e., empty vector control).

Twenty five microliters of each cell lysate was used in a parallel assay to determine the total cellular protein concentration using the bicinchoninic acid (BCA) protein assay (Pierce) according to the manufacturer's protocol. The total cellular protein concentration was extrapolated from a bovine serum albumin (BSA) standard curve.

The GAA enzyme activity for each sample was normalized to the total cellular protein concentration and expressed as the nmoles of 4-MU released/mg total protein/hr to define the GAA specific activity. The resultant GAA specific activity after DNJ treatment was compared to GAA enzyme activity of the corresponding untreated sample to determine whether a specific GAA mutant responds to DNJ.

For a single HEK-293 cell line transfected with the GAA mutation, P545L, the DNJ $EC_{50}$ was also determined (FIG. 14).

To determine the correlation of the DNJ-response measured in the COS-7 cells to patient-derived cells, DNJ-activity response was also measured ex vivo in Patient-Derived Macrophages and Lymphoblasts.

Figure 13:
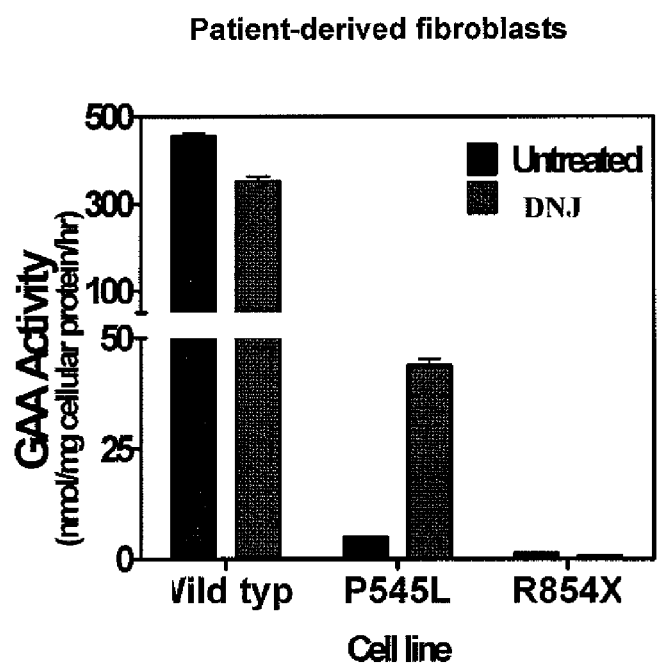
FIG. 13 Shows the responsiveness of Pompe patient-derived fibroblasts to DNJ treatment. The fibroblasts were homozygous for either the P545L or R854X GAA mutation.

Fibroblast and lymphocyte cell lines derived from Pompe patients were also generated as previously described (see U.S. Ser. No. 11/749,512). Fibroblast cell lines were derived from patients homozygous for the P545L or R854X GAA mutations (FIG. 13). Lymphocyte cell lines were derived from patients heterozygous for the (IVS1AS, T>G, -13) GAA splicing defect and GAA frameshift mutation (FIG. 15).

Figure 15:
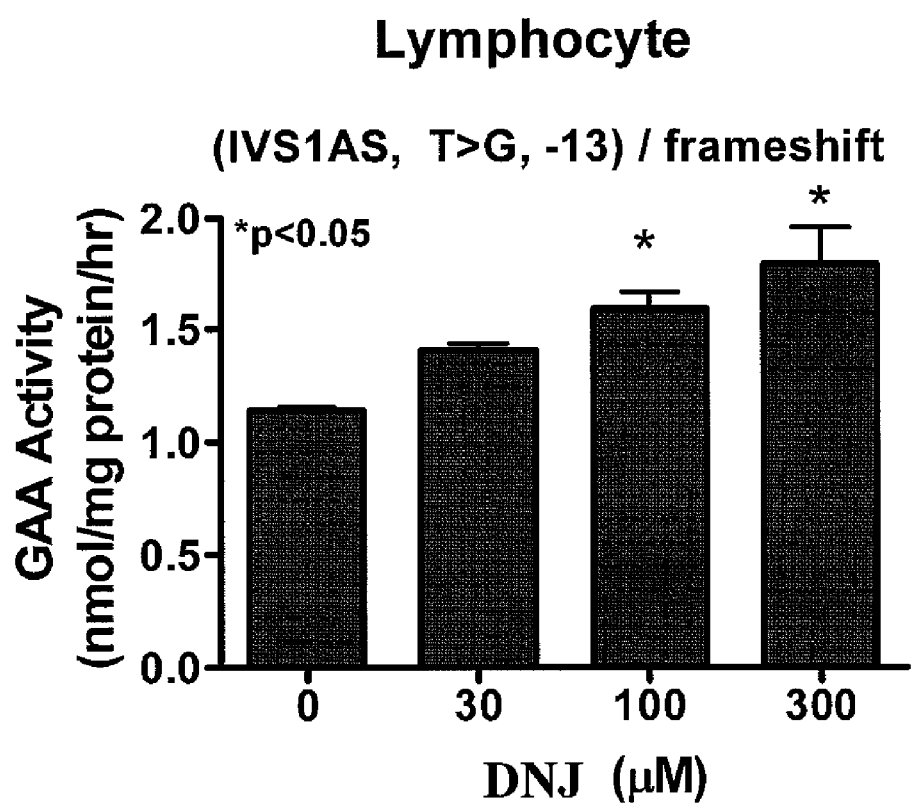
FIG. 15 Shows the responsiveness of Pompe patient-derived lymphocytes to DNJ treatment. The lymphocyes were heterozygous for the (IVSIAS, T>G, −13) GAA splicing defect and a GAA frameshift mutation.

GAA activity was measured in the lymphocyte cell lines following incubation in 0 μM, 30 μM, 100 μM, or 300 μM DNJ (FIG. 15). GAA activity was also measured in the fibroblast cell lines following DNJ incubation (FIG. 13).

In this study, the pharmacological chaperone 1-deoxynojirimycin-HCl (DNJ) is shown to bind mutant GAA and increase its activity. In Pompe patient-derived fibroblasts (FIG. 13) and lymphocytes (FIG. 15), as well as in transiently transfected COS-7 (FIGS. 10 and 12) or HEK-293 (FIG. 14) cells expressing certain GAA missense mutations, DNJ significantly increases GAA levels.

DNJ increased GAA activity for 26 mutations (FIG. 10) out of 131 mutants tested (data not shown). In addition to increasing the activity of these mutant GAA's, DNJ also promoted processing of GAA to the 95/76/70 kDa forms.

Furthermore, dose-dependent increases in GAA activity was observed in patient-derived lymphocytes containing the common IVS1AS, T>G, -13 splicing defect in one allele and a frameshift mutation in the second allele (FIG. 15).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, GenBank Accession Numbers, and protocols are cited throughout this application, the disclosures of which are incorporated herein by reference in their entireties for all purpose.

What is claimed is:

1. A method of treating a patient diagnosed with Fabry disease which comprises administering to the patient a therapeutically effective dose of 1-deoxygalactonorjirimycin, wherein the patient is identified as having a mutant α-galactosidase A, relative to a human α-galactosidase A encoded by a nucleic acid sequence set forth in SEQ ID NO:2, said mutation selected from the group consisting of the α-galactosidase A mutations A121T, A288D, A288P, A292P A348P, A73V, C52R, C94Y, D234E, D244H, D264Y, E338K, E341D, E398K, E48K, G271S, G35R, H225R, I219N, I242N, I270T, I303N, I317T, I354K, L14P, L243F, L300F, L310F, L45R, M267I, M76R, N224S, N298K, N298S, N320I, N34K, P205R, P259L, P265L, P265R, P293A, P293S, P409S, P40L, P40S, Q279R, Q280H, Q280K, Q321E, Q321R, Q327E, R301P, R49G, R49L, R49S, S201Y, S276N, S297C, S345P, V269M, W340R, W47L, and W95S.

2. The method of claim 1 wherein the patient is female.

3. The method of claim 1, wherein 1-deoxygalactonojirimycin is in a pharmaceutically acceptable salt form.

4. The method of claim 3, wherein the pharmaceutically acceptable salt form is 1-deoxygalactonojirimycin hydrochloride.

* * * * *

SEQUENCE LISTING

<160> NUMBER OF SEQ ID NOS: 566

<210> SEQ ID NO 1
<211> LENGTH: 398
<212> TYPE: PRT
<213> ORGANISM: Homo sapiens

<400> SEQUENCE: 1

```
Leu Asp Asn Gly Leu Ala Arg Thr Pro Thr Met Gly Trp Leu His Trp
 1               5                  10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
        35                  40                  45

Gly Trp Lys Asp Ala Gly Tyr Glu Tyr Leu Cys Ile Asp Asp Cys Trp
    50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
        115                 120                 125

Ala Asp Trp Gly Val Asp Leu Leu Lys Phe Asp Gly Cys Tyr Cys Asp
    130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
    210                 215                 220
```

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
            245                 250                 255

Ala Ile Met Ala Ala Pro Leu Phe Met Ser Asn Asp Leu Arg His Ile
        260                 265                 270

Ser Pro Gln Ala Lys Ala Leu Leu Gln Asp Lys Asp Val Ile Ala Ile
    275                 280                 285

Asn Gln Asp Pro Leu Gly Lys Gln Gly Tyr Gln Leu Arg Gln Gly Asp
290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
            325                 330                 335

Ala Val Ala Ser Leu Gly Lys Gly Val Ala Cys Asn Pro Ala Cys Phe
        340                 345                 350

Ile Thr Gln Leu Leu Pro Val Lys Arg Lys Leu Gly Phe Tyr Glu Trp
    355                 360                 365

Thr Ser Arg Leu Arg Ser His Ile Asn Pro Thr Gly Thr Val Leu Leu
370                 375                 380

Gln Leu Glu Asn Thr Met Gln Met Ser Leu Lys Asp Leu Leu
385                 390                 395

<210> SEQ ID NO 2
<211> LENGTH: 1312
<212> TYPE: DNA
<213> ORGANISM: Homo sapiens

<400> SEQUENCE: 2

```
gaattctccg gtcaccgtga caatgcagct gaggaaccca gaactacatc tgggctgcgc    60
gcttgcgctt cgcttcctgg ccctcgtttc ctgggacatc cctggggcta gagcactgga   120
caatggattg gcaaggacgc ctaccatggg ctggctgcac tgggagcgct tcatgtgcaa   180
ccttgactgc caggaagagc cagattcctg catcagtgag aagctcttca tggagatggc   240
agagctcatg gtctcagaag gctggaagga tgcaggttat gagtacctct gcattgatga   300
ctgttggatg gctccccaaa gagattcaga aggcagactt caggcagacc tcagcgcttt   360 cctcatggg attcgccagc tagctaatta tgttcacagc aaaggactga agctagggat   420
ttatgcagat gttggaaata aacctgcgc aggcttccct gggagttttg atactacga   480 cattgatgcc cagacctttg ctgactgggg agtagatctg ctaaaatttg atggttgtta   540
ctgtgacagt ttggaaaatt tggcagatgg ttataagcac atgtccttgg ccctgaatag   600
gactggcaga agcattgtgt actcctgtga gtggcctctt tatatgtggc cctttcaaaa   660
gcccaattat acagaaatcc gacagtactg caatcactgg cgaaattttg ctgacattga   720
tgattcctgg aaaagtataa agagtatctt ggactggaca tcttttaacc aggagagaat   780
tgttgatgtt gctggaccag ggggttggaa tgacccagat atgttagtga ttggcaactt   840
tggcctcagc tggaatcagc aagtaactca gatggccctc tgggctatca tggctgctcc   900
tttattcatg tctaatgacc tccgacacat cagccctcaa gccaaagctc tccttcagga   960
taaggacgta attgccatca atcaggaccc cttgggcaag caagggtacc agcttagaca  1020
gggagacaac tttgaagtgt gggaacgacc tctctcaggc ttagcctggg ctgtagctat  1080
gataaaccgg caggagattg gtggacctcg ctcttatacc atcgcagttg cttccctggg  1140
```

| | |
|---|---:|
| taaaggagtg gcctgtaatc ctgcctgctt catcacacag ctcctccctg tgaaaaggaa | 1200 |
| gctagggttc tatgaatgga cttcaaggtt aagaagtcac ataaatccca caggcactgt | 1260 |
| tttgcttcag ctagaaaata caatgcagat gtcattaaaa gacttacttt aa | 1312 |

<210> SEQ ID NO 3
<211> LENGTH: 3624
<212> TYPE: DNA
<213> ORGANISM: Homo sapiens

<400> SEQUENCE: 3

| | |
|---|---:|
| cagttgggaa agctgaggtt gtcgccgggg ccgcgggtgg aggtcgggga tgaggcagca | 60 |
| ggtaggacag tgacctcggt gacgcgaagg accccggcca cctctaggtt ctcctcgtcc | 120 |
| gcccgttgtt cagcgaggga ggctctgggc ctgccgcagc tgacgggaa actgaggcac | 180 |
| ggagcgggcc tgtaggagct gtccaggcca tctccaacca tgggagtgag gcacccgccc | 240 |
| tgctcccacc ggctcctggc cgtctgcgcc ctcgtgtcct tggcaaccgc tgcactcctg | 300 |
| gggcacatcc tactccatga tttcctgctg gttccccgag agctgagtgg ctcctcccca | 360 |
| gtcctggagg agactcaccc agctcaccag cagggagcca gcagaccagg gccccgggat | 420 |
| gcccaggcac accccggccg tcccagagca gtgcccacac agtgcgacgt cccccccaac | 480 |
| agccgcttcg attgcgcccc tgacaaggcc atcacccagg aacagtgcga ggcccgcggc | 540 |
| tgctgctaca tccctgcaaa gcaggggctg cagggagccc agatgggca gccctggtgc | 600 |
| ttcttcccac ccagctaccc cagctacaag ctggagaacc tgagctcctc tgaaatgggc | 660 |
| tacacggcca ccctgacccg taccaccccc accttcttcc ccaaggacat cctgaccctg | 720 |
| cggctgacg tgatgatgga gactgagaac cgcctccact tcacgatcaa agatccagct | 780 |
| aacaggcgct acgaggtgcc cttggagacc ccgcgtgtcc acagccgggc accgtcccca | 840 |
| ctctacagcg tggagttctc cgaggagccc ttcggggtga tcgtgcaccg gcagctggac | 900 |
| ggccgcgtgc tgctgaacac gacggtggcg ccctgttct ttgcgaccca gttccttcag | 960 |
| ctgtccacct cgctgccctc gcagtatatc acaggcctcg ccgagcacct cagtcccctg | 1020 |
| atgctcagca ccagctggac caggatcacc ctgtggaacc gggaccttgc gcccacgccc | 1080 |
| ggtgcgaacc tctacgggtc tcaccctttc tacctggcgc tggaggacgg cgggtcggca | 1140 |
| cacggggtgt cctgctaaa cagcaatgcc atggatgtgg tcctgcagcc gagccctgcc | 1200 |
| cttagctgga ggtcgacagg tgggatcctg gatgtctaca tcttcctggg cccagagccc | 1260 |
| aagagcgtgg tgcagcagta cctggacgtt gtgggatacc cgttcatgcc gccatactgg | 1320 |
| ggcctgggct ccacctgtg ccgctgggc tactcctcca ccgctatcac cgccaggtg | 1380 |
| gtggagaaca tgaccagggc ccacttcccc tggacgtcc aatggaacga cctggactac | 1440 |
| atggactccc ggagggactt cacgttcaac aaggatggct ccgggacttc cccggccatg | 1500 |
| gtgcaggagc tgcaccaggg cggccggcgc tacatgatga tcgtggatcc tgccatcagc | 1560 |
| agctcgggcc ctgccgggag ctacaggccc tacgacgagg gtctgcggag ggggttttc | 1620 |
| atcaccaacg agaccggcca gccgctgatt ggaaggtat ggcccgggtc cactgccttc | 1680 |
| cccgacttca ccaaccccac agccctggcc tggtgggagg acatggtggc tgagttccat | 1740 |
| gaccaggtgc ccttcgacgg catgtggatt gacatgaacg agccttccaa cttcatcaga | 1800 |
| ggctctgagg acgctgccc caacaatgag ctggagaacc caccctacgt gcctggggtg | 1860 |
| gttgggggga cctccaggc ggccaccatc tgtgcctcca gccaccagtt tctctccaca | 1920 |
| cactacaacc tgcacaacct ctacggcctg accgaagcca tcgcctccca caggcgctg | 1980 |

```
gtgaaggctc gggggacacg cccatttgtg atctcccgct cgacctttgc tggccacggc    2040
cgatacgccg gccactggac gggggacgtg tggagctcct gggagcagct cgcctcctcc    2100
gtgccagaaa tcctgcagtt taacctgctg ggggtgcctc tggtcggggc cgacgtctgc    2160
ggcttcctgg gcaacacctc agaggagctg tgtgtgcgct ggacccagct gggggccttc    2220
taccccttca tgcggaacca acagcctg ctcagtctgc ccaggagcc gtacagcttc       2280 agcgagccgg cccagcaggc catgaggaag ccctcaccc tgcgctacgc actcctcccc     2340
cacctctaca cactgttcca ccaggcccac gtcgcggggg agaccgtggc ccggcccctc    2400
ttcctggagt tccccaagga ctctagcacc tggactgtgg accaccagct cctgtggggg    2460
gaggccctgc tcatcacccc agtgctccag gccgggaagg ccgaagtgac tggctacttc    2520
cccttgggca catggtacga cctgcagacg gtgccaatag aggcccttgg cagcctccca    2580
cccccacctg cagctccccg tgagccagcc atccacagcg aggggcagtg ggtgacgctg    2640
ccggcccccc tggacaccat caacgtccac ctccgggctg gtacatcat cccctgcag     2700 ggccctggcc tcacaaccac agagtcccgc cagcagccca tggccctggc tgtggccctg    2760
accaagggtg agaggcccg aggggagctg ttctgggacg atggagagag cctgaagtg    2820 ctggagcgag gggcctacac acaggtcatc ttcctggcca ggaataacac gatcgtgaat    2880
gagctggtac gtgtgaccag tgagggagct ggcctgcagc tgcagaaggt gactgtcctg    2940
ggcgtggcca cggcgcccca gcaggtcctc tccaacggtg tccctgtctc caacttcacc    3000 tacagcccg acaccaaggt cctggacatc tgtgtctcgc tgttgatggg agagcagttt    3060
ctcgtcagct ggtgttagcc gggcggagtg tgttagtctc tccagaggga ggctggttcc    3120
ccagggaagc agagcctgtg tgcgggcagc agctgtgtgc gggcctgggg gttgcatgtg    3180
tcacctggag ctgggcacta accattccaa gccgccgcat cgcttgtttc cacctcctgg    3240
gccggggctc tggcccccaa cgtgtctagg agagctttct ccctagatcg cactgtgggc    3300
cggggcctgg agggctgctc tgtgttaata agattgtaag gtttgccctc ctcacctgtt    3360
gccggcatgc gggtagtatt agccaccccc ctccatctgt tcccagcacc ggagaagggg    3420
gtgctcaggt ggaggtgtgg ggtatgcacc tgagctcctg cttcgcgcct gctgctctgc    3480
cccaacgcga ccgcttcccg gctgcccaga gggctggatg cctgccggtc cccgagcaag    3540
cctgggaact caggaaaatt cacaggactt gggagattct aaatcttaag tgcaattatt    3600
ttaataaaag gggcatttgg aatc                                           3624
```

<210> SEQ ID NO 4
<211> LENGTH: 952
<212> TYPE: PRT
<213> ORGANISM: Homo sapiens

<400> SEQUENCE: 4

```
Met Gly Val Arg His Pro Pro Cys Ser His Arg Leu Leu Ala Val Cys
 1               5                  10                  15

Ala Leu Val Ser Leu Ala Thr Ala Ala Leu Leu Gly His Ile Leu Leu
             20                  25                  30

His Asp Phe Leu Leu Val Pro Arg Glu Leu Ser Gly Ser Ser Pro Val
         35                  40                  45

Leu Glu Glu Thr His Pro Ala His Gln Gln Gly Ala Ser Arg Pro Gly
     50                  55                  60

Pro Arg Asp Ala Gln Ala His Pro Gly Arg Pro Arg Ala Val Pro Thr
 65                  70                  75                  80

Gln Cys Asp Val Pro Pro Asn Ser Arg Phe Asp Cys Ala Pro Asp Lys
```

-continued

```
                85                  90                  95
Ala Ile Thr Gln Glu Gln Cys Glu Ala Arg Gly Cys Cys Tyr Ile Pro
            100                 105                 110
Ala Lys Gln Gly Leu Gln Gly Ala Gln Met Gly Gln Pro Trp Cys Phe
            115                 120                 125
Phe Pro Pro Ser Tyr Pro Ser Tyr Lys Leu Glu Asn Leu Ser Ser Ser
            130                 135                 140
Glu Met Gly Tyr Thr Ala Thr Leu Thr Arg Thr Thr Pro Thr Phe Phe
145                 150                 155                 160
Pro Lys Asp Ile Leu Thr Leu Arg Leu Asp Val Met Met Glu Thr Glu
                165                 170                 175
Asn Arg Leu His Phe Thr Ile Lys Asp Pro Ala Asn Arg Arg Tyr Glu
                180                 185                 190
Val Pro Leu Glu Thr Pro Arg Val His Ser Arg Ala Pro Ser Pro Leu
                195                 200                 205
Tyr Ser Val Glu Phe Ser Glu Glu Pro Phe Gly Val Ile Val His Arg
            210                 215                 220
Gln Leu Asp Gly Arg Val Leu Leu Asn Thr Thr Val Ala Pro Leu Phe
225                 230                 235                 240
Phe Ala Asp Gln Phe Leu Gln Leu Ser Thr Ser Leu Pro Ser Gln Tyr
                245                 250                 255
Ile Thr Gly Leu Ala Glu His Leu Ser Pro Leu Met Leu Ser Thr Ser
            260                 265                 270
Trp Thr Arg Ile Thr Leu Trp Asn Arg Asp Leu Ala Pro Thr Pro Gly
            275                 280                 285
Ala Asn Leu Tyr Gly Ser His Pro Phe Tyr Leu Ala Leu Glu Asp Gly
            290                 295                 300
Gly Ser Ala His Gly Val Phe Leu Leu Asn Ser Asn Ala Met Asp Val
305                 310                 315                 320
Val Leu Gln Pro Ser Pro Ala Leu Ser Trp Arg Ser Thr Gly Gly Ile
                325                 330                 335
Leu Asp Val Tyr Ile Phe Leu Gly Pro Glu Pro Lys Ser Val Val Gln
                340                 345                 350
Gln Tyr Leu Asp Val Val Gly Tyr Pro Phe Met Pro Pro Tyr Trp Gly
            355                 360                 365
Leu Gly Phe His Leu Cys Arg Trp Gly Tyr Ser Ser Thr Ala Ile Thr
            370                 375                 380
Arg Gln Val Val Glu Asn Met Thr Arg Ala His Phe Pro Leu Asp Val
385                 390                 395                 400
Gln Trp Asn Asp Leu Asp Tyr Met Asp Ser Arg Arg Asp Phe Thr Phe
                405                 410                 415
Asn Lys Asp Gly Phe Arg Asp Phe Pro Ala Met Val Gln Glu Leu His
                420                 425                 430
Gln Gly Gly Arg Arg Tyr Met Met Ile Val Asp Pro Ala Ile Ser Ser
            435                 440                 445
Ser Gly Pro Ala Gly Ser Tyr Arg Pro Tyr Asp Glu Gly Leu Arg Arg
450                 455                 460
Gly Val Phe Ile Thr Asn Glu Thr Gly Gln Pro Leu Ile Gly Lys Val
465                 470                 475                 480
Trp Pro Gly Ser Thr Ala Phe Pro Asp Phe Thr Asn Pro Thr Ala Leu
                485                 490                 495
Ala Trp Trp Glu Asp Met Val Ala Glu Phe His Asp Gln Val Pro Phe
            500                 505                 510
```

-continued

```
Asp Gly Met Trp Ile Asp Met Asn Glu Pro Ser Asn Phe Ile Arg Gly
            515                 520                 525

Ser Glu Asp Gly Cys Pro Asn Asn Leu Glu Asn Pro Pro Tyr Val
    530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
                580                 585                 590

Thr Arg Pro Phe Val Ile Ser Arg Ser Thr Phe Ala Gly His Gly Arg
            595                 600                 605

Tyr Ala Gly His Trp Thr Gly Asp Val Trp Ser Ser Trp Glu Gln Leu
610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
            675                 680                 685

Glu Pro Ala Gln Gln Ala Met Arg Lys Ala Leu Thr Leu Arg Tyr Ala
690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
    770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940
```

Glu Gln Phe Leu Val Ser Trp Cys
945                 950

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 5
cgtgacaata cagctgag                                                 18

<210> SEQ ID NO 6
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 6
ctcagctgta ttgtcacg                                                 18

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7
caccgtgaca acgcagctga gg                                            22

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 8
cctcagctgc gttgtcacgg tg                                            22

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
ggctgcgcgc ctgcgcttcg                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
cgaagcgcag gcgcgcagcc                                               20

<210> SEQ ID NO 11
<211> LENGTH: 22
<212> TYPE: DNA

```
<213> ORGANISM: Artificial Sequence
<220> FEATURE:
<223> OTHER INFORMATION: Synthetic oligonucleotide

<400> SEQUENCE: 11
gcgcttgcgc mtcgcttcct gg                                              22

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
ccaggaagcg akgcgcaagc gc                                              22

<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 13
gcttcgcttc ccggccctcg tttc                                            24

<210> SEQ ID NO 14
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 14
gaaacgaggg ccgggaagcg aagc                                            24

<210> SEQ ID NO 15
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 15
ggggctagag tactggacaa tgg                                             23

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 16
ccattgtcca gtactctagc ccc                                             23

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
gctagagcac cggacaatgg a                                               21
```

```
<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 18
tccattgtcc ggtgctctag c                                              21

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
gctagagcac cggacaatgg a                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 20
tccattgtcc ggtgctctag c                                              21

<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 21
ctagagcact gtacaatgga ttg                                            23

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 22
caatccattg tacagtgctc tag                                            23

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
gcactggaca aaggattggc                                                20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide
```

-continued

```
<400> SEQUENCE: 24
gccaatcctt tgtccagtgc                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
gcactggaca gtggattggc                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
gccaatccac tgtccagtgc                                              20

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 27
ctggacaata gattggcaag g                                            21

<210> SEQ ID NO 28
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 28
gtcagcaaaa ttttgccagt gattgc                                       26

<210> SEQ ID NO 29
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 29
gcgaaatttt actgacattg atg                                          23

<210> SEQ ID NO 30
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 30
catcaatgtc agtaaaattt cgc                                          23

<210> SEQ ID NO 31
<211> LENGTH: 31
<212> TYPE: DNA
```

```
<213> ORGANISM: Artificial Sequence
<220> FEATURE:
<223> OTHER INFORMATION: Synthetic oligonucleotide

<400> SEQUENCE: 31
ggcgaaattt tgctaacatt gatgattcct g                               31

<210> SEQ ID NO 32
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 32
caggaatcat caatgttagc aaaatttcgc c                               31

<210> SEQ ID NO 33
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 33
cgaaattttg ctggcattga tgatattc                                   28

<210> SEQ ID NO 34
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 34
gaatatcatc aatgccagca aaatttcg                                   28

<210> SEQ ID NO 35
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 35
tgacattgat gagtcctgga aaag                                       24

<210> SEQ ID NO 36
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 36
cttttccagg actcatcaat gtca                                       24

<210> SEQ ID NO 37
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 37
gctgacattg attattcctg gaaaag                                     26
```

<210> SEQ ID NO 38
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 38
cttttccagg aataatcaat gtcagc                                          26

<210> SEQ ID NO 39
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 39
ctgacattga tgattgctgg aaaagtataa agag                                 34

<210> SEQ ID NO 40
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 40
ctctttatac ttttccagca atcatcaatg tcag                                 34

<210> SEQ ID NO 41
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 41
gctgacattg atgattcccg gaaaagtata aagagtatc                            39

<210> SEQ ID NO 42
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 42
gatactcttt atactttttcc gggaatcatc aatgtcagc                           39

<210> SEQ ID NO 43
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 43
tgatgattcc ttgaaaagta taa                                             23

<210> SEQ ID NO 44
<211> LENGTH: 23
<212> TYPE: DNA
<213> ORGANISM: Artificial Sequence
<220> FEATURE:
<223> OTHER INFORMATION: Synthetic oligonucleotide

```
<400> SEQUENCE: 44
ttatactttt caaggaatca tca                                              23

<210> SEQ ID NO 45
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 45
ctgacattga tgattccttg aaaagtataa agag                                  34

<210> SEQ ID NO 46
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 46
ctctttatac ttttcaagga atcatcaatg tcag                                  34

<210> SEQ ID NO 47
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 47
gctgacattg atgattcctg taaaagtata aagagtatct tgg                        43

<210> SEQ ID NO 48
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 48
ccaagatact ctttatactt ttacaggaat catcaatgtc agc                        43

<210> SEQ ID NO 49
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 49
tggaaaagta caaagagtat c                                                21

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 50
gatactcttt gtactttcc a                                                 21

<210> SEQ ID NO 51
<211> LENGTH: 21
<212> TYPE: DNA
```

<210> SEQ ID NO 51
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 51
ccttgccaat ctattgtcca g                                      21

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
aatggattgg taaggacgcc                                        20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
ggcgtcctta ccaatccatt                                        20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
gcaaggacgc ttaccatggg                                        20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
cccatggtaa gcgtccttgc                                        20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
gcaaggacgt ctaccatggg                                        20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
cccatggtag acgtccttgc                                        20

```
<210> SEQ ID NO 58
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 58
aggacgccta ccacgggctg gctgcac                                          27

<210> SEQ ID NO 59
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 59
gtgcagccag cccgtggtag gcgtcct                                          27

<210> SEQ ID NO 60
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 60
aggacgccta ccttgggctg gctgcac                                          27

<210> SEQ ID NO 61
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 61
gtgcagccag cccaaggtag gcgtcct                                          27

<210> SEQ ID NO 62
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 62
aggacgccta ccgtgggctg gctgc                                            25

<210> SEQ ID NO 63
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 63
gcagccagcc cacggtaggc gtcct                                            25

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 64
ctaccatggw ctggctgcac                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
gtgcagccag wccatggtag                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 66
ctaccatgcg ctggctgcac                                              20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
gtgcagccag cgcatggtag                                              20

<210> SEQ ID NO 68
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 68
catgggctgt ctgcactgg                                               19

<210> SEQ ID NO 69
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 69
ccagtgcaga cagcccatg                                               19

<210> SEQ ID NO 70
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 70
atgggctggc ggcactggga g                                            21

<210> SEQ ID NO 71
<211> LENGTH: 21
<212> TYPE: DNA
```

```
<213> ORGANISM: Artificial Sequence
<220> FEATURE:
<223> OTHER INFORMATION: Synthetic oligonucleotide

<400> SEQUENCE: 71
ctcccagtgc cgccagccca t                                              21

<210> SEQ ID NO 72
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 72
ctggctgcgc tgggagc                                                   17

<210> SEQ ID NO 73
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 73
gctcccagcg cagccag                                                   17

<210> SEQ ID NO 74
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 74
ctggctgtac tgggagc                                                   17

<210> SEQ ID NO 75
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 75
gctcccagta cagccag                                                   17

<210> SEQ ID NO 76
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 76
gattcctgga aaagtacaaa gagtatcttg gactg                               35

<210> SEQ ID NO 77
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 77
cagtccaaga tactctttgt acttttccag gaatc                               35
```

<210> SEQ ID NO 78
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 78
agtataaaga gtttcttgga ctggac                                        26

<210> SEQ ID NO 79
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 79
gtccagtcca agaaactctt tatact                                        26

<210> SEQ ID NO 80
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 80
gtataaagag taacttggac tgg                                           23

<210> SEQ ID NO 81
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 81
ccagtccaag ttactcttta tac                                           23

<210> SEQ ID NO 82
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 82
agagtatctt cgactggaca tc                                            22

<210> SEQ ID NO 83
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 83
gatgtccagt cgaagatact ct                                            22

<210> SEQ ID NO 84
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 84
gagtatcttg cactggacat c                                             21

<210> SEQ ID NO 85
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 85
gatgtccagt cgaagatact ct                                            22

<210> SEQ ID NO 86
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 86
cttggactgg acatgtttta accaggagag                                    30

<210> SEQ ID NO 87
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 87
ctctcctggt taaaacatgt ccagtccaag                                    30

<210> SEQ ID NO 88
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 88
ggactggaca ccttttaacc a                                             21

<210> SEQ ID NO 89
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 89
tggttaaaag gtgtccagtc c                                             21

<210> SEQ ID NO 90
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 90
gttgatgttc ctggaccag                                                19

<210> SEQ ID NO 91
<211> LENGTH: 19
<212> TYPE: DNA

```
<213> ORGANISM: Artificial Sequence
<220> FEATURE:
<223> OTHER INFORMATION: Synthetic oligonucleotide

<400> SEQUENCE: 91
ctggtccagg aacatcaac                                                  19

<210> SEQ ID NO 92
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 92
gatgttgctc gaccagggg                                                  19

<210> SEQ ID NO 93
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 93
cccctggtcg agcaacatc                                                  19

<210> SEQ ID NO 94
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 94
gatgttgctg gacgaggggg ttgga                                           25

<210> SEQ ID NO 95
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 95
tccaaccccc tcgtccagca acatc                                           25

<210> SEQ ID NO 96
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 96
gttgctggac taggggttg g                                                21

<210> SEQ ID NO 97
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 97
ccaaccccct agtccagcaa c                                               21
```

<210> SEQ ID NO 98
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 98
gctggaccag cgggttggaa tg                                          22

<210> SEQ ID NO 99
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 99
cattccaacc cgctggtcca gc                                          22

<210> SEQ ID NO 100
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 100
ggaccagggg attggaatga c                                           21

<210> SEQ ID NO 101
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 101
ctggctgcac ggggagcgct tc                                          22

<210> SEQ ID NO 102
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 102
gaagcgctcc ccgtgcagcc ag                                          22

<210> SEQ ID NO 103
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 103
ctggctgcac ttggagcgct tc                                          22

<210> SEQ ID NO 104
<211> LENGTH: 22
<212> TYPE: DNA
<213> ORGANISM: Artificial Sequence
<220> FEATURE:
<223> OTHER INFORMATION: Synthetic oligonucleotide -continued

<400> SEQUENCE: 104
gaagcgctcc aagtgcagcc ag                                              22

<210> SEQ ID NO 105
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 105
gctgcactgg aagcgcttca tg                                              22

<210> SEQ ID NO 106
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 106
catgaagcgc ttccagtgca gc                                              22

<210> SEQ ID NO 107
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 107
actgggagcy cttcatgtgc                                                 20

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 108
gcacatgaag rgctcccagt                                                 20

<210> SEQ ID NO 109
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 109
cactgggagr gcttcatgt                                                  19

<210> SEQ ID NO 110
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 110
acatgaagcy ctcccagtg                                                  19

<210> SEQ ID NO 111
<211> LENGTH: 22
<212> TYPE: DNA

```
<213> ORGANISM: Artificial Sequence
<220> FEATURE:
<223> OTHER INFORMATION: Synthetic oligonucleotide

<400> SEQUENCE: 111
ctgggagcgc tgcatgtgca ac                                          22

<210> SEQ ID NO 112
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 112
gttgcacatg cagcgctccc ag                                          22

<210> SEQ ID NO 113
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 113
gagcgcttca agtgcaacct tg                                          22

<210> SEQ ID NO 114
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 114
caaggttgca cttgaagcgc tc                                          22

<210> SEQ ID NO 115
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 115
gcgcttcata tgcaacc                                                17

<210> SEQ ID NO 116
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 116
ggttgcatat gaagcgc                                                17

<210> SEQ ID NO 117
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 117
gagcgcttca tgtccaacct tgactg                                      26
```

<210> SEQ ID NO 118
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 118
cagtcaaggt tggacatgaa gcgctc                                  26

<210> SEQ ID NO 119
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 119
cgcttcatgs gcaaccttga c                                       21

<210> SEQ ID NO 120
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 120
gtcaaggttg cscatgaagc g                                       21

<210> SEQ ID NO 121
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 121
caaccttgac ggccaggaag                                         20

<210> SEQ ID NO 122
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 122
cttcctggcc gtcaaggttg                                         20

<210> SEQ ID NO 123
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 123
caaccttgac twccaggaag ag                                      22

<210> SEQ ID NO 124
<211> LENGTH: 22
<212> TYPE: DNA
<213> ORGANISM: Artificial Sequence
<220> FEATURE:
<223> OTHER INFORMATION: Synthetic oligonucleotide -continued

<400> SEQUENCE: 124
ctcttcctgg wagtcaaggt tg                                    22

<210> SEQ ID NO 125
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 125
gtgcaacctt gactaccagg aagagccag                             29

<210> SEQ ID NO 126
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 126
gtcattccaa tccctggtc c                                      21

<210> SEQ ID NO 127
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 127 caggggttg caatgaccca g                                      21

<210> SEQ ID NO 128
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 128
ctgggtcatt gcaaccccct g                                     21

<210> SEQ ID NO 129
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 129
ggggttggag tgacccaga                                        19

<210> SEQ ID NO 130
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 130
tctgggtcac tccaacccc                                        19

<210> SEQ ID NO 131
<211> LENGTH: 21
<212> TYPE: DNA

<213> ORGANISM: Artificial Sequence
<220> FEATURE:
<223> OTHER INFORMATION: Synthetic oligonucleotide

<400> SEQUENCE: 131
ggttggaatg tcccagatat g                                      21

<210> SEQ ID NO 132
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 132
catatctggg acattccaac c                                      21

<210> SEQ ID NO 133
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 133
gggttggaat tacccagata tg                                     22

<210> SEQ ID NO 134
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 134
catatctggg taattccaac cc                                     22

<210> SEQ ID NO 135
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 135
tggaatgacc gagatatgtt a                                      21

<210> SEQ ID NO 136
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 136
taacatatct cggtcattcc a                                      21

<210> SEQ ID NO 137
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 137
ttggaatgac ctagatatgt tag                                    23

<210> SEQ ID NO 138
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 138
ctaacatatc taggtcattc caa                                          23

<210> SEQ ID NO 139
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 139
ggaatgaccc amatatgtta gtg                                          23

<210> SEQ ID NO 140
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 140
cactaacata ttgggtcatt cc                                           22

<210> SEQ ID NO 141
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 141
ggttggaatg acccacatat gttagtgatt gg                                32

<210> SEQ ID NO 142
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 142
ccaatcacta acatatgtgg gtcattccaa cc                                32

<210> SEQ ID NO 143
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 143
gaatgaccca gttatgttag tg                                           22

<210> SEQ ID NO 144
<211> LENGTH: 22
<212> TYPE: DNA
<213> ORGANISM: Artificial Sequence
<220> FEATURE:
<223> OTHER INFORMATION: Synthetic oligonucleotide -continued

```
<400> SEQUENCE: 144
cactaacata actgggtcat tc                                              22

<210> SEQ ID NO 145
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 145
atgacccaga aatgttagtg a                                               21

<210> SEQ ID NO 146
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 146
tcactaacat ttctgggtca t                                               21

<210> SEQ ID NO 147
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 147
gacccagata ggttagtgat tg                                              22

<210> SEQ ID NO 148
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 148
caatcactaa cctatctggg tc                                              22

<210> SEQ ID NO 149
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 149
gacccagata tattagtgat tgg                                             23

<210> SEQ ID NO 150
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 150
ccaatcacta atatatctgg gtc                                             23

<210> SEQ ID NO 151
<211> LENGTH: 29
<212> TYPE: DNA
```

```
<213> ORGANISM: Artificial Sequence
<220> FEATURE:
<223> OTHER INFORMATION: Synthetic oligonucleotide

<400> SEQUENCE: 151
ctggctcttc ctggtagtca aggttgcac                                         29

<210> SEQ ID NO 152
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 152
gagccagatt cctacatcag tgagaagc                                          28

<210> SEQ ID NO 153
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 153
gcttctcact gatgtaggaa tctggctc                                          28

<210> SEQ ID NO 154
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 154
tcctgcatca ctgagaagct c                                                 21

<210> SEQ ID NO 155
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 155
gagcttctca gtgatgcagg a                                                 21

<210> SEQ ID NO 156
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 156
ctgcatcagt aagaagctct tc                                                22

<210> SEQ ID NO 157
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 157
gaagagcttc ttactgatgc ag                                                22
```

```
<210> SEQ ID NO 158
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 158
ctgcatcagt gggaagctct tc                                              22

<210> SEQ ID NO 159
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 159
gaagagcttc ccactgatgc ag                                              22

<210> SEQ ID NO 160
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 160
cagtgagaag ttcttcatgg                                                 20

<210> SEQ ID NO 161
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 161
ccaggaagaa cttctcactg                                                 20

<210> SEQ ID NO 162
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 162
gcatcagtga gaagttcttc atggagatg                                       29

<210> SEQ ID NO 163
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 163
catctccatg aagaacttct cactgatgc                                       29

<210> SEQ ID NO 164
<211> LENGTH: 22
<212> TYPE: DNA
<213> ORGANISM: Artificial Sequence
<220> FEATURE:
<223> OTHER INFORMATION: Synthetic oligonucleotide
```

-continued

<400> SEQUENCE: 164
cttcatggag agggcagagc tc					22

<210> SEQ ID NO 165
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 165
gagctctgcc ctctccatga ag					22

<210> SEQ ID NO 166
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 166
cttcatggag atagcagagc tc					22

<210> SEQ ID NO 167
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 167
gagctctgct atctccatga ag					22

<210> SEQ ID NO 168
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 168
catggagatg gtagagctca tg					22

<210> SEQ ID NO 169
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 169
catgagctct accatctcca tg					22

<210> SEQ ID NO 170
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 170
gcagagctca gggtctcaga ag					22

<210> SEQ ID NO 171
<211> LENGTH: 22
<212> TYPE: DNA

```
<213> ORGANISM: Artificial Sequence
<220> FEATURE:
<223> OTHER INFORMATION: Synthetic oligonucleotide

<400> SEQUENCE: 171
cttctgagac cctgagctct gc                                              22

<210> SEQ ID NO 172
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 172
ctcagaaggc tgtaaggatg caggt                                           25

<210> SEQ ID NO 173
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 173
acctgcatcc ttacagcctt ctgag                                           25

<210> SEQ ID NO 174
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 174
ctcagaaggc tcgaaggatg ca                                              22

<210> SEQ ID NO 175
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 175
tgcatccttc gagccttctg ag                                              22

<210> SEQ ID NO 176
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 176
ccagatatgt cagtgattgg c                                               21

<210> SEQ ID NO 177
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 177
gccaatcact gacatatctg g                                               21
```

<210> SEQ ID NO 178
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 178
gatatgttag cgattggcaa c                                              21

<210> SEQ ID NO 179
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 179
gttgccaatc gctaacatat c                                              21

<210> SEQ ID NO 180
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 180
cagatatgtt aatgattggc aac                                            23

<210> SEQ ID NO 181
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 181
gttgccaatc attaacatat ctg                                            23

<210> SEQ ID NO 182
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 182
tatgttagtg actggcaact ttg                                            23

<210> SEQ ID NO 183
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 183
caaagttgcc agtcactaac ata                                            23

<210> SEQ ID NO 184
<211> LENGTH: 19
<212> TYPE: DNA
<213> ORGANISM: Artificial Sequence
<220> FEATURE:
<223> OTHER INFORMATION: Synthetic oligonucleotide -continued

```
<400> SEQUENCE: 184
ttagtgattg tcaactttg                                                  19

<210> SEQ ID NO 185
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 185
caaagttgac aatcactaa                                                  19

<210> SEQ ID NO 186
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 186
gttagtgatt tgcaactttg g                                               21

<210> SEQ ID NO 187
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 187
ccaaagttgc aaatcactaa c                                               21

<210> SEQ ID NO 188
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 188
tgttagtgat tagcaacttt ggc                                             23

<210> SEQ ID NO 189
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 189
gccaaagttg ctaatcacta aca                                             23

<210> SEQ ID NO 190
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 190
gtgattggca aatttggcct cag                                             23

<210> SEQ ID NO 191
<211> LENGTH: 23
<212> TYPE: DNA
```

```
<213> ORGANISM: Artificial Sequence
<220> FEATURE:
<223> OTHER INFORMATION: Synthetic oligonucleotide

<400> SEQUENCE: 191
ctgaggccaa atttgccaat cac                                             23

<210> SEQ ID NO 192
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 192
gtgattggca gctttggcct c                                               21

<210> SEQ ID NO 193
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 193
gaggccaaag ctgccaatca c                                               21

<210> SEQ ID NO 194
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 194
caactttggc ctcggctgga atcag                                           25

<210> SEQ ID NO 195
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 195
ctgattccag ccgaggccaa agttg                                           25

<210> SEQ ID NO 196
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 196
ctttggcctc aactggaatc agc                                             23

<210> SEQ ID NO 197
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 197
gctgattcca gttgaggcca aag                                             23
```

```
<210> SEQ ID NO 198
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 198
agctggaatc ggcaagtaac tc                                              22

<210> SEQ ID NO 199
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 199
gagttacttg ccgattccag ct                                              22

<210> SEQ ID NO 200
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 200
cagctggaat caccaagtaa ctc                                             23

<210> SEQ ID NO 201
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 201
gaaggatgca gattatgagt ac                                              22

<210> SEQ ID NO 202
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 202
gtactcataa tctgcatcct tc                                              22

<210> SEQ ID NO 203
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 203
ggatgcaggt tgtgagtacc tctgc                                           25

<210> SEQ ID NO 204
<211> LENGTH: 25
<212> TYPE: DNA
<213> ORGANISM: Artificial Sequence
<220> FEATURE:
<223> OTHER INFORMATION: Synthetic oligonucleotide
```

```
<400> SEQUENCE: 204
gcagaggtac tcacaacctg catcc                                          25

<210> SEQ ID NO 205
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 205
ggttatgagg acctctgcat tg                                             22

<210> SEQ ID NO 206
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 206
caatgcagag gtcctcataa cc                                             22

<210> SEQ ID NO 207
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 207
gttatgagta ccsctgcatt gatg                                           24

<210> SEQ ID NO 208
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 208
catcaatgca gsggtactca taac                                           24

<210> SEQ ID NO 209
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 209
cctctgcatt hatgactgtt g                                              21

<210> SEQ ID NO 210
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 210
caacagtcat daatgcagag g                                              21

<210> SEQ ID NO 211
<211> LENGTH: 27
<212> TYPE: DNA
```

```
<213> ORGANISM: Artificial Sequence
<220> FEATURE:
<223> OTHER INFORMATION: Synthetic oligonucleotide

<400> SEQUENCE: 211
tacctctgca ttaatgactg ttggatg                                              27

<210> SEQ ID NO 212
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 212
catccaacag tcattaatgc agaggta                                              27

<210> SEQ ID NO 213
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 213
tacctctgca ttcatgactg ttggatg                                              27

<210> SEQ ID NO 214
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 214
catccaacag tcatgaatgc agaggta                                              27

<210> SEQ ID NO 215
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 215
gagtacctct gcatttatga ctgttggatg gctc                                      34

<210> SEQ ID NO 216
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 216
gagccatcca acagtcataa atgcagaggt actc                                      34

<210> SEQ ID NO 217
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 217
ctgcattgat ggctgttgga tg                                                   22
```

```
<210> SEQ ID NO 218
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 218
catccaacag ccatcaatgc ag                                              22

<210> SEQ ID NO 219
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 219
ctgcattgat gtctgttgga tg                                              22

<210> SEQ ID NO 220
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 220
catccaacag acatcaatgc ag                                              22

<210> SEQ ID NO 221
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 221
ctgcattgat aactgttgga tg                                              22

<210> SEQ ID NO 222
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 222
catccaacag ttatcaatgc ag                                              22

<210> SEQ ID NO 223
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 223
gcattgatga ctcttggatg gctc                                            24

<210> SEQ ID NO 224
<211> LENGTH: 24
<212> TYPE: DNA
<213> ORGANISM: Artificial Sequence
<220> FEATURE:
<223> OTHER INFORMATION: Synthetic oligonucleotide
```

-continued

```
<400> SEQUENCE: 224
gagccatcca agagtcatca atgc                                          24

<210> SEQ ID NO 225
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 225
gagttacttg gtgattccag ctg                                           23

<210> SEQ ID NO 226
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 226
cagctggaat aagcaagtaa c                                             21

<210> SEQ ID NO 227
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 227
gttacttgct tattccagct g                                             21

<210> SEQ ID NO 228
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 228
ggaatcagca tgtaactcag a                                             21

<210> SEQ ID NO 229
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 229
tctgagttac atgctgattc c                                             21

<210> SEQ ID NO 230
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 230
ctggaatcag aaagtaactc ag                                            22

<210> SEQ ID NO 231
<211> LENGTH: 21
<212> TYPE: DNA
```

```
<213> ORGANISM: Artificial Sequence
<220> FEATURE:
<223> OTHER INFORMATION: Synthetic oligonucleotide

<400> SEQUENCE: 231
ctgagttact ttctgattcc a                                              21

<210> SEQ ID NO 232
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 232
cagcaagtaa atcagatggc c                                              21

<210> SEQ ID NO 233
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 233
ggccatctga tttacttgct g                                              21

<210> SEQ ID NO 234
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 234
caagtaactc cgatggccct c                                              21

<210> SEQ ID NO 235
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 235
gagggccatc ggagttactt g                                              21

<210> SEQ ID NO 236
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 236
gtaactcaga cggccctctg                                                20

<210> SEQ ID NO 237
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 237
cagagggccg tctgagttac                                                20
```

-continued

```
<210> SEQ ID NO 238
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 238
taactcagat gcccctctgg gct                                              23

<210> SEQ ID NO 239
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 239
agcccagagg ggcatctgag tta                                              23

<210> SEQ ID NO 240
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 240
aactcagatg gacctctggg ct                                               22

<210> SEQ ID NO 241
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 241
agcccagagg tccatctgag tt                                               22

<210> SEQ ID NO 242
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 242
gatggccctc ggggctatca t                                                21

<210> SEQ ID NO 243
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 243
atgatagccc cgagggccat c                                                21

<210> SEQ ID NO 244
<211> LENGTH: 21
<212> TYPE: DNA
<213> ORGANISM: Artificial Sequence
<220> FEATURE:
<223> OTHER INFORMATION: Synthetic oligonucleotide
```

```
<400> SEQUENCE: 244
atggccctct gtgctatcat g                                             21

<210> SEQ ID NO 245
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 245
catgatagca cagagggcca t                                             21

<210> SEQ ID NO 246
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 246
gccctctggg atatcatggc tg                                            22

<210> SEQ ID NO 247
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 247
cagccatgat atcccagagg gc                                            22

<210> SEQ ID NO 248
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 248
gccctctggc ctatcatgg                                                19

<210> SEQ ID NO 249
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 249
gcattgatga ctattggatg gctc                                          24

<210> SEQ ID NO 250
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 250
gagccatcca atagtcatca atgc                                          24

<210> SEQ ID NO 251
<211> LENGTH: 21
<212> TYPE: DNA
```

```
<213> ORGANISM: Artificial Sequence
<220> FEATURE:
<223> OTHER INFORMATION: Synthetic oligonucleotide

<400> SEQUENCE: 251
gatgactgtt cgatggctcc c                                        21

<210> SEQ ID NO 252
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 252
gggagccatc gaacagtcat c                                        21

<210> SEQ ID NO 253
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 253
ctgttggatg cctccccaaa gag                                      23

<210> SEQ ID NO 254
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 254
ctctttgggg aggcatccaa cag                                      23

<210> SEQ ID NO 255
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 255
gctccccaaa magattcaga ag                                       22

<210> SEQ ID NO 256
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 256
cttctgaatc tktttgggga gc                                       22

<210> SEQ ID NO 257
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 257
ggctccccaa acagattcag aagg                                     24
```

<210> SEQ ID NO 258
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 258
ccttctgaat ctgtttgggg agcc                                   24

<210> SEQ ID NO 259
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 259
caaagagatt cacaaggcag acttc                                  25

<210> SEQ ID NO 260
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 260
gaagtctgcc ttgtgaatct ctttg                                  25

<210> SEQ ID NO 261
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 261
gcagaccctc agagctttcc tcatg                                  25

<210> SEQ ID NO 262
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 262
catgaggaaa gctctgaggg tctgc                                  25

<210> SEQ ID NO 263
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 263
cagaccctca gtgctttcct catg                                   24

<210> SEQ ID NO 264
<211> LENGTH: 24
<212> TYPE: DNA
<213> ORGANISM: Artificial Sequence
<220> FEATURE:
<223> OTHER INFORMATION: Synthetic oligonucleotide

```
<400> SEQUENCE: 264
catgaggaaa gcactgaggg tctg                                          24

<210> SEQ ID NO 265
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 265
ccctcagcgc tctcctcatg                                               20

<210> SEQ ID NO 266
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 266
catgaggaga gcgctgaggg                                               20

<210> SEQ ID NO 267
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 267
ctcatgggat tgccagcta gc                                             22

<210> SEQ ID NO 268
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 268
gctagctggc aaatcccatg ag                                            22

<210> SEQ ID NO 269
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 269
gattcgccag ccagctaatt atg                                           23

<210> SEQ ID NO 270
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 270
cataattagc tggctggcga atc                                           23

<210> SEQ ID NO 271
<211> LENGTH: 28
<212> TYPE: DNA
```

<213> ORGANISM: Artificial Sequence
<220> FEATURE:
<223> OTHER INFORMATION: Synthetic oligonucleotide

<400> SEQUENCE: 271
tcgccagcta mctaattatg ttcacagc                28

<210> SEQ ID NO 272
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 272
gctgtgaaca taattagkta gctggcga                28

<210> SEQ ID NO 273
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 273
gctagctaat tatgatcaca gcaaaggac                29

<210> SEQ ID NO 274
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 274
ccatgatagg ccagagggc                19

<210> SEQ ID NO 275
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 275
ctctgggctt tcatggctgc tcctt                25

<210> SEQ ID NO 276
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 276
aaggagcagc catgaaagcc cagag                25

<210> SEQ ID NO 277
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 277
gggctatcat cgctgctcct t                21

```
<210> SEQ ID NO 278
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 278
aaggagcagc gatgatagcc c                                            21

<210> SEQ ID NO 279
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 279
ctatcatggc tcctccttta ttc                                          23

<210> SEQ ID NO 280
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 280
gaataaagga ggagccatga tag                                          23

<210> SEQ ID NO 281
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 281
catggctgct gctttattca tg                                           22

<210> SEQ ID NO 282
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 282
catgaataaa gcagcagcca tg                                           22

<210> SEQ ID NO 283
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 283
catggctgct wctttattca tg                                           22

<210> SEQ ID NO 284
<211> LENGTH: 22
<212> TYPE: DNA
<213> ORGANISM: Artificial Sequence
<220> FEATURE:
<223> OTHER INFORMATION: Synthetic oligonucleotide
```

<400> SEQUENCE: 284
catgaataaa gwagcagcca tg                                    22

<210> SEQ ID NO 285
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 285
gctgctcctt tatgcatgtc taatgacc                              28

<210> SEQ ID NO 286
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 286
ggtcattaga catgcataaa ggagcagc                              28

<210> SEQ ID NO 287
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 287
ctttattcat gtktaatgac ctccg                                 25

<210> SEQ ID NO 288
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 288
cggaggtcat tamacatgaa taaag                                 25

<210> SEQ ID NO 289
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 289
attcatgtct agtgacctcc gac                                   23

<210> SEQ ID NO 290
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 290
gtcggaggtc actagacatg aat                                   23

<210> SEQ ID NO 291
<211> LENGTH: 24
<212> TYPE: DNA

<213> ORGANISM: Artificial Sequence
<220> FEATURE:
<223> OTHER INFORMATION: Synthetic oligonucleotide

<400> SEQUENCE: 291
tattcatgtc taaggacctc cgac                                          24

<210> SEQ ID NO 292
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 292
gtcggaggtc cttagacatg aata                                          24

<210> SEQ ID NO 293
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 293
tattcatgtc tcatgacctc cgac                                          24

<210> SEQ ID NO 294
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 294
gtcggaggtc atgagacatg aata                                          24

<210> SEQ ID NO 295
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 295
tcatgtctaa tggcctccga cacatc                                        26

<210> SEQ ID NO 296
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 296
gatgtgtcgg aggccattag acatga                                        26

<210> SEQ ID NO 297
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 297
gtctaatgac ccccgacaca tcag                                          24

<210> SEQ ID NO 298
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 298
ctgatgtgtc gggggtcatt agac         24

<210> SEQ ID NO 299
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 299
gtcctttgct gtgatcataa ttagctagc    29

<210> SEQ ID NO 300
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 300
cacagcaaag aactgaagct ag           22

<210> SEQ ID NO 301
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 301
ctagcttcag ttctttgctg tg           22

<210> SEQ ID NO 302
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 302
cagcaaagga ccgaagctag g            21

<210> SEQ ID NO 303
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 303
atccctagct tcggtccttt gctg         24

<210> SEQ ID NO 304
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 304
aggactgaag ccagggattt atgc                                            24

<210> SEQ ID NO 305
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 305
gcataaatcc ctggcttcag tcct                                            24

<210> SEQ ID NO 306
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 306
ggactgaagc tagagattta tgcagatg                                        28

<210> SEQ ID NO 307
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 307
catctgcata aatctctagc ttcagtcc                                        28

<210> SEQ ID NO 308
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 308
gactgaagct aaggatttat gcagatg                                         27

<210> SEQ ID NO 309
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 309
catctgcata aatccttagc ttcagtc                                         27

<210> SEQ ID NO 310
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 310
gctagggatt tctgcagatg ttgg                                            24

<210> SEQ ID NO 311
<211> LENGTH: 24
<212> TYPE: DNA

```
<213> ORGANISM: Artificial Sequence
<220> FEATURE:
<223> OTHER INFORMATION: Synthetic oligonucleotide

<400> SEQUENCE: 311
ccaacatctg cagaaatccc tagc                                              24

<210> SEQ ID NO 312
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 312
gctagggatt tatgtagatg ttgga                                             25

<210> SEQ ID NO 313
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 313
tccaacatct acataaatcc ctagc                                             25

<210> SEQ ID NO 314
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 314
ggatttatgc acatgttgga a                                                 21

<210> SEQ ID NO 315
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 315
ttccaacatg tgcataaatc c                                                 21

<210> SEQ ID NO 316
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 316
gggatttatg cacatgttgg aaataaaacc                                        30

<210> SEQ ID NO 317
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 317
ggttttattt ccaacatgtg cataaatccc                                        30
```

<210> SEQ ID NO 318
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 318
tgcagatgtt gaaaataaaa cctg                                        24

<210> SEQ ID NO 319
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 319
caggttttat tttcaacatc tgca                                        24

<210> SEQ ID NO 320
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 320
tgcagatgtt agaaataaaa cctg                                        24

<210> SEQ ID NO 321
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 321
caggttttat ttctaacatc tgca                                        24

<210> SEQ ID NO 322
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 322
ggatttatgc agatgttgaa aataaaacct gcgcagc                          37

<210> SEQ ID NO 323
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 323
gctgcgcagg ttttattttc aacatctgca taaatcc                          37

<210> SEQ ID NO 324
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 324
gtctaatgac ttccgacaca tc                                    22

<210> SEQ ID NO 325
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 325
gatgtgtcgg aagtcattag ac                                    22

<210> SEQ ID NO 326
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 326
gtctaatgac caccgacaca tc                                    22

<210> SEQ ID NO 327
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 327
gatgtgtcgg tggtcattag ac                                    22

<210> SEQ ID NO 328
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 328
ctaatgacct cggacacatc agc                                   23

<210> SEQ ID NO 329
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 329
gctgatgtgt ccgaggtcat tag                                   23

<210> SEQ ID NO 330
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 330
ctaatgacct cccacacatc agc                                   23

<210> SEQ ID NO 331
<211> LENGTH: 23
<212> TYPE: DNA

```
<213> ORGANISM: Artificial Sequence
<220> FEATURE:
<223> OTHER INFORMATION: Synthetic oligonucleotide

<400> SEQUENCE: 331
gctgatgtgt gggaggtcat tag                                             23

<210> SEQ ID NO 332
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 332
ctccgacaca acagccctca agc                                             23

<210> SEQ ID NO 333
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 333
gcttgagggc tgttgtgtcg gag                                             23

<210> SEQ ID NO 334
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 334
gccaaagctt tccttcagga                                                 20

<210> SEQ ID NO 335
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 335
tcctgaagga aagctttggc                                                 20

<210> SEQ ID NO 336
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 336
gctctccttc acgataagga cg                                              22

<210> SEQ ID NO 337
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 337
cgtccttatc gtgaaggaga gc                                              22
```

-continued

<210> SEQ ID NO 338
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 338
ctctccttca gtataaggac g                                              21

<210> SEQ ID NO 339
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 339
cgtccttata ctgaaggaga g                                              21

<210> SEQ ID NO 340
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 340
gataaggacg aaattgccat c                                              21

<210> SEQ ID NO 341
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 341
gatggcaatt tcgtccttat c                                              21

<210> SEQ ID NO 342
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 342
aaggacgtaa mtgccatcaa tc                                             22

<210> SEQ ID NO 343
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 343
gattgatggc akttacgtcc tt                                             22

<210> SEQ ID NO 344
<211> LENGTH: 22
<212> TYPE: DNA
<213> ORGANISM: Artificial Sequence
<220> FEATURE:
<223> OTHER INFORMATION: Synthetic oligonucleotide

```
<400> SEQUENCE: 344
aattgccatc attcaggacc cc                                          22

<210> SEQ ID NO 345
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 345
ggggtcctga atgatggcaa tt                                          22

<210> SEQ ID NO 346
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 346
aattgccatc aagcaggacc cc                                          22

<210> SEQ ID NO 347
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 347
ggggtcctgc ttgatggcaa tt                                          22

<210> SEQ ID NO 348
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 348
aattgccatc tatcaggacc cc                                          22

<210> SEQ ID NO 349
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 349
ggatttatgc agatgttcga aataaaacct gcgcagc                          37

<210> SEQ ID NO 350
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 350
ggatttatgc agatgttcga aataaaacct gcgcagc                          37

<210> SEQ ID NO 351
<211> LENGTH: 22
<212> TYPE: DNA
```

```
<213> ORGANISM: Artificial Sequence
<220> FEATURE:
<223> OTHER INFORMATION: Synthetic oligonucleotide

<400> SEQUENCE: 351
ggaaataaaa tctgcgcagg ct                                              22

<210> SEQ ID NO 352
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 352
agcctgcgca gattttattt cc                                              22

<210> SEQ ID NO 353
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 353
ggaaataaaa cccgcgcagg cttc                                            24

<210> SEQ ID NO 354
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 354
gaagcctgcg cgggttttat ttcc                                            24

<210> SEQ ID NO 355
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 355
gaaataaaac ctrcgcaggc ttcc                                            24

<210> SEQ ID NO 356
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 356
ggaagcctgc gyaggtttta tttc                                            24

<210> SEQ ID NO 357
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 357
ggaaataaaa cctgggcagg cttccctg                                        28
```

```
<210> SEQ ID NO 358
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 358
cagggaagcc tgcccaggtt ttatttcc                                         28

<210> SEQ ID NO 359
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 359
gaaataaaac ctgcacaggc ttccc                                            25

<210> SEQ ID NO 360
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 360
gggaagcctg tgcaggtttt atttc                                            25

<210> SEQ ID NO 361
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 361
ataaaacctg cccaggcttc cc                                               22

<210> SEQ ID NO 362
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 362
gggaagcctg ggcaggtttt at                                               22

<210> SEQ ID NO 363
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 363
cctgcgcagt cttccctgg                                                   19

<210> SEQ ID NO 364
<211> LENGTH: 19
<212> TYPE: DNA
<213> ORGANISM: Artificial Sequence
<220> FEATURE:
<223> OTHER INFORMATION: Synthetic oligonucleotide
```

```
<400> SEQUENCE: 364
ccagggaaga ctgcgcagg                                              19

<210> SEQ ID NO 365
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 365
ggcttcccta ggagttttgg                                             20

<210> SEQ ID NO 366
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 366
ccaaaactcc tagggaagcc                                             20

<210> SEQ ID NO 367
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 367
ttccctggga attttggata c                                           21

<210> SEQ ID NO 368
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 368
gtatccaaaa ttcccaggga a                                           21

<210> SEQ ID NO 369
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 369
ccctgggagg tttggatact                                             20

<210> SEQ ID NO 370
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 370
agtatccaaa cctcccaggg                                             20

<210> SEQ ID NO 371
<211> LENGTH: 24
<212> TYPE: DNA
```

```
<213> ORGANISM: Artificial Sequence
<220> FEATURE:
<223> OTHER INFORMATION: Synthetic oligonucleotide

<400> SEQUENCE: 371
gttttggata ctgcgacatt gatg                                          24

<210> SEQ ID NO 372
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 372
catcaatgtc gcagtatcca aaac                                          24

<210> SEQ ID NO 373
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 373
ggggtcctga tagatggcaa tt                                            22

<210> SEQ ID NO 374
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 374
tgccatcaat gaggacccct tg                                            22

<210> SEQ ID NO 375
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 375
caaggggtcc tcattgatgg ca                                            22

<210> SEQ ID NO 376
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 376
tgccatcaat cgggacccct tg                                            22

<210> SEQ ID NO 377
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 377
caaggggtcc cgattgatgg ca                                            22
```

```
<210> SEQ ID NO 378
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 378
ggaccccttg gacaagcaag                                                    20

<210> SEQ ID NO 379
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 379
cttgcttgtc caagggggtcc                                                   20

<210> SEQ ID NO 380
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 380
cttgggcaag raagggtacc ag                                                 22

<210> SEQ ID NO 381
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 381
ctggtaccct tycttgccca ag                                                 22

<210> SEQ ID NO 382
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 382
ggcaagcaaa ggtaccagc                                                     19

<210> SEQ ID NO 383
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 383
gctggtacct ttgcttgcc                                                     19

<210> SEQ ID NO 384
<211> LENGTH: 19
<212> TYPE: DNA
<213> ORGANISM: Artificial Sequence
<220> FEATURE:
<223> OTHER INFORMATION: Synthetic oligonucleotide
```

```
<400> SEQUENCE: 384
ggcaagcaag ygtaccagc                                            19

<210> SEQ ID NO 385
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 385
gctggtacrc ttgcttgcc                                            19

<210> SEQ ID NO 386
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 386
tgggcaagca agagtaccag cttag                                     25

<210> SEQ ID NO 387
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 387
ctaagctggt actcttgctt gccca                                     25

<210> SEQ ID NO 388
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 388
gagacaactt taaagtgtgg g                                         21

<210> SEQ ID NO 389
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 389
cccacacttt aaagttgtct c                                         21

<210> SEQ ID NO 390
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 390
ctttgaagtg cgggaacgac                                           20

<210> SEQ ID NO 391
<211> LENGTH: 20
<212> TYPE: DNA
```

```
<213> ORGANISM: Artificial Sequence
<220> FEATURE:
<223> OTHER INFORMATION: Synthetic oligonucleotide

<400> SEQUENCE: 391
gtcgttcccg cacttcaaag                                              20

<210> SEQ ID NO 392
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 392
gaagtgtggg accgacctct ctc                                          23

<210> SEQ ID NO 393
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 393
gagagaggtc ggtcccacac ttc                                          23

<210> SEQ ID NO 394
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 394
gaagtgtgga acgacctct ctc                                           23

<210> SEQ ID NO 395
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 395
gagagaggtc gtttccacac ttc                                          23

<210> SEQ ID NO 396
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 396
gtgtgggaac aacctctctc ag                                           22

<210> SEQ ID NO 397
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 397
ctacgacatt catgcccaga c                                            21
```

```
<210> SEQ ID NO 398
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 398
gtctgggcat gaatgtcgta g                                              21

<210> SEQ ID NO 399
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 399
gacattgata cccagacctt tg                                             22

<210> SEQ ID NO 400
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 400
caaaggtctg ggtatcaatg tc                                             22

<210> SEQ ID NO 401
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 401
ctttgctgac cggggagtag atc                                            23

<210> SEQ ID NO 402
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 402
gatctactcc ccggtcagca aag                                            23

<210> SEQ ID NO 403
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 403
ctttgctgac tgcggagtag atc                                            23

<210> SEQ ID NO 404
<211> LENGTH: 23
<212> TYPE: DNA
<213> ORGANISM: Artificial Sequence
<220> FEATURE:
<223> OTHER INFORMATION: Synthetic oligonucleotide
```

<400> SEQUENCE: 404
gatctactcc gcagtcagca aag                                        23

<210> SEQ ID NO 405
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 405
gctgactggg tagtagatct g                                          21

<210> SEQ ID NO 406
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 406
cagatctact acccagtcag c                                          21

<210> SEQ ID NO 407
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 407
ctggggagta gttctgctaa aatttg                                     26

<210> SEQ ID NO 408
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 408
caaattttag cagaactact ccccag                                     26

<210> SEQ ID NO 409
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 409
gagtagatct gccaaaattt gatgg                                      25

<210> SEQ ID NO 410
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 410
ccatcaaatt ttggcagatc tactc                                      25

<210> SEQ ID NO 411
<211> LENGTH: 27
<212> TYPE: DNA

```
<213> ORGANISM: Artificial Sequence
<220> FEATURE:
<223> OTHER INFORMATION: Synthetic oligonucleotide

<400> SEQUENCE: 411
gtagatctgc taagatttga tggtttg                                          27

<210> SEQ ID NO 412
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 412
caaaccatca aatcttagca gatctac                                          27

<210> SEQ ID NO 413
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 413
gtagatctgc taaaatctga tggttgttac tg                                    32

<210> SEQ ID NO 414
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 414
cagtaacaac catcagattt tagcagatct ac                                    32

<210> SEQ ID NO 415
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 415
gctaaaattt gttggttgtt actg                                             24

<210> SEQ ID NO 416
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 416
cagtaacaac caacaaattt tagc                                             24

<210> SEQ ID NO 417
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 417
gctaaaattt catggttgtt actg                                             24
```

```
<210> SEQ ID NO 418
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 418
cagtaacaac catgaaattt tagc                                            24

<210> SEQ ID NO 419
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 419
ctaaaatttg atgattgtta ctgtgac                                         27

<210> SEQ ID NO 420
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 420
gtcacagtaa caatcatcaa attttag                                         27

<210> SEQ ID NO 421
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 421
ctaaaatttg atcgttgtta ctgtgac                                         27

<210> SEQ ID NO 422
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 422
ctgagagagg ttgttcccac ac                                              22

<210> SEQ ID NO 423
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 423
gaacgacctc cctcaggctt ag                                              22

<210> SEQ ID NO 424
<211> LENGTH: 22
<212> TYPE: DNA
<213> ORGANISM: Artificial Sequence
<220> FEATURE:
<223> OTHER INFORMATION: Synthetic oligonucleotide
```

```
<400> SEQUENCE: 424
ctaagcctga gggaggtcgt tc                                              22

<210> SEQ ID NO 425
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 425
cgacctctcc caggcttagc c                                               21

<210> SEQ ID NO 426
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 426
ggctaagcct gggagaggtc g                                               21

<210> SEQ ID NO 427
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 427
ctcaggctta ccctgggctg tag                                             23

<210> SEQ ID NO 428
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 428
ctacagccca gggtaagcct gag                                             23

<210> SEQ ID NO 429
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 429
cttagcctgg cctgtagcta tg                                              22

<210> SEQ ID NO 430
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 430
catagctaca ggccaggcta ag                                              22

<210> SEQ ID NO 431
<211> LENGTH: 22
<212> TYPE: DNA
```

-continued

<213> ORGANISM: Artificial Sequence
<220> FEATURE:
<223> OTHER INFORMATION: Synthetic oligonucleotide

<400> SEQUENCE: 431
ctgggctgta gatatgataa ac                          22

<210> SEQ ID NO 432
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 432
gtttatcata tctacagccc ag                          22

<210> SEQ ID NO 433
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 433
gtagctatga aaaccggca gg                           22

<210> SEQ ID NO 434
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 434
cctgccggtt tttcatagct ac                          22

<210> SEQ ID NO 435
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 435
gctatgataa aacggcagga g                           21

<210> SEQ ID NO 436
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 436
ctcctgccgt tttatcatag c                           21

<210> SEQ ID NO 437
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 437
gctatgataa actggcagga gatt                        24

```
<210> SEQ ID NO 438
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 438
aatctcctgc cagtttatca tagc                                        24

<210> SEQ ID NO 439
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 439
accggcaggs gattggtgga c                                           21

<210> SEQ ID NO 440
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 440
gtccaccaat cscctgccgg t                                           21

<210> SEQ ID NO 441
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 441
gataaaccgg cagaagattg gtgg                                        24

<210> SEQ ID NO 442
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 442
ccaccaatct tctgccggtt tatc                                        24

<210> SEQ ID NO 443
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 443
gataaaccgg caggcgattg gtggacctc                                   29

<210> SEQ ID NO 444
<211> LENGTH: 29
<212> TYPE: DNA
<213> ORGANISM: Artificial Sequence
<220> FEATURE:
<223> OTHER INFORMATION: Synthetic oligonucleotide
```

```
<400> SEQUENCE: 444
gaggtccacc aatcgcctgc cggtttatc                              29

<210> SEQ ID NO 445
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 445
ccggcaggag actggtggac ctc                                    23

<210> SEQ ID NO 446
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 446
gaggtccacc agtctcctgc cgg                                    23

<210> SEQ ID NO 447
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 447
gtcacagtaa caacgatcaa attttag                                27

<210> SEQ ID NO 448
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 448
ctaaaatttg atggttwtta ctgtgacagt                             30

<210> SEQ ID NO 449
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 449
actgtcacag taawaaccat caaattttag                             30

<210> SEQ ID NO 450
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 450
ctaaaatttg atggttggta ctgtgacagt                             30

<210> SEQ ID NO 451
<211> LENGTH: 30
<212> TYPE: DNA
```

```
<213> ORGANISM: Artificial Sequence
<220> FEATURE:
<223> OTHER INFORMATION: Synthetic oligonucleotide

<400> SEQUENCE: 451
actgtcacag taccaaccat caaattttag                                30

<210> SEQ ID NO 452
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 452
ctaaaatttg atggtcgtta ctgtgacagt                                30

<210> SEQ ID NO 453
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 453
actgtcacag taacgaccat caaattttag                                30

<210> SEQ ID NO 454
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 454
ctaaaatttg atggtggtta ctgtgacagt                                30

<210> SEQ ID NO 455
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 455
actgtcacag taaccaccat caaattttag                                30

<210> SEQ ID NO 456
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 456
ttggcagatg attataagca c                                         21

<210> SEQ ID NO 457
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 457
gtgcttataa tcatctgcca a                                         21
```

```
<210> SEQ ID NO 458
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 458
ttggcagata gttataagca c                                              21

<210> SEQ ID NO 459
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 459
gtgcttataa ctatctgcca a                                              21

<210> SEQ ID NO 460
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 460
gttataagca cacgtccttg gccct                                          25

<210> SEQ ID NO 461
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 461
agggccaagg acgtgtgctt ataac                                          25

<210> SEQ ID NO 462
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 462
gttataagca cgtgtccttg gcc                                            23

<210> SEQ ID NO 463
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 463
ggccaaggac acgtgcttat aac                                            23

<210> SEQ ID NO 464
<211> LENGTH: 23
<212> TYPE: DNA
<213> ORGANISM: Artificial Sequence
<220> FEATURE:
<223> OTHER INFORMATION: Synthetic oligonucleotide
```

```
<400> SEQUENCE: 464
gtccttggcc cagaatagga ctg                                              23

<210> SEQ ID NO 465
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 465
cagtcctatt ctgggccaag gac                                              23

<210> SEQ ID NO 466
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 466
gtccttggcc ccgaatagga ctg                                              23

<210> SEQ ID NO 467
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 467
cagtcctatt cggggccaag gac                                              23

<210> SEQ ID NO 468
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 468
ctgaatagga ttggcagaag c                                                21

<210> SEQ ID NO 469
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 469
gcttctgcca atcctattca g                                                21

<210> SEQ ID NO 470
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 470
cagaagcatt atgtactcct g                                                21

<210> SEQ ID NO 471
<211> LENGTH: 21
<212> TYPE: DNA
```

```
<213> ORGANISM: Artificial Sequence
<220> FEATURE:
<223> OTHER INFORMATION: Synthetic oligonucleotide

<400> SEQUENCE: 471
caggagtaca taatgcttct g                                         21

<210> SEQ ID NO 472
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 472
caggagatta gtggacctcg c                                         21

<210> SEQ ID NO 473
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 473
gcgaggtcca ctaatctcct g                                         21

<210> SEQ ID NO 474
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 474
ggagattggt agacctcgct c                                         21

<210> SEQ ID NO 475
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 475
gagcgaggtc taccaatctc c                                         21

<210> SEQ ID NO 476
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 476
gattggtgga cttcgctctt atac                                      24

<210> SEQ ID NO 477
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 477
gtataagagc gaagtccacc aatc                                      24
```

```
<210> SEQ ID NO 478
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 478
ggtggacctc actcttatac                                               20

<210> SEQ ID NO 479
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 479
gtataagagt gaggtccacc                                               20

<210> SEQ ID NO 480
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 480
ggtggacctt gctcttatac                                               20

<210> SEQ ID NO 481
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 481
gtataagagc aaggtccacc                                               20

<210> SEQ ID NO 482
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 482
tgcttccctg cgtaaaggag tgg                                           23

<210> SEQ ID NO 483
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 483
ccactccttt acgcagggaa gca                                           23

<210> SEQ ID NO 484
<211> LENGTH: 24
<212> TYPE: DNA
<213> ORGANISM: Artificial Sequence
<220> FEATURE:
<223> OTHER INFORMATION: Synthetic oligonucleotide
```

-continued

<400> SEQUENCE: 484
gtaaaggagt ggactgtaat cctg                                              24

<210> SEQ ID NO 485
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 485
caggattaca gtccactcct ttac                                              24

<210> SEQ ID NO 486
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 486
aaaggagtgg cctataatcc tgcc                                              24

<210> SEQ ID NO 487
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 487
ggcaggatta taggccactc cttt                                              24

<210> SEQ ID NO 488
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 488
aaaggagtgg cccgtaatcc tgcc                                              24

<210> SEQ ID NO 489
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 489
ggcaggatta cgggccactc cttt                                              24

<210> SEQ ID NO 490
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 490
gtaatcctgc ctacttcatc acac                                              24

<210> SEQ ID NO 491
<211> LENGTH: 24
<212> TYPE: DNA

```
<213> ORGANISM: Artificial Sequence
<220> FEATURE:
<223> OTHER INFORMATION: Synthetic oligonucleotide

<400> SEQUENCE: 491
gtgtgatgaa gtaggcagga ttac                                          24

<210> SEQ ID NO 492
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 492
ctgcctgctt caacacacag ctcctc                                        26

<210> SEQ ID NO 493
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 493
gaggagctgt gtgttgaagc aggcag                                        26

<210> SEQ ID NO 494
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 494
cctgcttcat cccacagctc ctcc                                          24

<210> SEQ ID NO 495
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 495
ggaggagctg tgggatgaag cagg                                          24

<210> SEQ ID NO 496
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 496
cttcatcaca ccgctcctcc ctgt                                          24

<210> SEQ ID NO 497
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 497
cattgtgtac ttctgtgagt gg                                            22
```

```
<210> SEQ ID NO 498
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 498
ccactcacag aagtacacaa tg                                              22

<210> SEQ ID NO 499
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 499
cattgtgtac tactgtgagt ggc                                             23

<210> SEQ ID NO 500
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 500
gccactcaca gtagtacaca atg                                             23

<210> SEQ ID NO 501
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 501
gtgtactcct atgagtggcc tc                                              22

<210> SEQ ID NO 502
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 502
gaggccactc ataggagtac ac                                              22

<210> SEQ ID NO 503
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 503
gtgtactcct gggagtggcc tct                                             23

<210> SEQ ID NO 504
<211> LENGTH: 23
<212> TYPE: DNA
<213> ORGANISM: Artificial Sequence
<220> FEATURE:
<223> OTHER INFORMATION: Synthetic oligonucleotide
```

<400> SEQUENCE: 504
agaggccact cccaggagta cac                                          23

<210> SEQ ID NO 505
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 505
ctgtgagtgg actctttata tg                                           22

<210> SEQ ID NO 506
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 506
catataaaga gtccactcac ag                                           22

<210> SEQ ID NO 507
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 507
ctgtgagtgg cktctttata tg                                           22

<210> SEQ ID NO 508
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 508
catataaaga mgccactcac ag                                           22

<210> SEQ ID NO 509
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 509
tggcctcttt ctatgtggcc c                                            21

<210> SEQ ID NO 510
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 510
gggccacata gaaagaggcc a                                            21

<210> SEQ ID NO 511
<211> LENGTH: 25
<212> TYPE: DNA

```
<213> ORGANISM: Artificial Sequence
<220> FEATURE:
<223> OTHER INFORMATION: Synthetic oligonucleotide

<400> SEQUENCE: 511
agtggcctct ttgtatgtgg ccctt                                         25

<210> SEQ ID NO 512
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 512
aagggccaca tacaaagagg ccact                                         25

<210> SEQ ID NO 513
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 513
cctttcaaaa gcccaatgat acagaaatcc gacag                              35

<210> SEQ ID NO 514
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 514
ctgtcggatt tctgtatcat tgggcttttg aaagg                              35

<210> SEQ ID NO 515
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 515
caattataca gaaaaccgac agtactgc                                      28

<210> SEQ ID NO 516
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 516
gcagtactgt cggttttctg tataattg                                      28

<210> SEQ ID NO 517
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 517
cgacagtacs gcaatcactg g                                             21
```

<210> SEQ ID NO 518
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 518
ccagtgattg csgtactgtc g                                      21

<210> SEQ ID NO 519
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 519
cgacagtact acaatcactg g                                      21

<210> SEQ ID NO 520
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 520
acagggagga gcggtgtgat gaag                                   24

<210> SEQ ID NO 521
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 521
cacagctcct ccgtgtgaaa aggaagct                               28

<210> SEQ ID NO 522
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 522
agcttccttt tcacacggag gagctgtg                               28

<210> SEQ ID NO 523
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 523
ggaagctagg gtactatgaa tgg                                    23

<210> SEQ ID NO 524
<211> LENGTH: 23
<212> TYPE: DNA
<213> ORGANISM: Artificial Sequence
<220> FEATURE:
<223> OTHER INFORMATION: Synthetic oligonucleotide

```
<400> SEQUENCE: 524
ccattcatag taccctagct tcc                                          23

<210> SEQ ID NO 525
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 525
agggttctat aaatggactt ca                                           22

<210> SEQ ID NO 526
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 526
tgaagtccat ttatagaacc ct                                           22

<210> SEQ ID NO 527
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 527
gacttcaagg tcaagaagtc ac                                           22

<210> SEQ ID NO 528
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 528
gtgacttctt gaccttgaag tc                                           22

<210> SEQ ID NO 529
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 529
gaagtcacaa aaatcccaca g                                            21

<210> SEQ ID NO 530
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 530
ctgtgggatt tttgtgactt c                                            21

<210> SEQ ID NO 531
<211> LENGTH: 24
<212> TYPE: DNA
```

```
<213> ORGANISM: Artificial Sequence
<220> FEATURE:
<223> OTHER INFORMATION: Synthetic oligonucleotide

<400> SEQUENCE: 531
gtcacataaa tdccacaggc actg                                         24

<210> SEQ ID NO 532
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 532
cagtgcctgt gghatttatg tgac                                         24

<210> SEQ ID NO 533
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 533
cacataaatc ccaaaggcac tg                                           22

<210> SEQ ID NO 534
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 534
cagtgccttt gggatttatg tg                                           22

<210> SEQ ID NO 535
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 535
cacataaatc ccgcaggcac tg                                           22

<210> SEQ ID NO 536
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 536
cagtgcctgc gggatttatg tg                                           22

<210> SEQ ID NO 537
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 537
atcccacaga cactgttttg c                                            21
```

```
<210> SEQ ID NO 538
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 538
gcaaaacagt gtctgtggga t                                          21

<210> SEQ ID NO 539
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 539
ggcactgttt cgcttcagct ag                                         22

<210> SEQ ID NO 540
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 540
ctagctgaag cgaaacagtg cc                                         22

<210> SEQ ID NO 541
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 541
gcgcttcgct tcctggacat ccctggggc                                  29

<210> SEQ ID NO 542
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 542
gccccaggga tgtccaggaa gcgaagcgc                                  29

<210> SEQ ID NO 543
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 543
ccagtgattg tagtactgtc g                                          21

<210> SEQ ID NO 544
<211> LENGTH: 21
<212> TYPE: DNA
<213> ORGANISM: Artificial Sequence
<220> FEATURE:
<223> OTHER INFORMATION: Synthetic oligonucleotide
```

-continued

```
<400> SEQUENCE: 544
cagtactgca gtcactggcg a                                              21

<210> SEQ ID NO 545
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 545
tcgccagtga ctgcagtact g                                              21

<210> SEQ ID NO 546
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 546
cagtactgcg atcactggc                                                 19

<210> SEQ ID NO 547
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 547
gccagtgatc gcagtactg                                                 19

<210> SEQ ID NO 548
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 548
tactgcaatc gctggcgaaa t                                              21

<210> SEQ ID NO 549
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 549
atttcgccag cgattgcagt a                                              21

<210> SEQ ID NO 550
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 550
gcaatcaccg gcgaaat                                                   17

<210> SEQ ID NO 551
<211> LENGTH: 17
<212> TYPE: DNA
```

```
<213> ORGANISM: Artificial Sequence
<220> FEATURE:
<223> OTHER INFORMATION: Synthetic oligonucleotide

<400> SEQUENCE: 551
atttcgccgg tgattgc                                                    17

<210> SEQ ID NO 552
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 552
gcaatcactg tcgaaatttt gc                                              22

<210> SEQ ID NO 553
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 553
gcaaaatttc gacagtgatt gc                                              22

<210> SEQ ID NO 554
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 554
gcaatcactg gcaaaatttt gctgac                                          26

<210> SEQ ID NO 555
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 555
gcagaccctc agcgccagct agctaattat g                                    31

<210> SEQ ID NO 556
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 556
cataattagc tagctggcgc tgagggtctg c                                    31

<210> SEQ ID NO 557
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 557
gttttggata ctacattgat gcccag                                          26
```

```
<210> SEQ ID NO 558
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 558
ctgggcatca atgtagtatc caaaac                                            26

<210> SEQ ID NO 559
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 559
ctcctgtgag tggatgtggc cctt                                              24

<210> SEQ ID NO 560
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 560
aagggccaca tccactcaca ggag                                              24

<210> SEQ ID NO 561
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 561
caggagagaa ttgatgttgc tgg                                               23

<210> SEQ ID NO 562
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 562
ccagcaacat caattctctc ctg                                               23

<210> SEQ ID NO 563
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 563
gataaaccgg cagattggtg gacct                                             25

<210> SEQ ID NO 564
<211> LENGTH: 25
<212> TYPE: DNA
<213> ORGANISM: Artificial Sequence
<220> FEATURE:
<223> OTHER INFORMATION: Synthetic oligonucleotide
```

```
<400> SEQUENCE: 564
aggtccacca atctgccggt ttatc                                      25

<210> SEQ ID NO 565
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 565
gactggacat cttggacatc ttttaaccag gagag                           35

<210> SEQ ID NO 566
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 566
ctctcctggt taaaagatgt ccaagatgtc cagtc                           35
```